United States Patent [19]
Schwartz et al.

[11] Patent Number: 5,470,834
[45] Date of Patent: Nov. 28, 1995

[54] SULFOXIMINE AND SULDODIIMINE MATRIX METALLOPROTEINASE INHIBITORS

[75] Inventors: Martin A. Schwartz, Tallahassee, Fla.; Harold Van Wart, Los Altos, Calif.

[73] Assignee: Florida State University, Tallahassee, Fla.

[21] Appl. No.: 132,411

[22] Filed: Oct. 6, 1993

[51] Int. Cl.$^6$ .......................... A61K 38/05; A61K 38/06; C07K 5/062; C07K 5/065
[52] U.S. Cl. .......................... 514/19; 260/998.2; 514/397; 514/400; 514/414; 514/415; 514/562; 514/607; 514/824; 514/825; 514/843; 514/912; 530/331; 548/312.1; 548/313.1; 548/313.7; 548/336.1; 548/455; 548/503
[58] Field of Search .................. 514/19, 607, 824, 514/825, 843, 912, 397, 400, 414, 415, 562; 530/331; 564/101; 260/998.2; 548/312.1, 313.1, 313.7, 336.1, 455, 503; 562/426, 427, 556

[56] References Cited

U.S. PATENT DOCUMENTS

| | | | |
|---|---|---|---|
| 5,171,885 | 12/1992 | Griffith | 562/556 |
| 5,178,877 | 1/1993 | Garren et al. | 424/456 |

FOREIGN PATENT DOCUMENTS

| | | | |
|---|---|---|---|
| 0278158A2 | 8/1988 | European Pat. Off. | C07D 233/64 |
| 0330201A2 | 8/1989 | European Pat. Off. | A61K 47/00 |
| 0497192A2 | 8/1992 | European Pat. Off. | C07C 259/06 |
| 62126-163 | 11/1985 | Japan | A61K 31/19 |
| WO89/08205 | 10/1989 | WIPO | C07C 101/24 |
| WO90/05716 | 5/1990 | WIPO | C07C 259/06 |
| 9115507 | 10/1991 | WIPO . | |
| WO92/21360 | 12/1992 | WIPO | A61K 37/00 |

OTHER PUBLICATIONS

Schwartz et al. *Progress in Medicinal Chemistry*, vol. 29, 1992, Elsevier Science Publishers, pp. 271–334.
Cappalonga et al., "Structural Comparison of Sulfodiimine, etc" *J. of Biol. Chem.* vol. 267, No. 27 (1992) pp. 19192–19197.
Mock et al. "Sulfoximine and Sulfodiimine transistor–State Analogue Inhibitors, etc." J. Am. Chem. Soc. 1989, 111, pp. 4467–4472.
M. Brannstrom, et al., "Inhibitors of Mammalian Tissue Collagenase and Metalloproteinases Suppress Ovulation in the Perfused Rat Ovary", Endicrinology 122:1715–1721 (1988).
C. Librach, et al., "92–kD Type IV Collagenase Mediates Invasion of Human Cytotrophoblasts", J. Cell Biol. 113:437–449 (1991).
L. M. Matrisian, "The Matrix–Degrading Metalloproteinases", Bioessays 14: 455–463 (1992).
H. Birkedal–Hansen, et al., "Matrix Metalloproteinases: A Review", Crit Revs. Oral Biol. Med. 4(2): 197–250 (1993).
J. M. Delaisse, et al., "The Effects of Inhibitors of Cysteine–Proteinases and Collagenase on the Resorptive Activity of Isolated Osteoclasts", Bone 8: 305–313 (1987).

J. M. Delaisse, et al., "A New Synthetic Inhibitor of Mammalian Tissue Collagenase Inhibits Bone Resorption in Culture", Biochem. Biophys. Res. Communs. 133: 483–490 (1985).
M. A. Moses, et al., "Inhibitors of Angiogenesis (Review)", Biotechnology 9: 630–634 (1991).
R. Langer, et al., "Control of tumor growth in animals by infusion of an angiogenesis inhibitor", Proc. Natl. Acad. Sci. USA 77: 4331–4335 (1980).
J. White, "Minocycline for Dystrophic Epidermolysis Bullosa", Lancet I: 966 (1988).
P. Humbert, et al., "Tetracyclines for Dystrophic Epidermolysis Bullosa", Lancet II: 277 (1989).
F. Burns, et al., "Inhibition of Alkali–Induced Corneal Ulceration and Perforation by a Thiol Peptide", Invest. Ophthalmol. Vis. Sci. 31:107–114 (1990).
A. Henney, et al., "Localization of stromelysin gene expression in atherosclerotic plaques by in situ hybridization", Proc. Natl. Acad. Sci. USA 88:8154–8158 (1991).
J. D'Amiento, et al., "Collagenase Expression in the Lungs of Transgenic Mice Causes Pulmonary Emphysema", Cell 71:955–961 (1992).

(List continued on next page.)

Primary Examiner—Peter O'Sullivan
Attorney, Agent, or Firm—Senniger, Powers, Leavitt & Roedel

[57] ABSTRACT

Novel sulfoximine and sulfodiimine matrix metalloproteinase inhibitors of the formula, Formula I $$R^1\underset{X}{\overset{O}{\underset{\|}{S}}}\overset{\|}{\underset{NH}{=}}\underset{R^2}{\overset{R^3}{\underset{|}{CH}}}\overset{O}{\underset{\|}{C}}-\underset{H}{\overset{H}{\underset{|}{N}}}-\underset{\underset{O}{\|}}{C}-\underset{H}{\overset{H}{\underset{|}{N}}}-R^4$$

wherein:
R$^1$ is selected from the group consisting of lower-alkyl, hydroxy lower-alkyl, amino lower-alkyl, carbamoyl lower-alkyl, lower-alkyl carbonyl, lower-alkyoxyalkyl, aralkyl and heteroaralkyl;
X is NH or O;
R$^2$ is selected from the group consisting of hydrogen, lower-alkyl and aralkyl;
R$^3$ is selected from the group consisting of hydrogen, lower-alkyl, amino lower-alkyl, guanyl lower-alkyl, aralkyl and heteroaralkyl; and
R$^4$ is selected from the group consisting of lower alkyl, aralkyl and —CH(R$^5$)—C(O)NH$_2$,
  wherein R$^5$ is selected from the group consisting of hydrogen, lower-alkyl, amino lower-alkyl, guanyl lower-alkyl, imidazoylalkyl, hydroxymethyl, 1-hydroxyethyl, mercapto lower-alkyl, and methylthio lower-alkyl;
useful for modulating physiological functions or treating diseases and disease conditions associated with matrix metalloproteinase modulation.

43 Claims, No Drawings

Other Publications

P. LeRoux, et al., "Synthesis of new peptide inhibitors of the meso–diaminopimelate–adding enzyme", Eur. J. Med. Chem. 27, 899–907 (1992).

M. Abo–Ghali, et al., "Synthesis of inhibitors of the meso–diaminopimelate–adding enzyme from *Escherichia coli*", Int. J. Peptide Protein Res. 32, 208–222 (1988).

SULFOXIMINE AND SULFODIIMINE MATRIX METALLOPROTEINASE INHIBITORS

BACKGROUND OF THE INVENTION

1. Field of the Invention

This invention relates to pharmaceutically active sulfoximine and sulfodiimine derivatized peptides useful as inhibitors of the matrix metalloproteinase (MMP) family of enzymes for use in modulating physiological functions or treating diseases and disease conditions associated with MMP modulation, for example: arthritic diseases, such as osteoarthritis (OA), rheumatoid arthritis (RA), septic arthritis, soft tissue rheumatism, polychondritis and tendonitis; tumor invasion in certain cancers; periodontal diseases; corneal ulceration, e.g., that induced by alkali or other burns, by radiation, by vitamin E or retinoid deficiency; glomerular diseases, such as proteinuria, dytrophobic epidermolysis bullosa; bone resorption diseases, such as osteoporosis, Paget's disease, hyperparathyroidism and cholesteatoma; birth control through preventing ovulation or implantation; angiogenesis relating to tumor growth or to the neovascularization associated with diabetic retinopathy and macular degeneration; coronary thrombosis associated with atherosclerotic plaque rupture; and pulmonary emphysema. In addition to the compounds and their use, the invention also relates to their precursors, to their preparation and to pharmaceutical compositions using the compounds of the invention.

2. Background Information

The MMPs are a family of zinc-containing proteinases believed to be responsible for the metabolic turnover of protein components of the extracellular matrix of humans. At present there are at least eight known human MMP.

Various disease and disease conditions have been linked with the actions or presence of MMP, e.g., elevated levels of certain of these enzymes exists in joints of arthritic humans and animals and therefore have been linked to the degradation of the major components of articular cartilage and basement membranes. It is presently believed that the collective action of the MMP on extracellular matrix macromolecules is responsible for the destruction of connective tissue, however, the precise role of each enzyme in the process is not yet well understood. It has also been reported that certain MMP may be instrumental in mediating certain normal physiological functions that involve the breakdown or development of tissue.

It has been desired to selectively inhibit certain MMP enzymes, specifically those which modulate certain diseases, physiological conditions and disease conditions, in order that such conditions could be controlled.

It has been surprisingly discovered that a family of sulfoximine and sulfodiimine derivatized polypeptides are potent inhibitors of MMP, thereby affording a method of treating MMP-mediated diseases and disease conditions, and controlling MMP-mediated physiological functions.

SUMMARY OF THE INVENTION

Novel sulfoximine and sulfodiimine derivatized peptides of the formula,

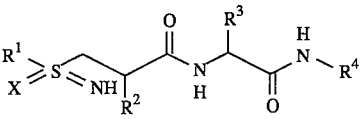

Formula I wherein:

$R^1$ is selected from the group consisting of lower-alkyl, hydroxy lower-alkyl, amino lower-alkyl, carbamoyl lower-alkyl, lower-alkyl carbonyl, lower-alkyoxyalkyl, aralkyl and heteroaralkyl;

X is NH or O;

$R^2$ is selected from the group consisting of hydrogen, lower-alkyl and aralkyl;

$R^3$ is selected from the group consisting of hydrogen, lower-alkyl, amino lower-alkyl, guanyl lower-alkyl, aralkyl and heteroaralkyl; and $R^4$ is selected from the group consisting of lower alkyl, aralkyl and —CH($R^5$)—C(O)NH$_2$,
  wherein $R^5$ is selected from the group consisting of hydrogen, lower-alkyl, amino lower-alkyl, guanyl lower-alkyl,
  imidazoylalkyl, hydroxymethyl, 1-hydroxyethyl, mercapto lower-alkyl, and methylthio lower-alkyl; or a pharmaceutically acceptable ester, ether or salt useful for modulating physiological functions or treating diseases and disease conditions associated with MMP modulation, e.g., arthritic diseases, such as osteoarthritis (OA), rheumatoid arthritis (RA), septic arthritis, soft tissue rheumatism, polychondritis and tendonitis; tumor invasion in certain cancers, periodontal diseases; corneal ulceration, e.g., that induced by alkali or other burns, by radiation, by vitamin E or retinoid deficiency; glomerular diseases, such as proteinuria, dytrophobic epidermolysis bullosa; bone resorption diseases, such as osteoporosis, Paget's disease, hyperparathyroidism and cholesteatoma; birth control through preventing ovulation or implantation; angiogenesis relating to tumor growth or to the neovascularization associated with diabetic retinopathy and macular degeneration; coronary thrombosis associated with atherosclerotic plaque rupture; and pulmonary emphysema.

DETAILED DESCRIPTION

DEFINITIONS AND GENERAL PARAMETERS

The term "alkyl" refers to a branched or straight chain monovalent saturated aliphatic hydrocarbon radical of one to twenty carbon atoms.

The term "lower-alkyl" refers to a branched or straight chain monovalent alkyl radical of one to six carbon atoms. This term is further exemplified by such radicals as methyl, ethyl, propyl, isopropyl, butyl (e.g., isobutyl, t-butyl, or n-butyl), pentyl, and hexyl.

The term "aryl" refers to an aromatic monovalent carbocyclic radical, which can optionally be mono-, di-, tri- or tetra-substituted, independently, with lower alkyl (e.g., methylphenyl, ethylphenyl), lower-alkyoxy (e.g., 4-methoxyphenyl), hydroxy (e.g., 4-hydroxyphenyl) halo, carboxy, lower-alkoxycarbonyl, carbamoyl, mono- and dimethylcarbamoyl, lower-alkyl carbonyl (such as, methylcarbonyl and ethylcarbonyl), hydroxymethyl, amino, trifluoromethyl, cyano or nitro.

The term "aralkyl" refers to the group -(lower alkyl)-(aryl). For example, typical arylalkyl groups are e.g., phenylmethyl (i.e., benzyl), phenylethyl, 4-hydroxyphenylmethyl, or 4-methoxyphenylmethyl.

The term "heteroaryl" refers to aromatic monovalent carbocyclic radical having at least one heteroatom, i.e., nitrogen, oxygen or sulfur, which can optionally be mono- or di-substituted adjacent to the heteroatom, independently, with lower alkyl, halo, cyano, amino or trifluoromethyl. For example, typical heteroaryl groups with one or more nitrogen atoms are tetrazoyl, pyridyl (e.g., 4-pyridyl, 3-pyridyl, 2-pyridyl), indolyl, pyridazinyl, quinolinyl, 2-quinolinyl, 3-quinolinyl, imidazolyl, isoquinolinyl, pyrazolyl, pyrazinyl, pyrimidinyl, pyridonyl or pyridazinonyl; typical oxygen heteroaryl radicals with oxygen atom are furanyl, or benzofuranyl; typical sulfur heteroaryl radicals are thienyl, and benzothiophenyl.

The term "heteroaralkyl" refers to the group (heteroaryl)-(lower alkyl). For example, typical heteroaralkyl groups are e.g. imidazoyl lower-alkyl, such as, 4-imidazolylmethyl, 3-imidazolylmethyl, 4-imidazoylethyl, or indolyl lower-alkyl, such as, 2-indolylmethyl, 3-indolylmethyl, The term "guanyl" refers to the moiety carbamimidoylamino

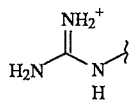

The term "sulfoximine" refers to the moiety

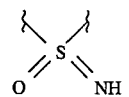

The term "sulfodiimine" refers to the moiety

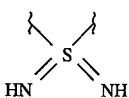

The term "blocking group" or "BG'" refer to a chemical group which exhibits the following characteristics. The group must react selectively in good yield to give a blocked or protected substrate that is stable to the projected reactions; and the blocking group must be selectively removable in good yield by readily available, preferably nontoxic reagents that do not attack the functional group(s) generated in such projected reactions. For example, typical blocking groups are benzyloxycarbonyl, tert-butyldimethylsilyl, or benzyl [for additional blocking or protecting groups see "Protective Groups", J. F. W. McOmie, Adv. Org. Chem., 3, 191 (1963) or "Protective Groups in Organic Synthesis", Theodora W. Greene and Peter G. M. Wilts, John Wiley & Sons, 2nd Edition, 1991] are used for protecting substrates containing the chemical moieties, such as 4-hydroxyphenylmethyl, 3-indolylmethyl, 4-aminobutyl, 3-guanylpropyl or 4-imidazoylmethyl.

The term "blocked" refers to a chemical moiety that has been treated with a blocking group.

The term "de-blocking" reagent refers to a reagent which is used to remove a blocking group, e.g., elemental Na and liquid ammonia for debenzylation of S-benzyl (Evans, D. A.; Mathre, D. J.; Scott, W. L. *J. Org. Chem.* 1985, 50, 1830–1835), 10% Pd/C with catalytic amount of cyclohexylamine and $H_2$ gas for removing CBz from imine moiety, or tetrabutylammonium fluoride hydrate for remove t-butyldimethylsilyl moiety.

The term "chiral auxiliary" or "CA" refers to compounds that direct the synthesis of the desired amino acid or modified amino acid in a stereospecific manner. For example, (4S, 5R)-4-methyl-5-phenyl-2-oxazolidinone, or (4R,5S)-4-methyl-5-phenyl-2-oxazolidinone.

"Enantiomers" are two stereoisomers whose molecules are non-superimposable mirror images of one another.

"Diastereoisomers" or "diastereomers" are stereoisomers with two or more centers of asymmetry and whose molecules are not mirror images of one another.

The term "racemic" means existing as a racemate, or as a 50—50 mixture of two enantiomers, also denoted by "dl" or "±".

The terms "D" and/or "L" refers to the absolute configuration at an asymmetric carbon of a molecule assigned according to experimental chemical correlation with that of the d-carbon of a modified or unmodified amino acid residue (using the absolute configuration of the α-carbon of D- or L-serine as the standard).

The designation "DL" indicates a mixture of the D and L stereoisomers or that diastereomers were separated but not identified.

Isolation and purification of the compounds and intermediates described herein can be effected, if desired, by any suitable separation or purification procedure such as, for example, filtration, extraction, crystallization, column chromatography, preparative high pressure liquid chromatography (preparative HPLC), thin-layer chromatography or thick-layer chromatography, or a combination of these procedures. Specific illustrations of suitable separation and isolation procedures can be had by reference to the examples hereinbelow. However, other equivalent separation or isolation procedures can also be used.

Nomenclature

The following convention of abbreviations and nomenclature has been adopted and will be used to name the compounds of the present invention.

Common naturally occurring amino acids relating to the present invention are listed below in tables according to their radical type (e.g., aliphatic, aromatic, basic or substituted aliphatic).

| | Radical | Abbreviation |
|---|---|---|
| Aliphatic Amino Acids | | |
| Glycine | H | Gly |
| Alanine | methyl | Ala |
| Val | 2-propyl | Val |
| Leucine | 2-methylpropyl | Leu |
| Isoleucine | 2-butyl | Ile |
| Aromatic Amino Acids | | |
| Phenylalanine | benzyl | Phe |
| Tyrosine | 4-hydroxyphenylmethyl | Tyr |
| Tryptophan | 3-indolylmethyl | Trp |
| Basic Amino Acids | | |
| Lysine | 4-aminobutyl | Lys |
| Arginine | 3-guanylpropyl | Arg |
| Histidine | 4-imidazoylmethyl | His |
| Substituted Amino Acids | | |
| Cysteine | thiolmethyl | Cys |
| Methionine | methylthioethyl | Met |
| Serine | hydroxymethyl | Ser |
| Threonine | 1-hydroxyethyl | Thr |

-continued

| Radical | Abbreviation |
| --- | --- |

The abbreviation "Ac-" refers to the acetyl radical.
The abbreviation "Bn-" or "Bnz-" refers to the benzyl radical.
The abbreviation "AcS-" refers to the thiolacetyl radical.
The abbreviation "-OEt" refers the ethoxy radical.
The abbreviation "RS-" refers to a lower-alkyl sulfide radical.
The abbreviation "BnS-" refers to the benzylsulfide radical.
The abbreviation "TBS" refers to the tert-butyldimethylsilyl radical.
The abbreviation "Cbz" refers to the benzyloxycarbonyl radical, i.e.,

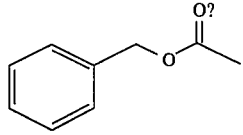

The abbreviation "(Phet)" refers to the modified amino acid with phenylethyl as the radical, i.e.,

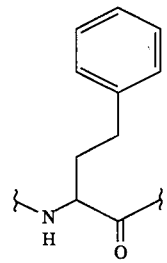

The abbreviation "(Tyr-OCH$_3$)" refers to the modified amino acid with 4-methoxyphenylmethyl as the radical, i.e.,

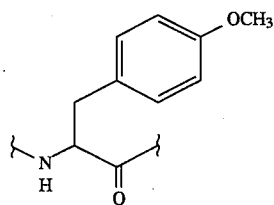

Certain naming conventions are accepted to represent the structure of modified peptides. For example, a modification of the C=O group of an amino acid residue is signified by the usual three-letter code for the residue followed by the formula of the group that has replaced the C=O, separated by a hyphen, all enclosed in parentheses, a modification of the NH group of a residue is analogously indicated by the three-letter code for the residue preceded by the formula of the group substituting for the NH, separated by a hyphen, all enclosed in parentheses, and the stereoconfiguration of the α-carbon of a residue is indicated by the letters L or D preceding the three-letter code for the residue. The absence of either letters, or the presence of both letters indicates a mixture of the L and D isomers, or that diastereomers were separated but not identified.

For example, for a dipeptide analogue of (L-Ala)-(L-Leu)

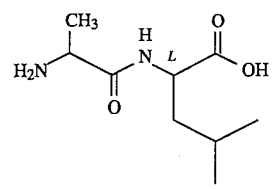

in which the C=O of Ala and NH of Leu are replaced by sulfoximine [S(O)(NH)] and methylene moieties, respectively,

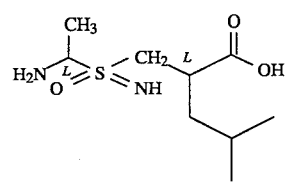

would be designated as (L-Ala-SO(NH))—(CH$_2$-L-Leu).

For example, for a dipeptide analogue of (L-Ala)-(L-Leu)

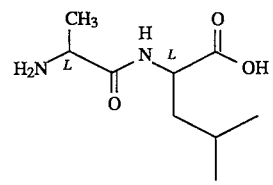

in which the C=O of Ala and NH of Leu are replaced by sulfodimine [S(NH)$_2$] and methylene moieties, respectively,

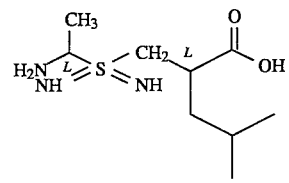

would be designated as (L-Ala-S(NH)$_2$)—(CH$_2$-L-Leu).

Some representative compounds are named in the following examples.

For example,

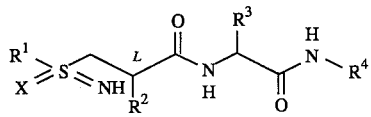

where X is O, $R^1$ is CH$_3$, $R^2$ is 2-methylpropyl, $R^3$ is phenylmethyl and $R^4$ is H, and the carbon that is the point of attachment for $R^2$ is in the L- configuration, is Me-(RS)-SO(NH)—(CH$_2$-L-Leu)-Phe-Ala-NH$_2$.

For example,

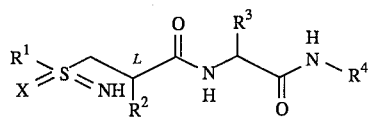

where X is NH, $R^1$ is methyl, $R^2$ is 2-methylpropyl, $R^3$ is 3-indolylmethyl and $R^4$ is phenylmethyl, and the carbon that is the point of attachment for for $R^2$ is in the L- configuration, is MeS(NH)$_2$—(CH$_2$-L-Leu)-Trp-NHBn.

SYNTHESIS OF THE COMPOUNDS OF FORMULA I

As used in the Reaction Schemes, X, $R^1$, $R^2$, $R^3$, $R^4$ and $R^5$ are the same as described in the Summary of the Invention.

Reaction Scheme A illustrates the stereospecific preparation of novel sulfoximine and sulfodiimine compounds, i.e., the compounds of Formula I. The formulae depicted in Reaction Scheme A are indicated as a single group of isomers, i.e. L-isomer, however it should be noted that Reaction Scheme A can also be used for preparing D-isomer compounds by starting with D specific starting material.

Reaction Scheme B illustrates an alternate preparation of novel sulfoximine and sulfodiimine compounds, i.e., the compounds of Formula I. The formulae depicted in Reaction Scheme B are indicated as racemic, i.e., DL, however it should be noted that the stereoconfiguration of the compounds prepared by Reaction Scheme B is governed by the stereoconfiguration of the starting materials (e.g. L-specific starting material will result in L-specific product and D-specific starting material will result in D-specific product).

Reaction Scheme C illustrates an alternate stereospecific preparation of novel sulfoximine and sulfodiimine compounds, i.e., the compounds of Formula I, where a stereospecific intermediate of Reaction Scheme A (Formula 3, L- or D-) is converted to an intermediate of Reaction Scheme B and converted to a L- or D- diastereomeric compound of Formula I by following the procedures described in Reaction Scheme B.

REACTION SCHEME A

STARTING MATERIALS

Chiral auxiliary compounds, e.g., (4S,5R)-4-methyl-5-phenyl-2-oxazolidinone, or (4R, 5S)-4-methyl-5-phenyl-2-oxazolidinone are commercially available from Aldrich Chemical Co.

PREPARATION OF FORMULA 2

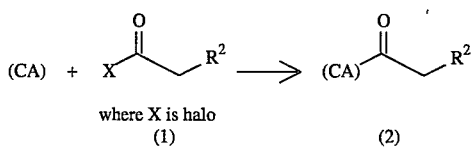

where X is halo (1)    (2)

The enantiomeric specific preparation of compounds of Formula I begin with the stereospecific synthesis of the chiral center. A procedure for this type of synthesis using a chiral auxiliary (CA) is described in Evans, D. A.; Mathre, D. J.; Scott, W. L. *J. Org. Chem.* 1985, 50, 1830–1835. For example, a chiral auxiliary, such as (4S, 5R)-4-methyl-5-phenyl-2-oxazolidinone is combined with an aprotic solvent, such as tetrahydrofuran, cooled to a temperature in the range of about –50° C. to –100° C., preferably about –78° C. with stirring. To this solution is added about 1 molar equivalent of a base, preferably, a lower-alkyl lithium base (e.g., n-butyllithium), and about 1–3 molar equivalents, preferably about 1 molar equivalent of a substituted acid halide (i.e., a compound of Formula 1, where $R^2$ is hydrogen, methyl, 2-propyl, 2-methylpropyl, 2-butyl, phenylmethyl, blocked 4-hydroxyphenylmethyl, 3-indoylmethyl, 4-methoxyphenylmethyl or phenethyl). The reaction mixture is allowed to warm to a temperature in the range of about –10° C. to 10° C., preferably about 0° C., and stirred for a period of about 15 to 45 minutes, preferably about 30 minutes. A salt solution, such as, Na$_2$CO$_3$, or K$_2$CO$_3$, preferably K$_2$CO$_3$ is added to the mixture and stirred at a temperature in the range of about 20°–30° C., preferably about room temperature for a period of about 30 minutes to 90 minutes, preferably about 60 minutes. The organic solvents are removed in vacuo, and the residue is extracted with an organic solvent (e.g., CH$_2$Cl$_2$). The extracts are combined, washed with water and brine, dried and evaporated yielding the desired optionally substituted carbonyl compound, i.e., the compound of Formula 2.

PREPARATION OF FORMULA 3

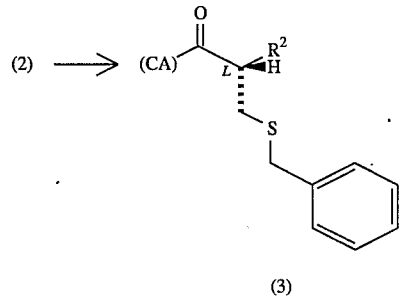

A compound of Formula 2 is dissolved in an aprotic solvent, e.g., tetrahydrofuran and combined with a lithium base solution (prepared, e.g., by combining about 1 molar equivalent of a di-substituted lower-alkyl amine with about 1 molar equivalent of a lithium base, preferably, n-butyllithium in an aprotic solvent, e.g., tetrahydrofuran). The mixture is stirred at a temperature in the range of about –50° C. to –100° C., preferably about –78° C. for a period of about 15 to 45 minutes, preferably about 30 minutes. To this solution is added about 1 molar equivalent of a benzyl halomethyl sulfide, preferably benzyl bromomethyl sulfide. The combined mixture is stirred for a period of about 1 to 3 hours, preferably 2 hours, at a temperature of about 0° C. to –50° C., preferably about –25° C., and additional for a period of 1 to 3 hours, preferably about 2 hours, at a temperature in the range of about –25° C. to 25° C., preferably about 0° C. An aqueous acid, e.g., NH$_4$Cl, is added to quench the reaction mixture. The organic solvents are removed in vacuo, and the resulting residue is extracted, washed, dried and evaporated to yield the desired enantiomerically pure optionally substituted benzyl thiol ether compound, i.e., the compound of Formula 3.

PREPARATION OF FORMULA 4

(3) → 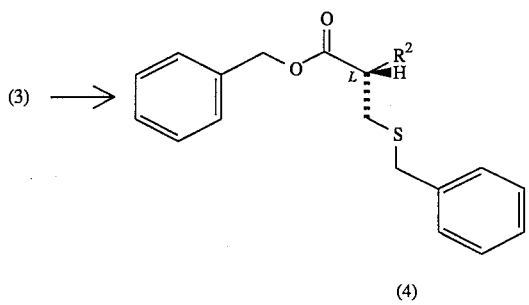

(4)

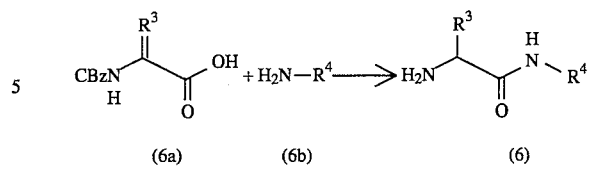

A compound of Formula 3 is dissolved in an aprotic solvent, such as tetrahydrofuran. To this solution is added a solution of lithium benzyloxide prepared by combining about 2 molar equivalents of benzyl alcohol, about 1.5 molar equivalents of n-butyllithium in an aprotic solvent, such as tetrahydrofuran over a period of about 15 to 45 minutes, preferably about 30 minutes, at a temperature in the range of about −20° C. to 0° C., preferably about −10° C. The reaction mixture is allowed to warm to about 0° C. and stirred for a period of about 1 to 2 hours, preferably about 1½ hours. A weak aqueous acid, such as saturated $NH_4Cl$ is used to quench the reaction. The organic solvents are removed by vacuum, and the residue is extracted, washed, dried and evaporated. The residual material is further purified by chromatography, e.g., flash chromatography on silica gel yielding the enantiomerically pure optionally substituted benzyl ester benzylthioether, i.e., the compound of Formula 4.

PREPARATION OF FORMULA 5

(4) → 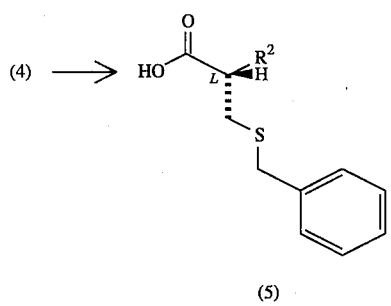

(5)

A compound of Formula 4 is combined with a solution of 30% anhydrous hydrogen bromide (about 4 molar equivalents) and glacial acetic (about 13 molar equivalents). The mixture is stirred at a temperature in the range of about 25° C. to 75° C., preferably about 50° C. for a period of about 15 to 45 minutes, preferably about 30 minutes. The reaction mixture is cooled, diluted with water and extracted. The resultant extracts are washed several times to remove residual acid. The crude product is further purified by combining with KOH, extraction with ether, adjustment of pH, extraction with ether, drying and evaporation to give the desired 3-benzylthio-(L-2-optionally substituted)propanoic acid, i.e., the compound of Formula 5.

PREPARATION OF FORMULA 6

A compound of Formula 6 is formed by the following procedure, which is a modification of procedures reported in Bodanszky, M.; Bodanszky, A. *The Practice of Peptide Synthesis;* Springer-Verlag: New York, 1984; p 129–142. A compound of Formula 6a (where $R^3$ is hydrogen, lower-alkyl, blocked 4-aminobutyl, blocked 3-guanylpropyl, blocked 4-imidazoylmethyl, phenylmethyl, blocked 4-hydroxyphenylmethyl, 3-indolylmethyl, 4-methoxyphenylmethyl or phenethyl) is combined with about 1 to 1.2 molar equivalents of N-hydroxysuccinimide, 1 to 1.2 molar equivalents of 1,3-dicyclohexylcarbodiimide and an anhydrous solvent (at about 1.2 mL/mmolar equivalent) such as tetrahydrofuran at a temperature in the range of about 0° C. to 10° C., preferably about 4° C. under an inert atmosphere for a period of about 13 to 39 hours, preferably about 26 hours. The resulting precipitate is removed by filtration. To the filtrate is added about 1.3 molar equivalents of a compound of Formula 6b dissolved in THF or in water, and if $R^4$ is —$CH(R^5)$—$CO_2H$, 1.3 molar equivalents of a strong base such as sodium hydroxide in water is also added. The combined mixture is stirred at about room temperature for a period of about 12 to 24 hours, preferably about 18 hours. The solid residue is removed by filtration and the filtrate is diluted with saturated aqueous $NaHCO_3$ and is extracted with a non-polar solvent (e.g., $CHCl_3$). If $R^4$ is lower-alkyl or aralkyl, the organic layer is evaporated to give the crude protected amino acid amide. If $R^4$ is —$CH(R^5)$—$CO_2H$, the aqueous layer is acidified and the resulting precipitate is collected, washed and dried to yield the crude protected dipeptide acid. The crude protected dipeptide acid is subjected again to the above procedure, using excess anhydrous ammonia in an anhydrous solvent such as tetrahydrofuran, to give the crude protected dipeptide amide.

The crude protected amino acid amide or crude protected dipeptide amide from this procedure is subjected to hydrogenolysis in methanol over 10% Pd/C. The product is purified by flash chromatography (e.g., ethyl acetate-methanol, 10:1) to afford a compound of Formula 6.

PREPARATION OF FORMULA 7

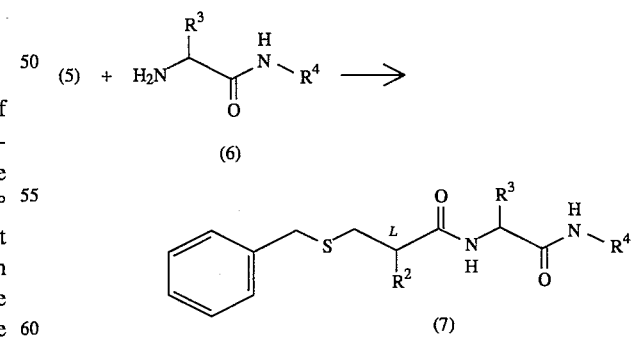

A compound of Formula 7 is formed by the following procedure, which is a modification of a procedure reported in Bodanszky, M.; Bodanszky, A. *The Practice of Peptide Synthesis;* Springer-Verlag: New York, 1984; p 145.

A compound of Formula 5 is combined with about 1 molar equivalent of a single amino acid amide or dipeptide derivative [i.e., a compound of Formula 6 where $R^3$ is hydrogen, methyl, 2-propyl, 2-methylpropyl, 2-butyl, blocked 4-aminobutyl, blocked 3-guanylpropyl, blocked 4-imidazoylmethyl, phenylmethyl, blocked 4-hydroxyphenylmethyl, 3-indolylmethyl, 4-methoxyphenylmethyl or phenethyl) and $R^4$ is lower-alkyl, aralkyl or —CH($R^5$)—C(O)NH$_2$ where $R^5$ is hydrogen, lower-alkyl, amino lower-alkyl, guanyl lower-alkyl, imidazoylalkyl, hydroxymethyl, 1-hydroxyethyl, mercapto loweralkyl, or methylthio lower-alkyl] 1-hydroxybenzotriazole (about 1–1.2 molar equivalents) and triethylamine in anhydrous 1,2-dimethoxyethane at about 0° C. To this solution is added dicyclohexylcarbodiimide (about 1–1.2 mmol). The reaction mixture is stirred at a temperature in the range of about 15°–30° C., preferably about room temperature for a period of about 12–24 h, preferably about 18 h. The reaction is worked up by removing the solvent, adding a nonpolar organic solvent, e.g., CH$_2$Cl$_2$, and filtering the mixture. The filtrate is evaporated and the residue purified by chromatography, e.g., flash chromatography on silica gel, to yield the desired benzyl-sulfide derivatized modified polypeptide, i.e., the compound of Formula 7.

PREPARATION OF FORMULA 8

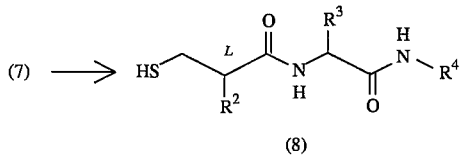

A compound of Formula 7 is debenzylated following a procedure using sodium in liquid ammonia (described in Evans, D. A.; Mathre, D. J.; Scott, W. L. *J. Org. Chem.* 1985, 50, 1830–1835). To a solution of the benzyl thioether in a nonpolar solvent such as, diethyl ether, THF, preferably THF and liquid NH$_3$, about 2–5 molar equivalents, preferably about 3.5 molar equivalents of elemental Na is added over a period of about 15 to 45 minutes, preferably about 30 minutes. The mixture is stirred for about an additional 10 min, solid NH$_4$Cl is added and the NH$_3$ is allowed to evaporate. The reaction mixture is partitioned and the aqueous layer is extracted. The combined organic layers are washed, dried, and evaporated. The residue is purified by chromatography, e.g., flash chromatography on silica gel, to yield the desired mercaptan derivatized polypeptide, i.e., the compound of Formula 8.

PREPARATION OF FORMULA 10

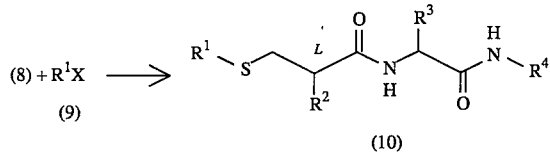

A compound of Formula 8 is added to a solution of elemental Na (about 1.1 molar equivalents) and methanol. To this solution is added about 1.5 molar equivalents of a lower-alkyl halide (i.e., a compound of Formula 9 where X is halo). The mixture is stirred for a period of about 4–8 hours, preferably about 6 hours at a temperature in the range of about 40° C. At the completion of the reaction, the solvent is removed, the residue partitioned and the aqueous layers extracted. The combined organic layers are dried and evaporated. The resultant residue is purified by chromatography, e.g., flash chromatography on silica gel, yielding the desired lower-alkyl sulfide polypeptide, i.e., the compound of Formula 10.

PREPARATION OF FORMULA 11

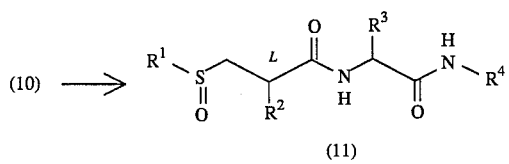

A compound of Formula 10 is dissolved in solvent, such as ethyl acetate, methylene chloride, methanol or combination of methylene chloride and methanol (preferably a combination of methylene chloride and methanol at about a 2:1 ratio). The solution is cooled to a temperature in the range of about 0° C. to –20° C., preferably about –10° C. To this solution is added about 1 molar equivalent of a strong oxidizing reagent, such as a peracid, sodium metaperiodate in methanol-water, t-butyl hypochlorite in methanol, hydrogen peroxide in water, acetone or acetic acid, or m-chloroperoxybenzoic acid preferably m-chloroperoxybenzoic acid. The reaction mixture is stirred for a period of about 4 to 12 hours, preferably about 8 hours. At completion of the reaction, the solvents are removed, the residue triturated, and the resultant residue purified by chromatography, e.g., flash chromatography on silica gel, to yield the desire sulfoxide derivatized polypeptide as a mixture of two diastereomers, i.e., the compound of Formula 11. The mixture is taken to the next step without further separating the two diastereomers.

PREPARATION OF FORMULA I

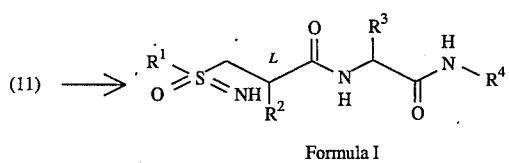

Formula I

A compound of Formula 11 (as a mixture of two diastereomers) is dissolved in a solvent, such as THF. To this solution is added about 3 molar equivalents of an amination reagent, such as O-mesitylsulfonylhydroxylamine. The reaction mixture is stirred at a temperature in the range of 20° C. to 30° C., preferably about 25° C., for a period of about 8 to 12 hours, preferably about 10 hours. At the completion of the reaction, the mixture is partitioned, and the pH is adjusted to about pH 9. The aqueous layer is extracted, the combined organic layers dried and then evaporated. The resultant residue is purified by chromatography, e.g., flash chromatography followed by preparative TLC on silica gel, to yield the desired sulfoximine compound as a mixture of two diastereomers, i.e., the compound of Formula I (where X and Y are O and NH).

REACTION SCHEME B

STARTING MATERIALS

The compounds of di-lower alkyl malonate and Formula 12A (where $R^2$ is methyl, 2-propyl, 2-methylpropyl, 2-butyl, phenylmethyl, blocked 4-hydroxyphenylmethyl, blocked 3-indoylmethyl, 4-methoxyphenylmethyl or phenethyl) are commercially available from the Aldrich Chemical Company, or can be prepared without undue experimentation by those of ordinary skill in the art.

PREPARATION OF FORMULA 12

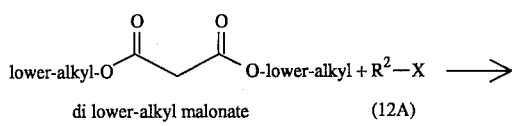

di lower-alkyl malonate     (12A)

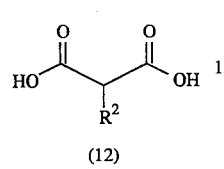

(12)

A solution of sodium ethoxide is formed by dissolving about 1 molar equivalent of sodium in absolute ethanol (about 500 mL/mole). To this solution is added about 1 molar equivalent of di lower-alkyl malonate, such as dimethylmalonate or diethylmalonate, preferably diethylmalonate with cooling under an inert atmosphere. To the resulting solution is added about 1 molar equivalent of a compound of Formula 12A where $R^2$ is lower-alkyl, aralkyl or heteroaralkyl and X is halo. The reaction mixture is refluxed under an inert atmosphere for a period of 7 to 21 hours, preferably about 14 hours. The ethanol is removed and the residue is partitioned between a non-polar organic solvent and water. The aqueous layer is extracted. The combined organic layers are combined, dried over a drying agent (e.g., $Na_2SO_4$) and evaporated. The residue is distilled to give a diethyl optionally substituted malonate.

The diethyl optionally substituted malonate is combined with 95% ethanol (about 1 mL/mmole). To this solution is added about 4 molar equivalent of KOH in 95% ethanol (about 12 mL/g). The reaction mixture is stirred at about room temperature (i.e., about 25° C.) for a period of about 8 to 24 hours, preferably about 16 hours, and then refluxed for a period of about 30 to 90 minutes, preferably about 1 hour. The mixture is cooled, diluted and extracted with a non-polar organic solvent. The aqueous layer is cooled to about 0° C., acidified to a pH<1 and extracted with a non-polar organic solvent. If neccessary, the aqueous layer is further continuously extracted for a period of about 18 hours. The organic layers are combined, dried over a drying agent (e.g., $Na_2SO_4$) and evaporated to afford the desired optionally substituted malonic acid, i.e., a compound of Formula 12.

PREPARATION OF FORMULA 13

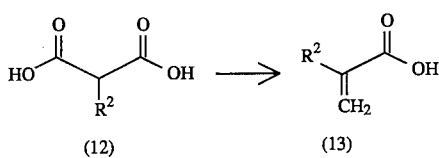

(12)     (13)

An optionally substituted malonic acid, i.e., a compound of Formula 12 is dissolved in enough 37% aqueous formalin to provide about 5 molar equivalents of formaldehyde. To this solution is added about 1 molar equivalent of a secondary amine base, such as diethylamine. The reaction mixture is stirred at a temperature in the range of about 20° C. to 30° C., preferably about room temperature, for a period of about 1 to 4 hours, preferably about 3 hours. The reaction mixture is then refluxed for a period of about 1 to 3 hours, preferably about 2 hours. The mixture is allowed to cool to about room temperature and diluted with a solvent such as methylene chloride, and extracted with a base, such as $NaHCO_3$. The aqueous layer is acidified and extracted. The organic layer is dried, (over a drying agent) and evaporated to yield the desired 2-optionally substituted 2-propenoic acid, i.e., the compound of Formula 13.

PREPARATION OF FORMULA 15

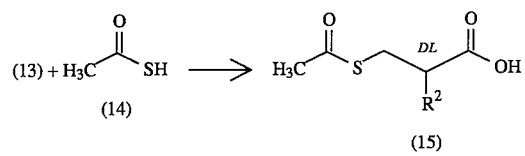

(14)     (15)

A compound of Formula 13 is combined with about 2 molar equivalents of thiolacetic acid (i.e., a compound of Formula 14) and stirred under an inert atmosphere for a period of about 20 to 32 hours, preferably about 26 hours. The excess thiolacetic acid is removed yielding the desired 2-optionally substituted 3-acetylthiopropanoic acid, i.e., the compound of Formula 15.

PREPARATION OF FORMULA 16

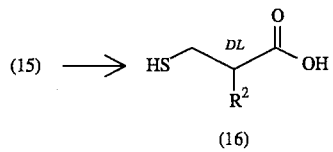

(16)

A compound of Formula 15 is combined with a strong base, such as concentrated $NH_4OH$, and stirred at a temperature in the range of about 20° C. to 30° C., preferably about room temperature for a period of about 30 to 90 minutes, preferably about 60 minutes. At the completion of the reaction, the mixture is acidified to a pH of about 4 to 5. The mixture is extracted with an organic solvent, such as, methylene chloride, and the organic layers are combined and evaporated yielding the desired 2-optionally substituted 3-mercapto propanoic acid, i.e., the compound of Formula 16.

PREPARATION OF FORMULA 17

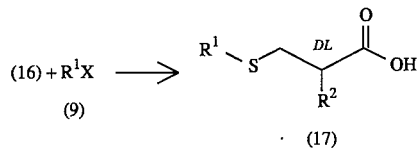

(9)     (17)

A compound of Formula 16 is dissolved in a solvent, such as methanol with about 2 molar equivalents of a base such as sodium methoxide. To the solution is added about 1.2 molar equivalents of a lower-alkyl or aralkyl halide (i.e., a compound of Formula 9 where X is halo). The solution is stirred for a period of about 4 to 12 hours, preferably about 8 hours at a temperature in the range of about 20° C. to 30° C., preferably about room temperature. Water is added to the solution followed by acidification and extraction. The organic layer is dried and evaporated yielding the desired lower-alkyl or aralkyl sulfide modified carboxylic acid, i.e., the compound of Formula 17.

PREPARATION OF FORMULA 18

(17) ⟶ 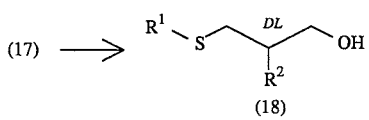

(18)

The compound of Formula 17 is dissolved in an aprotic solvent, such as tetrahydrofuran. A reducing reagent, such as 1M $BH_3$ in THF is added to the solution at about 0° C. in a gradual manner with stirring over a period of about 15 minutes. The solution is allowed to warm to about room temperature and stirred for a period of about 2 to 4 hours, preferably about 3 hours. The reaction mixture is cooled to a temperature in the range of 0° C. and quenched by the gradual addition of water. The mixture is partitioned, and the organic layer is washed and dried (over a drying agent). The solvent is removed and the residue is purified by chromatography, e.g., flash chromatography, to give the desired lower-alkyl sulfide 2-optionally substituted propanol, i.e., the compound of Formula 18.

PREPARATION OF FORMULA 19

(18) ⟶ 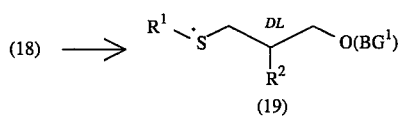

(19)

A compound of Formula 18 is dissolved in a solvent, such as DMF. To the solution is added about 2.3 molar equivalents of a base, such as imidazole and 1 molar equivalent of a blocking agent, such as, t-butyldimethylsilyl chloride. The reaction mixture is stirred at a temperature in the range of about 20° C. to 30° C., preferably about room temperature, for a period of about 5 to 9 hours, preferably about 7 hours. At the completion of the reaction, the mixture is partitioned and the organic layers are washed, dried and evaporated. The resultant residue is purified by chromatography, e.g., flash chromatography on silica gel, yielding the desired lower-alkyl sulfide 2-optionally substituted blocked propanol, i.e., the compound of Formula 19.

PREPARATION OF FORMULA 20

(19) ⟶ 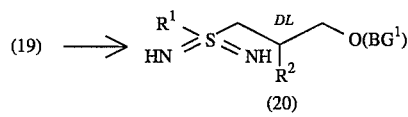

(20)

A diimine moiety is introduced into a compound of Formula 19 using a modification of the procedure described in Mock, W. L.; Tsay, J. T. *J. Am. Chem. Soc.* 1989, 111, 4467–4472. A solution is formed with a compound of Formula 19 in a solvent, such as tetrahydrofuran, diethyl ether, or acetonitrile, preferably acetonitrile, and about an equal volume of anhydrous liquid ammonia under an inert atmosphere at a temperature in the range of about –40° C. to –70° C., preferably about –55° C. To the solution is added about 2.5 molar equivalents of N-chlorosuccinimide or t-butylhypochlorite, preferably N-chlorosuccinimide in a solvent such as acetonitrile in a gradual manner. The reaction mixture is stirred for a period of about 15 to 45 minutes, preferably about 30 minutes, at a temperature in the range of about –40° C. to –70° C., preferably about –55° C. The mixture is allowed to warm to about room temperature and stirred for a period of about 12 to 24 hours, preferably about 18 hours. The solvent(s) is removed and the residue is partitioned. The organic layer is dried, and evaporated. The residue is purified by chromatography, e.g., flash chromatography, to yield the desired sulfodiimine modified derivative, i.e., the compound of Formula 20.

PREPARATION OF FORMULA 21

(20) ⟶ 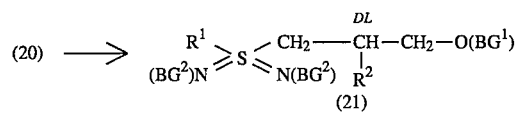

(21)

To a solution of the sulfodiimine (a compound of Formula 20) in a solvent, such as methylene chloride, diethyl ether or THF, preferably methylene chloride, is added about 5 molar equivalents of a base, such as pyridine, or triethylamine, preferably pyridine and about 4 molar equivalents of benzyl chloroformate. The mixture is stirred for a period of about 4 to 8 hours, preferably about 6 hours at a temperature in the range of about 20° to 30° C., preferably about room temperature. A base, such as $NaHCO_3$, is added to the mixture. The mixture is then extracted, the organic layer isolated and evaporated, and the residue chromatographed, e.g., flash chromatography on silica gel to yield the desired blocked diimine compound, i.e., the compound of Formula 21.

PREPARATION OF FORMULA 22

(21) ⟶ 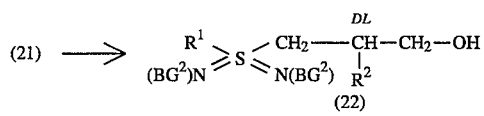

(22)

To a solution of the compound of Formula 21 in a solvent, such as diethyl ether, THF, methylene chloride, preferably THF, is added about 2 molar equivalents of a deblocking reagent, such as tetrabutylammonium fluoride hydrate. The reaction mixture is stirred for a period of about 1 to 4 hours, preferably about 2.5 hours, at a temperature in the range of 20° to 30° C., preferably about room temperature. At completion of the reaction, the mixture is diluted with an organic solvent, such as ethyl acetate and washed. The organic layer is dried, and evaporated. The residue is further purified by chromatography, e.g., flash chromatography on silica gel to yield the desired blocked diimine compound, i.e., Formula 22.

PREPARATION OF FORMULA 23

(22) ⟶ 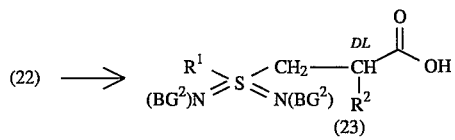

(23)

To a solution of the compound of Formula 22 (dissolved in a polar solvent, such as acetone, or methanol, preferably acetone) is added an oxidizing reagent, such as Jones' reagent, (i.e., an aqueous chromic acid solution) in a dropwise manner at a temperature in the range of about 0° C. with stirring. After completion of the addition, the mixture is stirred for a period of about 2 to 4 hours, preferably about 3 hours. The reaction mixture is poured into water and extracted. The organic layer is collected, dried and evaporated. The residue is purified by chromatography, e.g., flash chromatography on silica gel to give the desired blocked diimine modified amino acid, i.e., the compound of Formula 23.

PREPARATION OF FORMULA 24

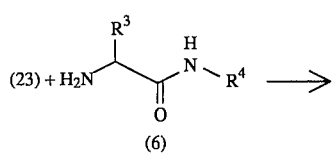

(6)

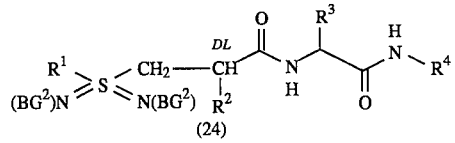

(24)

A compound of Formula 23 is coupled with a single amino acid amide, or a dipeptide derivative [i.e., a compound of Formula 6 where $R^3$ is hydrogen, methyl, 2-propyl, 2-methylpropyl, 2-butyl, blocked 4-aminobutyl, blocked 3-guanylpropyl, blocked 4-imidazoylmethyl, phenylmethyl, blocked 4-hydroxyphenylmethyl, 3-indolylmethyl, 4-methoxyphenylmethyl or phenethyl) and $R^4$ is lower-alkyl, aralkyl or —CH($R^5$)—C(O)NH$_2$ where $R^5$ is hydrogen, lower-alkyl, amino lower-alkyl, guanyl lower-alkyl, imidazoylalkyl, hydroxymethyl, 1-hydroxyethyl, mercapto lower-alkyl, or methylthio lower-alkyl] following the procedures described previously in Reaction Scheme A (Preparation of Formula 7).

PREPARATION OF FORMULA I

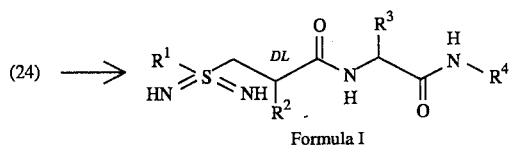

Formula I

A compound of Formula 24 is dissolved in a solvent, such as ethanol, or methanol, preferably ethanol. To the solution is added a hydrogenation catalyst, such as 10% Pd/C (palladium on carbon), a catalytic amount of an amine base (such as, cyclohexylamine). H$_2$ gas is bubbled through the solution for a period of about 2 to 4 hours, preferably about 3 hours. The mixture is filtered and the solids are washed. The filtrates are combined, evaporated and purified by chromatography, e.g., flash chromatography on silica gel to yield the desire diimine modified polypeptide compound, i.e., the compound of Formula I.

REACTION SCHEME C

PREPARATION OF FORMULA 25

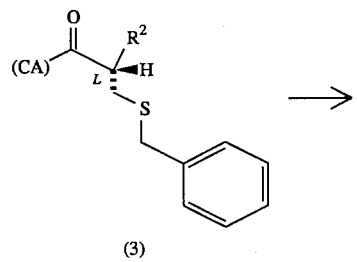

(3)

-continued

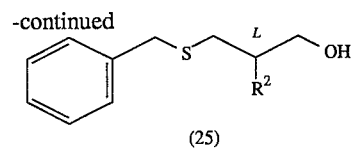

(25)

A compound of Formula 25 is prepared following the procedures described in Hollady, M. W.; Salituro, F. G.; Rich, D. H., *J. Med Chem.* 1987, 30, 374–383). About 1 molar equivalent of CaCl$_2$ and about 3.5 mL/mmolar equivalents of an alcoholic solvent, such as absolute EtOH are combined. The solution is stirred until the solid is dissolved and the solution is cooled to a temperature in the range of about −10° C. to 10° C., preferably about 0° C. To the solution is added about 2 molar equivalents of a reducing agent, preferably NaBH$_4$, and the solution is stirred for about 0.5 h. To the solution, is added a compound of Formula 3 (prepared as described in Reaction A) in a solvent, such as THF or diethyl ether, preferably THF (about 1.0 mL/mmolar equivalent) in a gradual manner. Upon completion of the addition, the reaction mixture is stirred at a temperature in the range of about −10° C. to 10° C., preferably about 0° C. under an inert atmosphere for a period of about 2 to 6 hours, preferably about 4 hours. The reaction mixture is quenched with an organic solvent (e.g., EtOAc), followed by aqueous solutions (e.g., water followed by acetic acid) and acidified to a pH of about 2. The aqueous layer is extracted with an organic solvent (e.g., EtOAC), the organic layers are combined, washed, dried and evaporated yielding the desired enantiomerically pure optionally substituted benzylthioether alcohol, i.e., the compound of Formula 25.

PREPARATION OF FORMULA 26

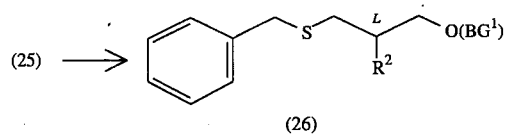

(26)

A compound of Formula 25 is dissolved in a solvent, such as DMF. To the solution is added about 2.3 molar equivalents of a base, such as imidazole and 1 molar equivalent of a blocking agent, such as, t-butyldimethylsilyl chloride. The reaction mixture is stirred at a temperature in the range of about 20° C. to 30° C., preferably about room temperature, for a period of about 5 to 9 hours, preferably about 7 hours. At the completion of the reaction, the mixture is partitioned and the organic layers are washed, dried and evaporated. The resultant residue is purified by chromatography, e.g., flash chromatography on silica gel, yielding the desired benzylthioether 2-optionally substituted blocked propanol, i.e., the compound of Formula 26.

PREPARATION OF FORMULA 27

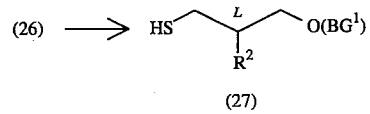

(27)

A compound of Formula 26 is debenzylated following a procedure using sodium in liquid ammonia (described in Evans, D. A.; Mathre, D. J.; Scott, W. L. *J. Org. Chem.* 1985, 50, 1830–1835). To a solution of the benzylthioether in a nonpolar solvent such as, diethyl ether, THF, preferably THF and liquid NH₃, about 2–5 molar equivalents, preferably about 3.5 molar equivalents of elemental Na is added over a period of about 15 to 45 minutes, preferably about 30 minutes. The mixture is stirred for about an additional 10 min, solid NH₄Cl is added and the NH₃ is allowed to evaporate. The reaction mixture is partitioned and the aqueous layer is extracted. The combined organic layers are washed, dried, and evaporated. The residue is purified by chromatography, e.g., flash chromatography on silica gel, to yield the desired mercaptan blocked alcohol, i.e., the compound of Formula 27.

PREPARATION OF FORMULA 28

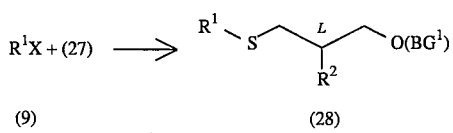

About 100 molar equivalents of NaOMe (e.g., 25 mL of 0.106M NaOMe) in a solvent, such as MeOH, is added in a gradual manner to a compound of Formula 27 in a solvent, such as MeOH (about 4 mL/mmolar equivalents). To this solution is added about 1.1 molar equivalents of a lower-alkyl halide (i.e., a compound of Formula 9 where X is halo). The reaction mixture is allowed to stand for a period of about 12 to 24 hours, preferably about 18 hours at a temperature in the range of about 20° C. to 30° C., preferably about room temperature. The mixture is diluted and acidified. The aqueous layer is extracted with an organic solvent (e.g., CH₂Cl₂). The organic extract is dried, evaporated and purified by chromatography (e.g., flash chromatography on silica gel) yielding the desired lower-alkyl sulfide 2-optionally substituted blocked propanol, i.e., the compound of Formula 28.

PREPARATION OF FORMULA 29

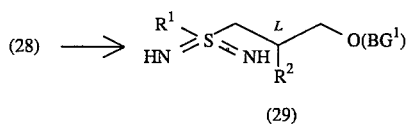

By following the procedures described in Reaction Scheme B, Preparation of Formula 20 (e.g., Example 17) the desired enantiomerically pure sulfodiimine modified derivative, i.e., the compound of Formula 29 is obtained.

PREPARATION OF FORMULA 30

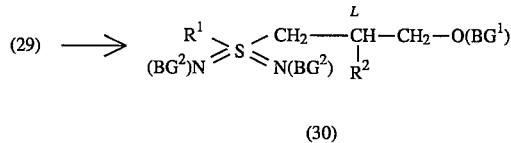

By following the procedures described in Reaction Scheme B, Preparation of Formula 21 (e.g., Example 18) the desired enantiomerically pure blocked diimine compound, i.e., the compound of Formula 30 is obtained.

PREPARATION OF FORMULA 31

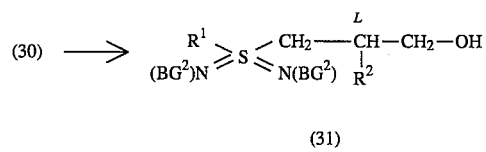

By following the procedures described in Reaction Scheme B, Preparation of Formula 22 (e.g., Example 19) the desired enantiomerically pure blocked diimine compound i.e., the compound of Formula 31 is obtained.

PREPARATION OF FORMULA 32

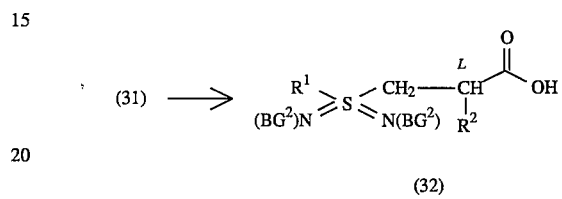

By following the procedures described in Reaction Scheme B, Preparation of Formula 23 (e.g., Example 20) the desired enantiomerically pure blocked diimine modified amino acid, i.e., the compound of Formula 32 is obtained.

PREPARATION OF FORMULA 33

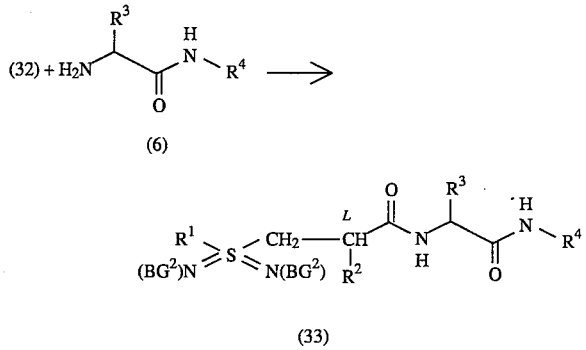

By following the procedures described in Reaction Scheme B, Preparation of Formula 24 (e.g., Example 21) the desired enantiomerically pure blocked diimine modified polypeptide compound, i.e., the compound of Formula 33 is obtained.

PREPARATION OF FORMULA I

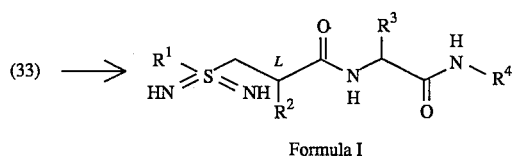

Formula I

By following the procedures described in Reaction Scheme B, Preparation of Formula I (e.g., Example 22), the desired enantiomerically pure diimine modified polypeptide compound, i.e., the enantiomerically pure compound of Formula I is obtained.

PREFERRED COMPOUNDS

Presently preferred is the compound of Formula I where $R^1$ is lower-alkyl.

Especially preferred is the compound of Formula I where $R^1$ is methyl.

Also especially preferred is the compound of Formula I where $R^1$ is n-butyl.

Of the compound where $R^1$ is methyl, most preferred is the compound of Formula I where $R^2$ is 2-methylpropyl, particularly where the carbon that is the point of attachment for $R^2$ is in the L-configuration.

Of the compound where $R^1$ is n-butyl, most preferred is the compound of Formula I where $R^2$ is 2-methylpropyl, particularly where the carbon that is the point of attachment for $R^2$ is in the L-configuration.

Of the compound where $R^1$ is n-butyl, most preferred is the compound of Formula I where $R^2$ is 4-methoxyphenylmethyl, particularly where the carbon that is the point of attachment for $R^2$ is in the L-configuration.

UTILITY, TESTING AND ADMINISTRATION

GENERAL UTILITY

The compounds of this invention, including the pharmaceutically acceptable esters, ethers, or salts thereof, and the compositions containing them are useful for modulating physiological functions or treating diseases and disease conditions associated with the modulation of MMP activity, e.g., arthritic diseases, such as osteoarthritis (OA), rheumatoid arthritis (RA), septic arthritis, soft tissue rheumatism, polychondritis and tendonitis; tumor invasion in certain cancers, periodontal diseases; corneal ulceration, e.g., that induced by alkali or other burns, by radiation, by vitamin E or retinoid deficiency; glomerular diseases, such as proteinuria, dytrophobic epidermolysis bullosa; bone resorption diseases, such as osteoporosis, Paget's disease, hyperparathyroidism and cholesteatoma; birth control through preventing ovulation or implantation; angiogenesis relating to tumor growth on to the neovascularization associated with diabetic retinopathy and macular degeneration; coronary thrombosis associated with atherosclerotic plaque rupture; and pulmonary emphysema.

The compounds of this invention inhibit MMP, thereby providing a means of controlling conditions (normal physiological or disease states) modulated or mediated by MMP, particularly those where elevated levels of MMP have been detected.

All forms of arthritis (i.e., arthritic diseases soft tissue rheumatism, polychondritis and tendonitis) are characterized by the erosion of the articular cartilage of affected joints. Since cartilage consists primarily of proteoglycans and type II collagen, proteinases capable of attacking both macromolecules have been implicated in the progression of the diseases [Harris et al., (1969) *Arthritis Rheum.* 12, 92–102; Harris et al., (1970) *Arthritis Rheum.* 13, 83–95; Woolley et al., (1977) *Arthritis Rheum.* 20, 1231–1239; and Krane, S. M., (1981) *Ann. Rheum.* Dis. 40, 433–448].

The metastasis of tumor cells is a process that is inhibited by the connective tissue barriers of the host. The association of both interstitial collagenases and proteinases capable of degrading type IV collagen found in basement membrane is well documented and is believed to facilitate metastasis [Strauli et al., (1980) *Proteinases and Tumor Invasion*, Raven Press, New York; Liotta et al., (1991) *Tumor Invasion and Metastasis*, pp. 319–333, Martinus Nijhoff, Dordrecht; Blood, C. H. and Zetter, B. R., (1990) *Biochim. Biophys. Acta* 1032, 89–118; Liotta et al., (1983) Lab. Invest. 49, 636–649; and Liotta et al., (1980) Nature (London) 284, 67–68].

Periodontal disease is an inflammatory disease that is triggered by bacteria that inhabit the gingival cavity. Periodontis is characterized by the progressive loss of the attachment apparatus of teeth. Since the major protein component of gingival tissue and bone is type I collagen, collagenases are believed to participate in the progression of the disease [Robertson, P. B. and simpson, J. (1976) *J. Periodontol.*, 47, 29–33; and Birkedal-Hansen, H., (1980) in *Collagenases in Normal and Pathological Connective Tissue*, (Woolley, D. E. and Evanson, J. M., eds), pp. 127–140, Wiley and Sons, New York].

Corneal ulceration can be brought about by chemical or thermal burns, infections Stevens-Johnson syndrome, Mooren's ulcer, vitamin A deficiency, and many other diseases. The corneal stroma is composed predominantly of type I collagen that is progressively degraded during ulceration [Van Wart, H. E. and Mookhtiar, K. A. (1990) in *Biological Response Modifiers for Tissue Repair* (Grotendorst, G., Jhelmeland, L. M. and Gills, J. P., eds), pp. 23–50, Portfolio, The Woodlands, Tex.; Brown et al., (1969) *Arch. Ophthalmol.* 81, 370–373; and Berman, M. B. (1980) in *Collagenases in Normal and Pathological Connective Tissue*, (Woolley, D. E. and Evanson, J. M., eds), pp. 141–174, Wiley and Sons, New York].

Glomerular diseases, such as proteinuria, dytrophobic epidermolysis bullosa, which a separation of the dermis and epidermis, are believed to be influenced by collagenases [Eisen, A. Z. (1969) *J. Invest. Dermatol.* 52, 449–453].

Bone resorption diseases., such as osteoporosis, Paget's disease, hyperparathyroidism and cholesteatoma, are believed to involve the action of collagenases [Vaes, G. (1980) in *Collagenases in Normal and Pathological Connective Tissue*, (Woolley, D. E. and Evanson, J. M., eds), pp. 185–207, Wiley and Sons, New York; Gardner et al., (1971) *Surg. Forum*, 22,435–437; Abramson, M. (1969) *Ann. Otol. Rhinol. Laryngol.*, 78, 112–124; Sakamoto et al., (1975) *Biochem. Biophys. Res. Commun.* 63, 172–177; Griffith et al., (1965) *J. Am. Med. Assoc.* 193, 91–94; and Eeckhout et al., (1986) *Biochem. J.* 239 793–796].

Certain MMP have been reported as mediating ovulation and implantation, thus inhibition of these MMP would provide a means of birth control [Librach et al., *J. Cell Biol.*, 13, 437–449, 1991; and Brännström et al., *Endocrinology*, 122, 5, 1715–1721, 1988].

Certain MMP have been associated with angiogenesis relating to tumor growth or to the neovascularization associated with diabetic retinopathy and macular degeneration. Inhibition of these MMP would provide a means of slowing or halting the development of such conditions [Moses et al., *Bio/technology*, 9, 630–634, 1991; and Langer et al., Proc. Natl. Aca. Sci. USA, 77, 7, 4331–4335, 1980)].

MMP have been linked with coronary thrombosis caused by atherosclerotic plaque rupture [Henney et al., *Proc. Natl. Acad. Sci.*, 88, 8154–8158, 1991]. Inhibition of MMP could alleviate this condition.

Interstitial collagenase has been implicated as a possible etiological agent in the emphysema disease process. Although elastase has been proposed as the primary enzyme responsible for emphysematous lung damage, there is evidence that other extra-ceullular matrix proteases could play a role in emphysema [D'Armiento et al., *Cell*, 71, 955–961 Dec. 11, 1992].

TESTING

The potency and selectivity of compounds of the present invention as inhibitors of MMP are determined by assay against MMPs that are associated with the metabolic turnover of interstitial collagens in the extracellular matrix of humans. For example, following the procedures described in Example 21, or modifications thereof.

Five types of MMP are assayed, i.e., fibroblast-type collagenase (HFC), gelatinase (HFG) and stromelysin (HFS) and neutrophil-type collagenase (HNC) and gelatinase (HNG).

The assay method is based on the hydrolysis of DNP-Pro-Leu-Ala-Leu-Trp-Ala-Arg as the substrate (according to Netzel-Arnett, S.; Mallya, S. K.; Nagase, H.; Birkedal-Hansen, H.; Van Wart, H. E. *Anal. Biochem.* 1991, 195, 86–92).

ADMINISTRATION

The compounds of this invention are administered at a therapeutically effective dosage, i.e., that amount which, when administered to a mammal in need thereof, is sufficient to effect treatment, as described above (for example, to reduce or otherwise treat inflammation, pain and/or pyrexia in the mammal). Administration of the active compounds and salts described herein can be via any of the accepted modes of administration for agents that serve similar utilities.

The level of the drug in a formulation can vary within the full range employed by those skilled in the art, e.g., from about 0.01 percent weight (% w) to about 99.99% w of the drug based on the total formulation and about 01% w to 99.99% w excipient. Preferably the drug is present at a level of about 10% w to about 70% w.

Generally, an acceptable daily dose is of about 0.001 to 50 mg per kilogram body weight of the recipient per day, preferably about 0.05 to 25 mg per kilogram body weight per day, and most preferably about 0.01 to 10 mg per kilogram body weight per day. Thus, for administration to a 70 kg person, the dosage range would be about 0.07 mg to 3.5 g per day, preferably about 3.5 mg to 1.75 g per day, and most preferably about 0.7 mg to 0.7 g per day depending upon the individuals and disease state being treated. Such use optimization is well within the ambit of those of ordinary skill in the art.

Administration can be via any accepted systemic or local route, for example, via parenteral, oral (particularly for infant formulations), intravenous, nasal, bronchial inhalation (i.e., aerosol formulation), transdermal or topical routes, in the form of solid, semi-solid or liquid dosage forms, such as for example, tablets, suppositories, pills, capsules, powders, solutions, suspensions, aerosols, emulsions or the like, preferably in unit dosage forms suitable for simple administration of precise dosages. The compositions will include a conventional pharmaceutical carrier or excipient and an active compound of Formula I and, in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in *"Remington's Pharmaceutical Sciences"* by E. W. Martin.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this invention are generally administered as a pharmaceutical composition which comprises a pharmaceutical excipient in combination with a compound of Formula I. The level of the drug in a formulation can vary within the full range employed by those skilled in the art, e.g., from about 0.01 percent weight (% w) to about 99.99% w of the drug based on the total formulation and about 0.01% w to 99.99% w excipient. Preferably, the formulation will be about 3.5 to 60% by weight of the pharmaceutically active compound, with the rest being suitable pharmaceutical excipients.

INTRAVENOUS ADMINISTRATION

Intravenous injection has proven to be an important route of administration for therapeutic agents. The compounds of the present invention can be administered via this route, for example, by dissolving the compound, ester, ether or salt in a suitable solvent (such as water or saline) or incorporation in a liposomal formulation followed, by dispersal into an acceptable infusion fluid. A typical daily dose of a compound of the invention can be administered by one infusion, or by a series of infusions spaced over periodic intervals.

ORAL ADMINISTRATION

Oral administration can be used to deliver the compound of Formula I using a convenient daily dosage regimen which can be adjusted according to the degree of affliction or for renal impairment, or to compensate for the toxic effects of other medications administered contemporaneously. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like. Such compositions may contain between 0.01 wt/wt % and 99.99 wt/wt % of the compound of Formula I, but preferably such compositions will contain between 25 wt/wt % and about 80 wt/wt %.

Preferably the compositions will take the form of a capsule, pill or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, polyvinylpyrrolidone, gum acacia, gelatin, cellulose and derivatives thereof, and the like. For oral administration to infants, a liquid formulation (such as a syrup or suspension) is preferred.

LIPOSOMAL FORMULATIONS

Pharmaceutical formulations based on liposomes have recently reached human clinical trials. Their benefits are believed related to favorable changes in tissue distribution and pharmacokinetic parameters that result from liposome entrapment of drugs, and may be applied to the compounds of the present invention by those skilled in the art.

The formulations can be designed to either target drug to disease sites [see: Lopez-Berestein et al., *J. Infect. Dis.*, 151:704–710 (1985); Gotfredsen et al., *Biochemical Pharmacology*, 32:3389–3396 (1983)]; or to the reticuloendothelial system [see Eppstein et al., *Int. J. Immunotherapy*, 2:115–126 (1986)], to increase duration of drug action [see: Gabizon et al., *Cancer Res.*, 42:4734 (1982); Eppstein et al., *Delivery Systems for Peptide Drugs*, Eds. S. S. Davis, L. Illum and E. Tomlinson, Plenum Pub. Corp., New York, pp. 277–283; C. A. Hunt, *Biochemica et Biophysica Acta.*, 719:450–463 (1982); and Senior et al., *Biochemica et Bio-* physica Acta., 839:1–8 (1985)], or to divert a drug away from organs that are particularly sensitive to its toxic effects [see: Weinstein et al., Pharmac. Ther., 24:207–233 (1983); Olson et al., Eur. J. Cancer Clin. Oncol., 18:167–176 (1982); and Gabzion et al., supra.].

Controlled release liposomal liquid pharmaceutical formulations for injection or oral administration are described in U.S. Pat. No. 4,016,100. Liposomal applications for oral drug delivery of a lyophilized liposome/peptide drug mixture filled into intestine capsules have also been suggested, see U.S. Pat. No. 4,348,384. The foregoing are incorporated herein by reference.

SUPPOSITORIES

For systemic administration via suppository, traditional binders and carriers include, for example, polyalkaline glycol or triglycerides [e.g., PEG 1000 (96%) and PEG 4000 (4%)]. Such suppositories may be formed from mixtures containing active ingredients in the range of from about 0.5 wt/wt % to about 10 wt/wt %; preferably from about 1 wt/wt % to about 2 wt/wt %.

LIQUIDS

Liquid pharmaceutically administrable compositions can, for example, be prepared by dissolving, dispersing, etc. an active compound (about 0.5% to about 20%), as described above, and optional pharmaceutical adjuvants in a carrier, such as, for example, water, saline, aqueous dextrose, glycerol, ethanol and the like, to thereby form a solution or suspension.

Actual methods of preparing such dosage forms are known, or will be apparent, to those skilled in this art; for example, see *Remington's Pharmaceutical Sciences*, Mack Publishing Company, Easton, Pa., 16th Ed., 1980. The composition to be administered will, in any event, contain a quantity of the active compound(s) in a pharmaceutically effective amount for relief of the particular condition being treated in accordance with the teachings of this invention.

EXAMPLES

The following examples are given to enable those skilled in the art to more clearly understand and to practice the present invention. They should not be considered as limiting the scope of the invention, but merely as being illustrative and representative thereof.

EXAMPLE 1

PREPARATION OF (4S, 5R)-3-(1-OXO-4-METHYLPENTYL)-4-METHYL-5-PHENYL-2-OXAZOLIDINONE

1A. Formula 2 Where $R^2$ Is 2-Methylpropyl

To a solution of (4S,5R)-4-methyl-5-phenyl-2-oxazolidinone (9.7 g) [prepared according to the procedures in Evans, D. A.; Mathre, D. J.; Scott, W. L. *J. Org. Chem.* 1985, 50, 1830–1835] in 100 mL of THF cooled to −78° C. with stirring, was added 35.6 mL of n-butyllithium (1.6M in hexane) until the orange-red color of the di-anion just persisted. The reaction mixture was then treated with 7.0 mL (7.7 g) of distilled 4-methylpentanoyl chloride, warmed to 0° C. and stirred for 30 min. Then 20 mL of 1M aqueous $K_2CO_3$ was added and the resultant two-phase mixture was stirred at 25° C. for 1 h. The organic solvents were evaporated in vacuo and the residue was extracted twice with $CH_2Cl_2$. The combined organic extract was washed with water and brine, then was dried over $Na_2SO_4$ and evaporated. The residue was subjected to flash chromatography on silica gel (hexane-EtOAc) to give 14.5 g (97% yield) of (4S,5R)-3-(1-oxo-4-methylpentyl)-4-methyl-5-phenyl-2-oxazolidinone as a solid. Characteristic analytical data are as follows: mp 76°–77° C. (hexane/EtOAc); $^1$H NMR (300 MHz, $CDCl_3$) δ7.30–7.46 (m, 5H), 5.67 (d, J=8 Hz, 1H), 4.77 (p, J=7 Hz, 1H), 2.88–3.05 (m, 2H), 1.53–1.69 (m, 3H), 0.94 (d, J= 7 Hz, 6H), 0.90 (d, J=7 Hz, 3H); $[\alpha]^{25}_D$ −33° (c=1.07, $CH_2Cl_2$).

1B. Formula 2 Varying $R^2$

By following the procedures described in Example 1A and substituting 4-methylpentanoyl chloride with other compounds of Formula 1 (where the $R^2$ substituents are as indicated in the table below) there are obtained the corresponding substituted compounds of Formula 2.

Formula 2

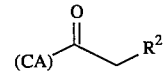

where (CA) is
(4S, 5R)-4-methyl-5-phenyl-2-oxazolidinone

| $R^2$ | Name |
| --- | --- |
| methyl | (4S,5R)-3-(1-oxo-propyl)-4-methyl-5-phenyl-2-oxazolidinone |
| 2-propyl | (4S,5R)-3-(1-oxo-3-methylbutyl)-4-methyl-5-phenyl-2-oxazolidinone |
| 2-butyl | (4S,5R)-3-(1-oxo-3-methylpentyl)-4-methyl-5-phenyl-2-oxazolidinone |
| benzyl | (4S,5R)-3-(1-oxo-3-phenylpropyl)-4-methyl-5-phenyl-2-oxazolidinone |
| blocked 4-hydroxyphenyl-methyl | (4S,5R)-3-[1-oxo-3-(4-hydroxyphenyl)propyl]-4-methyl-5-phenyl-2-oxazolidinone |
| blocked 3-indolyl-methyl | (4S,5R)-3-[1-oxo-3-(3-indolyl)propyl]-4-methyl-5-phenyl-2-oxazolidinone |
| 4-methoxyphenyl-methyl | (4S,5R)-3-[1-oxo-3-(4-methoxyphenyl)propyl]-4-methyl-5-phenyl-2-oxazolidinone |
| phenylethyl | (4S,5R)-3-(1-oxo-4-phenylbutyl)-4-methyl-5-phenyl-2-oxazolidinone |
| blocked 4-amino-butyl | (4S,5R)-3-(1-oxo-6-aminohexyl)-4-methyl-5-phenyl-2-oxazolidinone |
| blocked 3-guanyl-propyl | (4S,5R)-3-(1-oxo-5-guanylpentyl)-4-methyl-5-phenyl-2-oxazolidinone |
| blocked 4-imidazoylmethyl | (4S,5R)-3-[1-oxo-3-(4-imidazoyl)propyl]-4-methyl-5-phenyl-2-oxazolidinone |
| methylthioethyl | (4S,5R)-3-[1-oxo-4(methylthio)butyl]-4-methyl-5-phenyl-2-oxazolidinone |

EXAMPLE 2

PREPARATION OF (4S, 5R)-3-[(2S)-1-OXO-2-((BENZYLTHIO)METHYL)-4-METHYLPENTYL]-4-METHYL-5-PHENYL-2-OXAZOLIDINONE

2A. Formula 3 Where $R^2$ Is 2-Methylpropyl

A solution of lithium diisopropylamide was prepared from 1.96 mL (1.42 g) of diisopropylamine and 7.6 mL of n-butyllithium (1.75M in hexane) in 14 mL of THF. The solution was cooled to −78° C. with stirring, combined with a solution of (4S, 5R)-3-(1-oxo-4-methylpentyl)-4-methyl-5-phenyl-2-oxazolidinone (3.50 g) in THF (14 mL) and stirred for 30 min at −78° C. To this mixture was added 2.1 mL (3.1 g) of benzyl bromomethyl sulfide. The reaction mixture was stirred for 2 h at −25° C. and for 2 h at 0° C. Aqueous $NH_4Cl$ solution was added to the mixture. The organic solvents were removed in vacuo and the residue was extracted twice with $CH_2Cl_2$. The combined organic extract was washed twice with 1M aqueous NaHSO$_4$, then with saturated NaHCO$_3$, brine, dried over Na$_2$SO$_4$ and evaporated. The residue was subjected to flash chromatography on silica gel (hexane-EtOAc) to give 5.0 g (96% yield) of (4S, 5R)-3-[(2S)-1-oxo-2-((benzylthio)methyl)-4-methylpentyl]-4-methyl-5-phenyl-2-oxazolidinone as a clear oil. Characteristic analytical data are as follows: $^1$H NMR (300 MHz, CDCl$_3$) δ7.24–7.47 (m, 10H), 5.66 (d, J=7 Hz, 1H), 4.81 (p, J=7 Hz, 1H), 4.31–4.36 (m, 1H), 3.80 (AB q, J=13 Hz, 2H), 2.72 (dd, J=9, 14 Hz, 1H), 2.52 (dd, J=5, 14 Hz, 1H), 1.35–1.71 (m, 3H), 0.89–0.95 (m, 9H); $[\alpha]^{25}_D$ –91° (c=2.60, CH$_2$Cl$_2$)

2B. Formula 3 Varying R$^2$

By following the procedures described in Example 2A and substituting (4S, 5R)-3-(1-oxo-4-methylpentyl)-4-methyl-5-phenyl-2-oxazolidinone with other compounds of Formula 2 (where the R$^2$ substituents are as indicated in the table below) there are obtained the corresponding substituted compounds of Formula 3.

Formula 3

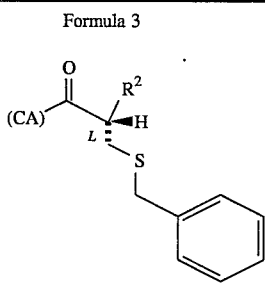

where (CA) is
(4S, 5R)-4-methyl-5-phenyl-2-oxazolidinone

| R$^2$ | Name |
|---|---|
| methyl | (4S,5R)-3-{(2S)1-oxo-2-[(benzylthio)methyl]-propyl}-4-methyl-5-phenyl-2-oxazolidinone |
| 2-propyl | (4S,5R)-3-{(2S)1-oxo-2-[(benzylthio)methyl]-3-methylbutyl}-4-methyl-5-phenyl-2-oxazolidinone |
| 2-butyl | (4S,5R)-3-{(2S)1-oxo-2-[(benzylthio)methyl]-3-methylpentyl}-4-methyl-5-phenyl-2-oxazolidinone |
| benzyl | (4S,5R)-3-{(2S)1-oxo-2-[(benzylthio)methyl]-3-phenylpropyl}-4-methyl-5-phenyl-2-oxazolidinone |
| blocked 4-hydroxyphenyl-methyl | (4S,5R)-3-{(2S)1-oxo-2-[(benzylthio)methyl]-3-(4-hydroxyphenyl)propyl}4-methyl-5-phenyl-2-oxazolidinone |
| blocked 3-indolyl-methyl | (4S,5R)-3-{(2S)1-oxo-2-[(benzylthio)methyl]-3-(3-indolyl)propyl}-4-methyl-5-phenyl-2-oxazolidinone |
| 4-methoxy-phenylmethyl | (4S,5R)-3-{(2S)1-oxo-2-[(benzylthio)methyl]-3-(4-methoxyphenyl)propyl}-4-methyl-5-phenyl-2-oxazolidinone |
| phenylethyl | (4S,5R)-3-{(2S)1-oxo-2-[(benzylthio)methyl]-4-phenylbutyl}-4-methyl-5-phenyl-2-oxazolidinone |
| blocked 4-amino-butyl | (4S,5R)-3-{(2S)1-oxo-2-[(benzylthio)methyl]-6-aminohexyl}-4-methyl-5-phenyl-2-oxazolidinone |
| blocked 3-guanyl-propyl | (4S,5R)-3-{(2S)1-oxo-2-[(benzylthio)methyl]-5-guanylpentyl}-4-methyl-5-phenyl-2-oxazolidinone |
| blocked 4-imida-zoylmethyl | (4S,5R)-3-{(2S)1-oxo-2-[(benzylthio)methyl]-3(4-imidazoyl)propyl}-4-methyl-5-phenyl-2-oxazolidinone |
| methylthioethyl | (4S,5R)-3-{(2S)1-oxo-2-[(benzylthio)methyl]-4-(methylthio)butyl}-4-methyl-5-phenyl-2-oxazolidinone |

EXAMPLE 3

PREPARATION OF BENZYL (2S)-2-[(BENZYLTHIO)METHYL]-4-METHYLPENTANOATE

3A. Formula 4 Where R$^2$ Is 2-Methylpropyl A solution of lithium benzyloxide was prepared by combining 2.5 mL (2.63 g) of benzyl alcohol with 50 mL of THF and 10.4 mL of n-butyllithium (1.75M in hexane). This solution was combined with 5.0 g of (4S, 5R)-3-[(2S)-1-oxo-2-[(benzylthio)methyl]-4-methylpentyl]-4-methyl-5-phenyl-2 -oxazolidinone in 12 mL of THF over 30 min with stirring at −10° C. The reaction mixture was warmed to 0° C. and stirred for 1.5 h. It was then quenched by addition of half-saturated aqueous NH$_4$Cl. The organic solvents were removed by evaporation in vacuo and the residue was extracted twice with CH$_2$Cl$_2$. The combined organic extract was washed with water and brine, dried over Na$_2$SO$_4$ and evaporated. The residue was subjected to flash chromatography on silica gel (hexane-EtOAc) to give 3.4 g (82% yield) of benzyl (2S)-2-[(benzylthio)methyl]-4-methylpentanoate as an oil. Characteristic analytical data are as follows: $^1$H NMR (300 MHz, CDCl$_3$) δ 7.23–7.39 (m, 10H), 5.15 (AB q, J=13 Hz, 2H), 3.69 (s, 2H), 2.63–2.69 (m, 2H), 2.47–2.52 (m, 1H), 1.26–1.58 (m, 3H), 0.86 (d, J=8 Hz, 3H), 0.84 (d, J=9 Hz, 3H).

3B. Formula 4 Varying R$^2$

By following the procedures described in Example 3A and substituting (4S, 5R)-3-[(2S)-1-oxo-2-[(benzylthio)methyl]-4-methylpentyl]-4-methyl-5 -phenyl-2-oxazolidinone with other compounds of Formula 3 (where the R$^2$ substituents are as indicated in the table below) there are obtained the corresponding substituted compounds of Formula 4.

Formula 4

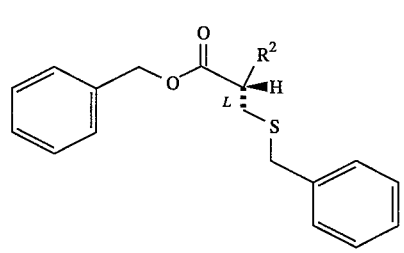

| R$^2$ | Name |
|---|---|
| methyl | benzyl (2S)-2-[(benzylthio)methyl] proprionate |
| 2-propyl | benzyl (2S)-2-[(benzylthio)methyl]-3-methyl-butanoate |
| 2-butyl | benzyl (2S)-2-[(benzylthio)methyl]-3-methylpentanoate |
| benzyl | benzyl (2S)-2-[(benzylthio)methyl]-3-phenylproprionate |
| blocked 4-hydroxy-phenylmethyl | benzyl (2S)-2-[(benzylthio)methyl]-3-(4-hydroxyphenyl)proprionate |
| blocked 3-indolylmethyl | benzyl (2S)-2-[(benzylthio)methyl]-3-(3-indolyl)-proprionate |
| 4-methoxy-phenylmethyl | benzyl (2S)-2-[(benzylthio)methyl]-3-(4-methoxyphenyl)proprionate |
| phenylethyl | benzyl (2S)-2-[(benzylthio)methyl]-4-phenylbutanoate |
| blocked 4-amino-butyl | benzyl (2S)-2-[(benzylthio)methyl]-6-aminohexanoate |
| blocked 3-guanyl-propyl | benzyl (2S)-2-[(benzylthio)methyl]-5-guanylpentanoate |
| blocked 4-imida-zoylmethyl | benzyl (2S)-2-[(benzylthio)methyl]-3-(4-imidazoyl)proprionate |

-continued

Formula 4

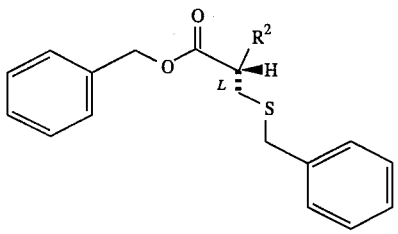

| R² | Name |
|---|---|
| methylthioethyl | benzyl (2S)-2-[(benzylthio)methyl]-4-(methylthio)butanoate |

EXAMPLE 4

PREPARATION OF BnS-(CH₂-L-Leu)-OH

4A. Formula 5 Where R² Is 2-Methylpropyl

A solution of 3.4 g of benzyl (2S)-2-[(benzylthio)methyl]-4-methylpentanoate in 10 mL of a 30% solution of anhydrous hydrogen bromide in glacial acetic acid was stirred at 50° C. for 30 min. The reaction mixture was cooled to room temperature, diluted with 20 mL of water and extracted twice with CH₂Cl₂. The combined extracts were evaporated under reduced pressure. The residue was dissolved in 50 mL of toluene and the solution was again evaporated. This procedure was repeated 2 more times in order to remove acetic acid. The crude product was dissolved in 1M aqueous KOH and extracted with ether. The aqueous layer was acidified to pH 1 with concentrated HCl and extracted twice with CH₂Cl₂. The combined organic extracts were dried over Na2SO₄ and evaporated to give 2.0 g (80% yield) of BnS-(CH₂-L-Leu)-OH as an oil. An analytical sample was obtained by Kugelrohr distillation at 150° C. (0.01 torr). Characteristic analytical data are as follows: $^1$H NMR (300 MHz, CDCl₃) δ7.25–7.33 (m, 5H), 3.74 (s, 2H), 2.48–2.72 (m, 3H), 1.53–1.61 (m, 2H), 1.33–1.36 (m, 1H), 0.89 (d, J=6 Hz, 3H), 0.8 J=7 Hz, 3H); mass spectrum (CI), m/e 253 (MH⁺, 100), 235 (MH⁺-H₂O, 77); $[\alpha]^{25}_D$ –42° (c=0.6, MeOH). Anal. Calcd for C₁₄H₂₀O₂S: C, 66.63; H, 7.99; S, 12.70. Found: C, 66.91; H, 7.93; S, 13.13.

4B. Formula 5 Varying R²

By following the procedures described in Example 4A and substituting benzyl (2S)-2-[(benzylthio)methyl]-4-methylpentanoate with other compounds of Formula 4 (where the R² substituents are as indicated in the table below) there are obtained the corresponding substituted compounds of Formula 5.

Formula 5

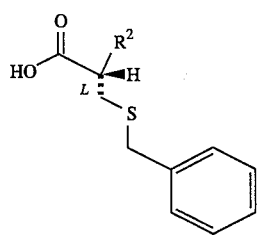

| R² | Name |
|---|---|
| methyl | BnS-(CH₂-L-Ala)-OH |
| 2-propyl | BnS-(CH₂-L-Val)-OH |
| 2-butyl | BnS-(CH₂-L-Ile)-OH |
| benzyl | BnS-(CH₂-L-Phe)-OH |
| blocked 4-hydroxyphenylmethyl | BnS-(CH₂-L-Tyr)-OH |
| blocked 3-indolylmethyl | BnS-(CH₂-L-Trp)-OH |
| 4-methoxyphenylmethyl | BnS-(CH₂-L-(Tyr-OCH₃))-OH |
| phenylethyl | BnS-(CH₂-L-Phet)-OH |
| blocked 4-aminobutyl | BnS-(CH₂-L-Lys)-OH |
| blocked 3-guanylpropyl | BnS-(CH₂-L-Arg)-OH |
| blocked 4-imidazoylmethyl | BnS-(CH₂-L-His)-OH |
| methylthioethyl | BnS-(CH₂-L-Met)-OH |

EXAMPLE 5

PREPARATION OF Phe-Ala-NH₂

5A. Preparation Of Formula 6

1. Formula 6 Where R³ Is Benzyl and R⁴ Is —CH(R⁵)—C(O)NH₂ Where R⁵ Is Methyl

The following procedure for the preparation of the amino acid residue is a modification of the procedures reported in Bodanszky, M.; Bodanszky, A. *The Practice of Peptide Synthesis;* Springer-Verlag: New York, 1984; p 129–142. A mixture of 5.00 g of Cbz-Phe-OH (Sigma Chemical Company), 2.12 g of N-hydroxysuccinimide and 3.79 g of 1,3-dicyclohexylcarbodiimide in 20 mL of dry THF was kept at 4° C. under N₂ for 26 h. The resulting precipitate was removed by filtration. To the filtrate was added an aqueous solution of 1.79 g of Ala-OH containing 0.802 g of NaOH. The mixture was stirred at room temperature for 18 h. The solid was removed by filtration and the filtrate was diluted with saturated aqueous NaHCO₃ and extracted with CHCl₃. The aqueous layer was acidified with 1M HCl and the resulting precipitate was collected by filtration, washed with water, and dried under vacuum to give 6.00 g (97% yield) of Cbz-Phe-Ala-OH, which was used without further purification. Characteristic analytical data are as follows: mp 153°–154° C.; $^1$H NMR (300 MHz, CDCl₃-CD₃OD) δ7.38–7.10 (m, 10H, 2xPh), 6.91–6.80 (br, 1H, H-N), 5.60–5.52 (br, 1H, H-N), 5.03 (s, 2H, CH₂-Bn), 4.45–4.38 (m, 2H, Hα-(Phe)+Hα-(Ala)), 3.01 (m, 2H, CH₂-(Phe)), 1.35 (d, J=7 Hz, 3H, CH₃-(Ala)).

The above described procedure was repeated using 5.65 g of Cbz-Phe-Ala-OH and excess anhydrous ammonia in THF to obtain 7.16 g of crude Cbz-Phe-Ala-NH₂. The crude product was then subjected to hydrogenolysis in MeOH over 10% Pd/C to afford 3.42 g (95% yield) of Phe-Ala-NH₂ as a yellow solid after flash chromatography (EtOAc-MeOH, 10:1). Characteristic analytical data are as follows: mp 95°–97° C.; $R_F$ 0.10 (1:2 MeOH:EtOAc); $^1$H NMR (300 MHz, CDCl₃) δ7.80–7.72 (br, 1H, H-N), 7.35–7.18 (m, 5H, Ph), 6.58–6.45 (br, 1H, H-N), 5.70–5.60 (br, 1H, H-N), 4.46 (quint, J=7 Hz, 1H, Hα-(Ala)), 3.62 (dd, J=4, 9 Hz, 1H, Hα-(Phe)), 3.21 (dd, J=4, 11 Hz, 1H, Hβ-(Phe)), 2.72 (dd, J=9, 11 Hz, 1H, Hβ-(Phe)), 1.35 (d, J=7 Hz, 3H, CH₃); $^{13}$C NMR (75 MHz, CDCl₃) δ175.3 (C=O), 174.8 (C=O), 137.6 (C-Ph), 129.4 (CH-Ph), 128.8 (CH-Ph), 127.0 (CH-Ph), 56.0 (CH-α), 48.0 (CH-α), 40.5 (CH₂), 17.7 (CH₃); $[\alpha]^{25}_D$ –25.6° (c= 1.90, EtOH).

2. Formula 6 Where R³ Is 3-indolylmethyl and R⁴ Is Benzyl

The coupling procedure described above for the preparation of Cbz-Phe-Ala-NH₂ was employed using 10.0 g of Cbz-Trp-OH (Sigma Chemical Company) and 4.84 mL of freshly distilled BnNH$_2$ in dry THF to give 11.3 g (89% yield) of crystalline Cbz-Trp-NHBn. Characteristic analytical data are as follows: mp 104°–105° C.; $^1$H NMR (300 MHz, CDCl$_3$) δ8.00–6.88 (m, 16H, Ar), 5.85 (br, 1H, H-α), 5.45 (br, 1H, H-N), 5.10 (s, 2H, CH$_2$—O), 4.57–4.45 (br, H-), 4.27 (t, 6H, CH$_2$—N), 3.38 (dd, J=4, 14 Hz, 1H, H-β), 3.16 (dd, J=8, 14 Hz, 1H, H-β); mass spectrum (EI), m/e 427 (M$^+$), 336 (M$^+$-Bn), 277 (M$^+$-Cbz-NH), 130 (M$^+$-Cbz-NH-CH-CONH-Bn), 91 (Bn$^+$); [α]$^{25}_D$+7.0° (c=0.20, EtOAC).

A solution of 2.20 g (5.15 mmol) Cbz-Trp-NHBn in 60 mL of MeOH was subjected to hydrogenolysis over Pd/C to give 1.43 g (4.88 mmol, 95%) of Trp-NHBn. Characteristic analytical data are as follows: mp 112°–114° C.; $^1$H NMR (300 MHz, CDCl$_3$) δ8.40–7.00 (m, 11H, Ar), 4.44 (d, J=6 Hz, 2H, CH$_2$—N), 3.77 (dd, J=4 Hz, 9H, H-α), 3.42 (dd, J=4, 14 Hz, 1H, H-β), 2.98 (dd, J=9, 14 Hz, 1H, H-β); mass spectrum (EI), m/e 293 (M$^+$), 277 (M$^+$-NH$_2$), 130 (M$^+$—H$_2$N—CH—CONH—Bn); [α]$^{25}_D$+42.1° (c=1.02, MeOH).

3. Formula 6 Where R$^3$ Is Benzyl and R$^4$ Is Methyl

A mixture of 1.00 g of Cbz-Phe-OH (Sigma Chemical Company), 0.385 g of N-hydroxysuccinimide and 0.541 g of 1,3-dicyclohexylcarbodiimide in 5 mL of dry THF was kept at 4° C. under N$_2$ overnight. The resulting precipitate was removed by filtration, and to the filtrate was added excess 40% aqueous methylamine at room temperature. The mixture was stirred at room temperature for 30 min. The solid was removed by filtration and the filtrate was partitioned between saturated aqueous NaHCO$_3$ and CH$_2$Cl$_2$. The organic layer was separated, dried over anhydrous Na$_2$SO$_4$, and evaporated under reduced pressure to give 1.12 g of the crude Cbz-Phe-NHMe.

To a solution of the crude product in 30 mL of MeOH was added 0.21 g of 10% Pd/C and H$_2$ was bubbled through the mixture via a dispersion tube until TLC analysis showed completion of the hydrogenolysis (3 h). The catalyst was removed by filtration and the solvent was evaporated under reduced pressure. The residue was partitioned between CHCl$_3$ and water and the aqueous layer was acidified with 1M HCl to approximately pH 2 and was extracted with CHCl$_3$ (3x). The aqueous layer was then neutralized with 10% NaOH and again was extracted with CHCl$_3$ (3x). The latter organic extract was dried over anhydrous Na$_2$SO$_4$ and was evaporated under reduced pressure to give 0.554 g (93% yield) of Phe-NHMe. Characteristic analytical data are as follows: mp 48°–50° C.; R$_F$ 0.10 (EtOAc); $^1$H NMR (300 MHz, CDCl$_3$) δ7.34–7.20 (m, 5H, Ph), 3.60 (dd, J=4, 9 Hz, 1H, H-α), 3.30 (dd, J=4, 11 Hz, 1H, H-β), 2.81 (d, 5H, CH$_3$—N), 2.65 (dd, J=9, 11 Hz, 1H, H-β); $^{13}$C NMR (75 MHz, CDCl$_3$) δ175.6 (C=O), 138.6 (C-Ph), 129.9 (CH-Ph), 129.3 (CH-Ph), 127.3 (CH-Ph), 56.8 (CH$_3$), 41.3 (CH), 26.0 (CH$_2$); mass spectrum (PCI), m/e 179 (M+1); [α]$^{25}_D$+8.5° (c=4.20, EtOH).

5B. Formula 6 Varying R$^3$, R$^4$ and R$^5$

By following the procedures described in Example 5A and substituting CBz-Phe-OH and Ala-OH with other compounds of Formulae 6A and 6B, respectively [where the substituents R$^s$ (Formula 6A), and R$^4$ and R$^5$ (Formula 6B) are as indicated in the table below] there are obtained the correspondingly substituted compounds of Formula 6.

Formula 6

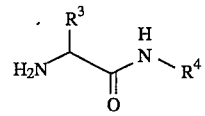

where R$^4$ is methyl or benzyl

| R$^3$ | R$^4$ | Name |
|---|---|---|
| hydrogen | —CH$_3$ | Gly—CH$_3$ |
| methyl | —Bn | Ala—Bn |
| 2-propyl | —CH$_3$ | Val—CH$_3$ |
| 2-butyl | —Bn | Leu—Bn |
| 2-methylpropyl | —CH$_3$ | Ile—CH$_3$ |
| blocked 4-aminobutyl | —Bn | Lys—Bn |
| blocked 3-guanylpropyl | —CH$_3$ | Arg—CH$_3$ |
| blocked 4-imidazoylmethyl | —Bn | His—Bn |
| benzyl | —CH$_3$ | Phe—CH$_3$ |
| blocked 4-hydroxyphenylmethyl | —Bn | Tyr—Bn |
| blocked 3-indolylmethyl | —CH$_3$ | Trp—CH$_3$ |
| 4-methoxyphenylmethyl | —Bn | (Tyr—OCH$_3$)—Bn |
| phenylethyl | —CH$_3$ | (Phet)—CH$_3$ |

Formula 6

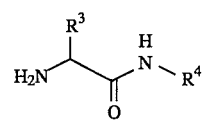

where R$^4$ is —CH—(R$^5$)—C(O)NH$_2$

| R$^3$ | R$^5$ | Name |
|---|---|---|

-continued

| | | |
|---|---|---|
| hydrogen | methyl | Gly — Ala — NH$_2$ |
| methyl | 2-butyl | Ala — Ile — NH$_2$ |
| 2-propyl | 2-methylpropyl | Val — Leu — NH$_2$ |
| 2-butyl | hydrogen | Leu — Gly — NH$_2$ |
| 2-methylpropyl | 2-propyl | Ile — Val — NH$_2$ |
| blocked 4-aminobutyl | 2-methylpropyl | Lys — Leu — NH$_2$ |
| blocked 3-guanylpropyl | methyl | Arg — Ala — NH$_2$ |
| blocked 4-imidazoylmethyl | 2-butyl | His — Ile — NH$_2$ |
| benzyl | 2-methylpropyl | Phe — Leu — NH$_2$ |
| blocked 4-hydroxyphenylmethyl | hydrogen | Tyr — Gly — NH$_2$ |
| blocked 3-indolylmethyl | 2-propyl | Trp — Val — NH$_2$ |
| 4-methoxyphenylmethyl | 2-methylpropyl | (Tyr — OCH$_3$) — Leu — NH$_2$ |
| phenylethyl | methyl | (Phet) — Ala — NH$_2$ |
| hydrogen | blocked 4-aminobutyl | Gly — Lys — NH$_2$ |
| methyl | blocked 3-guanylpropyl | Ala — Arg — NH$_2$ |
| 2-propyl | 2-imidazoylmethyl | Val — His — NH$_2$ |
| 2-butyl | blocked 4-aminobutyl | Leu — Lys — NH$_2$ |
| 2-methylpropyl | blocked 3-guanylpropyl | Ile — Arg — NH$_2$ |
| blocked 4-aminobutyl | 2-imidazoylmethyl | Lys — His — NH$_2$ |
| blocked 3-guanylpropyl | blocked 4-aminobutyl | Arg — Lys — NH$_2$ |
| blocked 4-imidazoylmethyl | blocked 3-guanylpropyl | His — Arg — NH$_2$ |
| benzyl | 2-imidazoylmethyl | Phe — His — NH$_2$ |
| blocked 4-hydroxyphenylmethyl | blocked 4-aminobutyl | Tyr — Lys — NH$_2$ |
| blocked 3-indolylmethyl | blocked 3-guanylpropyl | Trp — Arg — NH$_2$ |
| 4-methoxyphenylmethyl | 2-imidazoylmethyl | (Tyr — OCH$_3$) — His — NH$_2$ |
| phenylethyl | blocked 4-aminobutyl | (Phet) — Lys — NH$_2$ |
| hydrogen | thiolmethyl | Gly — Cys — NH$_2$ |
| methyl | methylthioethyl | Ala — Met — NH$_2$ |
| 2-propyl | hydroxymethyl | Val — Ser — NH$_2$ |
| 2-butyl | 1-hydroxyethyl | Leu — Thr — NH$_2$ |
| 2-methylpropyl | thiolmethyl | Ile — Cys — NH$_2$ |
| blocked 4-aminobutyl | methylthioethyl | Lys — Met — NH$_2$ |
| blocked 3-guanylpropyl | hydroxymethyl | Arg — Ser — NH$_2$ |
| blocked 4-imidazoylmethyl | 1-hydroxyethyl | His — Thr — NH$_2$ |
| benzyl | thiolmethyl | Phe — Cys — NH$_2$ |
| blocked 4-hydroxyphenylmethyl | methylthioethyl | Tyr — Met — NH$_2$ |
| blocked 3-indolylmethyl | hydroxymethyl | Trp — Ser — NH$_2$ |
| 4-methoxyphenylmethyl | 1-hydroxyethyl | (Tyr — OCH$_3$) — Thr — NH$_2$ |
| phenylethyl | hydroxymethyl | (Phet) — Ser — NH$_2$ |
| blocked 3-guanylpropyl | methylthioethyl | Arg — Met — NH$_2$ |

EXAMPLE 6

PREPARATION OF HS-(CH$_2$-L-Leu)-Phe-Ala-NH$_2$

6A. Preparation of Formula 7 Where $R^2$ Is 2-Methylpropyl, $R^3$ Is Benzyl and $R^4$ Is Methyl BnS-(CH$_2$-L-Leu)-OH and Phe-Ala-NH$_2$ were coupled using the procedure described in the Bodanszky reference (i.e., Bodanszky, M., Bodanszky, A. *The Practice of Peptide Synthesis;* Springer-Verlag: New York, 1984, p 145) to give the S-benzyl peptide, i.e., BnS-(CH$_2$-L-Leu)-Phe-Ala-NH$_2$ as a glass in 78% yield. Characteristic analytical data are as follows: $^1$H NMR (300 MHz, CDCl$_3$) δ7.21–7.35 (m, 10H), 6.63 (d, J=8 Hz, 1H), 6.23 (br s, 1H), 5.85 (d, J=7 Hz, 1H), 5.25 (br s, 1H), 4.42–4.57 (m, 2H), 3.65 (s, 2H), 3.23 (dd, J=7, 14 Hz, 1H), 3.04 (dd, J=8, 14 Hz, 1H), 2.47–2.50 (m, 2H), 2.22–2.26 (m, 1H), 1.11–1.40 (m, 3H), 1.32 (d, J=7 Hz, 3H), 0.76 (d, J=9 Hz, 3H), 0.74 (d, Hz, 3H).

6B. Preparation of Formula 8 Where $R^2$ Is 2-Methylpropyl, $R^3$ Is Benzyl and $R^4$ Is Methyl Debenzylation of BnS-(CH$_2$-L-Leu)-Phe-Ala-NH$_2$ was done using the Na and liquid ammonia procedure of Evans and co-workers (Evans, D. A.; Mathre, D. J.; Scott, W. L. *J. Org. Chem.* 1985, 50, 1830–1835) to give HS-(CH$_2$-L-Leu)-Phe-Ala-NH$_2$ in 89% yield after flash chromatography with CHCl$_3$-EtOH. Characteristic analytical data are as follows: mp 217°–219° C.; $^1$H NMR (CDCl$_3$) δ7.1–7.3 (m, 5H), 6.72 (m, 1H), 6.25 (m, 1H), 6.08 (br s, 1H), 5.38 (br s, 1H), 4.71 (q, J=7 Hz, 1H), 4.44 (p, J=7 Hz, 1H), 3.20 (dd, J=7, 13 Hz, 1H), 3.07 (dd, J=7, 13 Hz, 1H), 2.50–2.70 (m, 2H), 2.30–2.41 (m, 1H), 1.20–1.50 (m, 3H), 1.34 (d, J=7 Hz, 3H), 0.87 (d, J=7 Hz, 3H), 0.83 (d, J=7 Hz, 3H); mass spectrum (CI), m/e 380 (MH$^+$, 100); [α]$^{25}_D$ −24° (c=0.35, MeOH).

6C. Formula 8 Where $R^2$ Is 2-Methylpropyl Varying $R^3$, $R^4$ and $R^5$

By following the procedures described in Examples 6A and 6B and substituting Phe-Ala-NH$_2$ with other compounds of Formula 6 (e.g., compounds with $R^3$, $R^4$ and $R^5$ that are prepared according to Example 5A and exemplified in Example 5B) there are obtained the correspondingly substituted of compounds of Formula 8.

Formula 8

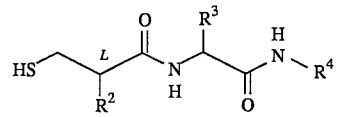

where R⁴ is methyl or benzyl

| R² | R³ | R⁴ |
|---|---|---|
| 2-methylpropyl | hydrogen | —CH₃ |
| 2-methylpropyl | methyl | —Bn |
| 2-methylpropyl | 2-propyl | —CH₃ |
| 2-methylpropyl | 2-butyl | —Bn |
| 2-methylpropyl | 2-methylpropyl | CH₃ |
| 2-methylpropyl | blocked 4-aminobutyl | —Bn |
| 2-methylpropyl | blocked 3-guanylpropyl | —CH₃ |
| 2-methylpropyl | blocked 4-imidazoylmethyl | —Bn |
| 2-methylpropyl | benzyl | —CH₃ |
| 2-methylpropyl | blocked 4-hydroxyphenylmethyl | —Bn |
| 2-methylpropyl | 3-indoylmethyl | —CH₃ |
| 2-methylpropyl | 4-methoxyphenylmethyl | —Bn |
| 2-methylpropyl | phenylethyl | —CH₃ |

Formula 8

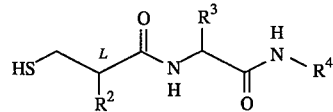

where R⁴ is —CH—(R⁵)—C(O)NH₂

| R² | R³ | R⁵ |
|---|---|---|
| 2-methylpropyl | hydrogen | methyl |
| 2-methylpropyl | methyl | 2-butyl |
| 2-methylpropyl | 2-propyl | 2-methylpropyl |
| 2-methylpropyl | 2-butyl | hydrogen |
| 2-methylpropyl | 2-methylpropyl | 2-propyl |
| 2-methylpropyl | blocked 4-aminobutyl | 2-methylpropyl |
| 2-methylpropyl | blocked 3-guanylpropyl | methyl |
| 2-methylpropyl | blocked 4-imidazoylmethyl | 2-butyl |
| 2-methylpropyl | benzyl | 2-methylpropyl |
| 2-methylpropyl | blocked 4-hydroxyphenylmethyl | hydrogen |
| 2-methylpropyl | 3-indoylmethyl | 2-propyl |
| 2-methylpropyl | 4-methoxyphenylmethyl | 2-methylpropyl |
| 2-methylpropyl | phenylethyl | methyl |
| 2-methylpropyl | hydrogen | blocked 4-aminobutyl |
| 2-methylpropyl | methyl | blocked 3-guanylpropyl |
| 2-methylpropyl | 2-propyl | blocked 4-imidazoylmethyl |
| 2-methylpropyl | 2-butyl | blocked 4-aminobutyl |
| 2-methylpropyl | 2-methylpropyl | blocked 3-guanylpropyl |
| 2-methylpropyl | blocked 4-aminobutyl | blocked 4-imidazoylmethyl |
| 2-methylpropyl | blocked 3-guanylpropyl | blocked 4-aminobutyl |
| 2-methylpropyl | blocked 4-imidazoylmethyl | blocked 3-guanylpropyl |
| 2-methylpropyl | benzyl | blocked 4-imidazoylmethyl |
| 2-methylpropyl | blocked 4-hydroxyphenylmethyl | blocked 4-aminobutyl |
| 2-methylpropyl | 3-indoylmethyl | blocked 3-guanylpropyl |
| 2-methylpropyl | 4-methoxyphenylmethyl | blocked 4-imidazoylmethyl |
| 2-methylpropyl | phenylethyl | blocked 4-aminobutyl |
| 2-methylpropyl | hydrogen | thiolmethyl |
| 2-methylpropyl | methyl | methylthioethyl |
| 2-methylpropyl | 2-propyl | hydroxymethyl |
| 2-methylpropyl | 2-butyl | 1-hydroxyethyl |
| 2-methylpropyl | 2-methylpropyl | thiolmethyl |
| 2-methylpropyl | blocked 4-aminobutyl | methylthioethyl |
| 2-methylpropyl | blocked 3-guanylpropyl | hydroxymethyl |
| 2-methylpropyl | blocked 4-imidazoylmethyl | 1-hydroxyethyl |
| 2-methylpropyl | benzyl | thiolmethyl |
| 2-methylpropyl | blocked 4-hydroxyphenylmethyl | methylthioethyl |
| 2-methylpropyl | 3-indoylmethyl | hydroxymethyl |
| 2-methylpropyl | 4-methoxyphenylmethyl | 1-hydroxyethyl |
| 2-methylpropyl | phenylethyl | hydroxymethyl |

6D. Formula 8 Varying $R^2$, $R^3$, $R^4$ and $R^5$

By following the procedures described in Examples 6A and 6B and substituting Bns-(CH$_2$-L-Leu)-OH with other compounds of Formula 5 (e.g., compounds with $R^2$ that are prepared according to Example 4A and exemplified with Example 4B) and Phe-Ala-NH$_2$ with other compounds of Formula 6 (e.g., compounds with $R^3$, $R^4$ and $R^5$ that are prepared according to Example 5A and exemplified with Example 5B) there are obtained the following correspondingly substituted compounds of Formula 8.

Formula 8

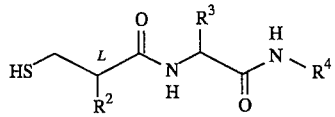

where $R^4$ is methyl or benzyl

| $R^2$ | $R^3$ | $R^4$ |
|---|---|---|
| 4-methoxyphenyl | hydrogen | —CH$_3$ |
| blocked 4-hydroxyphenyl | methyl | —Bn |
| benzyl | 2-propyl | —CH$_3$ |
| 2-butyl | 2-butyl | —Bn |
| 2-butyl | 2-methylpropyl | —CH$_3$ |
| benzyl | blocked 4-aminobutyl | —Bn |
| blocked 4-hydroxyphenyl | blocked 3-guanylpropyl | —CH$_3$ |
| 4-methoxyphenyl | blocked 4-imidazoylmethyl | —Bn |
| 4-methoxyphenyl | benzyl | —CH$_3$ |
| blocked 4-hydroxyphenyl | blocked 4-hydroxyphenyl-methyl | —Bn |
| benzyl | 3-indoylmethyl | —CH$_3$ |
| 2-butyl | 4-methoxyphenylmethyl | —Bn |
| 2-butyl | phenylethyl | —CH$_3$ |

Formula 8

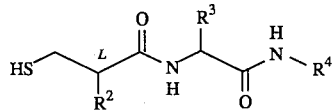

where $R^4$ is —CH—($R^5$)—C(O)NH$_2$

| $R^2$ | $R^3$ | $R^5$ |
|---|---|---|
| benzyl | hydrogen | methyl |
| blocked 4-hydroxyphenyl | methyl | 2-butyl |
| 4-methoxyphenyl | 2-propyl | 2-methylpropyl |
|  | 2-butyl | hydrogen |
| 4-methoxyphenyl | 2-methylpropyl | 2-propyl |
| blocked 4-hydroxyphenyl | blocked 4-aminobutyl | 2-methylpropyl |
| benzyl | blocked 3-guanylpropyl | methyl |
| 2-butyl | blocked 4-imidazoylmethyl | 2-butyl |
| 2-butyl | benzyl | 2-methylpropyl |
| benzyl | blocked 4-hydroxyphenyl-methyl | hydrogen |
| blocked 4-hydroxyphenyl | 3-indoylmethyl | 2-propyl |
| 4-methoxyphenyl | 4-methoxyphenylmethyl | 2-methylpropyl |
| 4-methoxyphenyl | phenylethyl | methyl |
| blocked 4-hydroxyphenyl | hydrogen | blocked 4-aminobutyl |
| benzyl | methyl | blocked 3-guanylpropyl |
| 2-butyl | 2-propyl | blocked 4-imidazoyl-methyl |
| 2-butyl | 2-butyl | blocked 4-aminobutyl |
| benzyl | 2-methylpropyl | blocked 3-guanylpropyl |
| blocked 4-hydroxyphenyl | blocked 4-aminobutyl | blocked 4-imidazoyl-methyl |
| 4-methoxyphenyl | blocked 3-guanylpropyl | blocked 4-aminobutyl |
| 4-methoxyphenyl | blocked 4-imidazoylmethyl | blocked 3-guanylpropyl |
| blocked 4-hydroxyphenyl | benzyl | blocked 4-imidazoyl-methyl |
| benzyl | blocked 4-hydroxyphenyl-methyl | blocked 4-aminobutyl |
| 2-butyl | 3-indoylmethyl | blocked 3- |

-continued

| R¹ | R² | R³ |
|---|---|---|
| 2-butyl | 4-methoxyphenylmethyl | guanylpropyl |
| | | blocked 4-imidazoyl-methyl |
| benzyl | phenylethyl | blocked 4-aminobutyl |
| blocked 4-hydroxyphenyl | hydrogen | thiolmethyl |
| 4-methoxyphenyl | methyl | methylthioethyl |
| 2-butyl | 2-propyl | hydroxymethyl |
| benzyl | 2-butyl | 1-hydroxyethyl |
| blocked 4-hydroxyphenyl | 2-methylpropyl | thiolmethyl |
| 4-methoxyphenyl | blocked 4-aminobutyl | methylthioethyl |
| blocked 4-hydroxyphenyl | blocked 3-guanylpropyl | hydroxymethyl |
| benzyl | blocked 4-imidazoylmethyl | 1-hydroxyethyl |
| 2-butyl | benzyl | thiolmethyl |
| 2-butyl | blocked 4-hydroxyphenyl-methyl | methylthioethyl |
| benzyl | 3-indoylmethyl | hydroxymethyl |
| blocked 4-hydroxyphenyl | 4-methoxyphenylmethyl | 1-hydroxyethyl |
| 4-methoxyphenyl | phenylethyl | hydroxymethyl |

EXAMPLE 7

PREPARATION OF MeS-(CH₂-L-Leu)-Phe-Ala-NH₂

7A. Formula 10 Where $R^1$ Is $CH_3$, $R^2$ Is 2-Methylpropyl, $R^3$ Is Benzyl and $R^4$ Is Methyl To 143 mg of HS-(CH₂-L-Leu)-Phe-Ala-NH₂ under nitrogen was added a solution of 10 mg of Na in 1.6 mL of MeOH, followed by 35 μL of CH₃I. The mixture was stirred at 40° C. for 6 h, then the solvent was evaporated. The residue was partitioned between water and EtOAc and the aqueous layer was extracted twice with EtOAc. The combined organic layers were dried over Na₂SO₄ and evaporated, and the residue was purified by flash chromatography on silica gel to give 113 mg (76% yield) of Me-S-(CH₂-L-Leu)-Phe-Ala-NH₂ as a white solid. Characteristic analytical data are as follows: mp 191°–193° C.; ¹H NMR (300 MHz, CDCl₃-CD₃OD) δ7.24–7.33 (m, 5H), 4.65 (t, J=8 Hz, 1H), 4.37 (q, J=8 Hz, 1H), 3.16 (dd, J=7, 14 Hz, 1H), 3.04 (dd, J=7, 14 Hz, 1H), 2.48–2.60 (m, 3H), 2.05 (s, 3H), 1.2–1.55 (m, 3H), 1.32 (d, J=7 Hz, 3H), 0.86 (d, J=7 Hz, 3H), 0.82 (d, J=7 Hz, 3H); mass spectrum (EI), m/e 393 (M⁺, 35); $[\alpha]^{25}_{546}$ −39° (c=0.29, MeOH).

7B. Formula 10 Where $R^1$ Is n-butyl

By following the procedure described in Example 7A and substituting n-butyl iodide for methyl iodide, n-Bu-S-(CH₂-L-Leu)-Phe-Ala-NH₂ was obtained as a solid. Characteristic analytical data are as follows: mp 180°–183° C.; ¹H NMR (300 MHz, CDCl₃) δ7.21–7.36 (m, 5H), 6.79 (d, J=8 Hz, 1H, NH), 6.30 (br s, 1H, NH), 6.08 (d, J=6 Hz, 1H, NH), 5.31 (br s, 1H, NH), 4.58 (q, J=6 Hz, 1H), 4.47 (p, J=7 Hz, 1H), 3.25 (dd, J=6, 14 Hz, 1H), 3.07 (dd, J=8, 14 Hz, 1H), 2.66 (dd, J=5, 13 Hz, 1H), 2.42–2.5 (m, 4H), 1.38–1.56 (m, 7H), 1.34 (d, J=7 Hz, 3H), 0.91 (t, J=7 Hz, 3H), 0.85 (d, J=7 Hz, 3H), 0.79 (d, J= 6 Hz, 3H); mass spectrum (CI), m/e 436 (MH⁺, 100); $[\alpha]^{25}_{546}$ −41° (c=0.4, MeOH).

7C. Formula 10 Varying $R^1$, $R^2$, $R^3$, $R^4$ and $R^5$

By following the procedures described in Examples 7A and substituting CH₃I with other compounds of Formula 9 (e.g., compounds with $R^1$) and HS-(CH₂-L-Leu)-Phe-Ala-NH₂ with other compounds of Formula 8 (e.g., compounds with $R^2$, $R^3$, $R^4$ and $R^5$ that are prepared according to Example 6A and exemplified in Example 6B) there are obtained the correspondingly substituted of compounds of Formula 10.

Formula 10

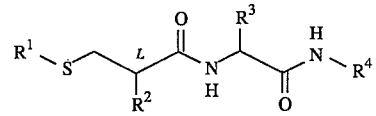

where $R^4$ is methyl or benzyl

| R¹ | R² | R³ | R⁴ |
|---|---|---|---|
| ethyl | 4-methoxyphenyl | hydrogen | —CH₃ |
| benzyl | blocked 4-hydroxyphenyl | methyl | —Bn |
| phenethyl | benzyl | 2-propyl | —CH₃ |
| blocked 4-hydroxyphenethyl | 2-butyl | 2-butyl | —Bn |
| blocked 2-(4-imidazolyl)ethyl | 2-butyl | 2-methylpropyl | —CH₃ |
| blocked 3-carboxypropyl | benzyl | blocked 4-aminobutyl | —Bn |
| ethyl | blocked 4-hydroxyphenyl | blocked 3-guanylpropyl | —CH₃ |
| benzyl | 4-methoxyphenyl | blocked 4-imidazoylmethyl | —Bn |

-continued

| | | | |
|---|---|---|---|
| phenethyl | 4-methoxyphenyl | benzyl | —CH₃ |
| blocked 4-hydroxyphenethyl | blocked 4-hydroxyphenyl | blocked 4-hydroxyphenylmethyl | —Bn |
| blocked 2-(4-imidazolyl)ethyl | benzyl | 3-indoylmethyl | —CH₃ |
| blocked 3-carboxypropyl | 2-butyl | 4-methoxyphenylmethyl | —Bn |
| ethyl | 2-butyl | phenylethyl | —CH₃ |

Formula 10

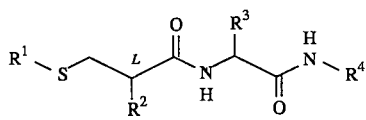

where R⁴ is —CH—(R⁵)—C(O)NH₂

| R¹ | R² | R³ | R⁵ |
|---|---|---|---|
| benzyl | 2-butyl | hydrogen | methyl |
| phenethyl | benzyl | methyl | 2-butyl |
| blocked 4-hydroxyphenethyl | blocked 4-hydroxyphenyl | 2-propyl | 2-methylpropyl |
| blocked 2-(4-imidazolyl)ethyl | 4-methoxyphenyl | 2-butyl | hydrogen |
| blocked 3-carboxypropyl | 4-methoxyphenyl | 2-methylpropyl | 2-propyl |
| ethyl | blocked 4-hydroxyphenyl | blocked 4-aminobutyl | 2-methylpropyl |
| benzyl | benzyl | blocked 3-guanylpropyl | methyl |
| phenethyl | 2-butyl | blocked 4-imidazoylmethyl | 2-butyl |
| blocked 4-hydroxyphenethyl | 2-butyl | benzyl | 2-methylpropyl |
| blocked 2-(4-imidazolyl)ethyl | benzyl | blocked 4-hydroxyphenylmethyl | hydrogen |
| blocked 3-carboxypropyl | blocked 4-hydroxyphenyl | 3-indoylmethyl | 2-propyl |
| ethyl | 4-methoxyphenyl | 4-methoxyphenylmethyl | 2-methylpropyl |
| benzyl | 4-methoxyphenyl | phenylethyl | methyl |
| phenethyl | blocked 4-hydroxyphenyl | hydrogen | blocked 4-aminobutyl |
| blocked 4-hydroxyphenethyl | benzyl | methyl | blocked 3-guanylpropyl |
| blocked 2-(4-imidazolyl)ethyl | 2-butyl | 2-propyl | blocked 4-imidazoylmethyl |
| blocked 3-carboxypropyl | 2-butyl | 2-butyl | blocked 4-aminobutyl |
| ethyl | benzyl | 2-methylpropyl | blocked 3-guanylpropyl |
| benzyl | blocked 4-hydroxyphenyl | blocked 4-aminobutyl | blocked 4-imidazoylmethyl |
| phenethyl | 4-methoxyphenyl | blocked 3-guanylpropyl | blocked 4-aminobutyl |
| blocked 4-hydroxyphenethyl | 4-methoxyphenyl | blocked 4-imidazoylmethyl | blocked 3-guanylpropyl |
| blocked 2-(4-imidazolyl)ethyl | blocked 4-hydroxyphenyl | benzyl | blocked 4-imidazoylmethyl |
| blocked 3-carboxypropyl | benzyl | blocked 4-hydroxyphenylmethyl | blocked 4-aminobutyl |
| ethyl | 2-butyl | 3-indoylmethyl | blocked 3-guanylpropyl |
| benzyl | 2-butyl | 4-methoxyphenylmethyl | blocked 4-imidazoylmethyl |
| phenethyl | benzyl | phenylethyl | blocked 4-aminobutyl |
| blocked 4-hydroxyphenethyl | blocked 4-hydroxyphenyl | hydrogen | thiolmethyl |

| | | | |
|---|---|---|---|
| ethyl blocked 2-(4-imidazolyl)ethyl | 4-methoxyphenyl | methyl | methylthioethyl |
| blocked 3-carboxypropyl | 2-butyl | 2-propyl | hydroxymethyl |
| ethyl | benzyl | 2-butyl | 1-hydroxyethyl |
| benzyl | blocked 4-hydroxyphenyl | 2-methylpropyl | thiolmethyl |
| phenethyl | 4-methoxyphenyl | blocked 4-aminobutyl | methylthioethyl |
| blocked 4-hydroxyphen-ethyl | blocked 4-hydroxyphenyl | blocked 3-guanylpropyl | hydroxymethyl |
| blocked 2-(4-imidazolyl)ethyl | benzyl | blocked 4-imidazoylmethyl | 1-hydroxyethyl |
| blocked 3-carboxypropyl | 2-butyl | benzyl | thiolmethyl |
| ethyl | 2-butyl | blocked 4-hydroxyphenyl methyl | methylthioethyl |
| benzyl | benzyl | 3-indoylmethyl | hydroxymethyl |
| phenethyl | blocked 4-hydroxyphenyl | 4-methoxy-phenylmethyl | 1-hydroxyethyl |
| blocked 4-hydroxy-phenethyl | 4-methoxyphenyl | phenylethyl | hydroxymethyl |

EXAMPLE 8

PREPARATION OF Me-(RS)-SO-(CH$_2$-L-Leu)-Phe-Ala-NH$_2$

8A. Formula 11 Where $R^1$ Is $CH_3$, $R^2$ Is 2-Methylpropyl, $R^3$ Is Benzyl and $R^4$ Is Methyl To a cold (−10° C.) solution of 50 mg of Me-S-(CH$_2$-L-Leu)-phe-Ala-NH$_2$ in 4 mL of CH$_2$Cl$_2$ and 2 mL of MeOH was added 25 mg of m-chloroperbenzoic acid. The reaction mixture was stirred at −10° C. for 8 h. The solvents were removed by evaporation and the residue was triturated several times with ether. The residue was purified by flash chromatography on silica gel (CHCl$_3$-EtOH eluent) to give 40 mg (77% yield) of Me-(RS)-SO-(CH$_2$-L-Leu)-Phe-Ala-NH$_2$ as a mixture of two diastereomers. Characteristic analytical data are as follows: $^1$H NMR (300 MHz, CDCl$_3$-CD$_3$OD) δ7.20–7.35 (m, 5H), 4.68 (m, 1H), 4.43 (m, 1H), 3.12–3.26 (m, 1H), 2.80–3.05 (m, 2H), 2.56–2.70 (m, 2H), 2.53 & 2.48 (s, 3H), 1.25–1.68 (m, 3H), 1.34 & 1.32 (d, J=7 Hz, 3H), 0.82–0.91 (m, 6H).

8B. Formula 11 Where $R^1$ n-Butyl, $R^2$ Is 2-Methylpropyl, $R^3$ Is Benzyl and $R^4$ Is Methyl Following the procedure described in Example 8A and substituting n-Bu-S-(CH$_2$-L-Leu)-Phe-Ala-NH$_2$ for Me-S-(CH$_2$-L-Leu)-Phe-Ala-NH$_2$, n-Bu-(RS)-SO-(CH$_2$-L-Leu)-Phe-Ala-NH$_2$ was obtained as a mixture of two diastereomers.

8C. Formula 11 Varying $R^1$, $R^2$, $R^3$, $R^4$ and $R^5$

By following the procedures described in Examples 8A and substituting MeS-(CH$_2$-L-Leu)-Phe-Ala-NH$_2$ with other compounds of Formula 10 (e.g., compounds with $R^1$, $R^2$, $R^3$, $R^4$ and $R^5$ that are prepared according to Examples 7A and 7B, and exemplified in Example 7C) there are obtained the correspondingly substituted of compounds of Formula 11.

Formula 11

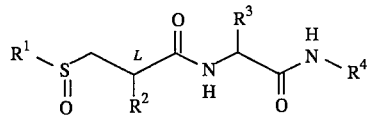

where $R^4$ is methyl or benzyl

| $R^1$ | $R^2$ | $R^3$ | $R^4$ |
|---|---|---|---|
| ethyl | 4-methoxyphenyl | hydrogen | —CH$_3$ |
| benzyl | blocked 4-hydroxy-phenyl | methyl | —Bn |
| phenethyl | benzyl | 2-propyl | —CH$_3$ |
| blocked 4-hydroxy-phenethyl | 2-butyl | 2-butyl | —Bn |
| blocked 2-(4-imidazolyl)ethyl | 2-butyl | 2-methylpropyl | —CH$_3$ |
| blocked 3-carboxy-propyl | benzyl | blocked 4-aminobutyl | —Bn |
| ethyl | blocked 4-hydroxy-phenyl | blocked 3-guanylpropyl | —CH$_3$ |

| | | | |
|---|---|---|---|
| benzyl | 4-methoxyphenyl | blocked 4-imidazoylmethyl | —Bn |
| phenethyl | 4-methoxyphenyl | benzyl | —CH₃ |
| blocked 4-hydroxyphenethyl | blocked 4-hydroxyphenyl | blocked 4-hydroxyphenylmethyl | —Bn |
| blocked 2-(4-imidazolyl)ethyl | benzyl | 3-indoylmethyl | —CH₃ |
| blocked 3-carboxypropyl | 2-butyl | 4-methoxyphenylmethyl | —Bn |
| ethyl | 2-butyl | phenylethyl | —CH₃ |

Formula 11

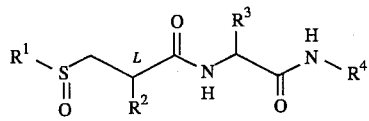

where $R^4$ is $-CH-(R^5)-C(O)NH_2$

| R¹ | R² | R³ | R⁵ |
|---|---|---|---|
| benzyl | 2-butyl | hydrogen | methyl |
| phenethyl | benzyl | methyl | 2-butyl |
| blocked 4-hydroxyphenethyl | blocked 4-hydroxyphenyl | 2-propyl | 2-methylpropyl |
| blocked 2-(4-imidazolyl)ethyl | 4-methoxyphenyl | 2-butyl | hydrogen |
| blocked 3-carboxypropyl | 4-methoxyphenyl | 2-methylpropyl | 2-propyl |
| ethyl | blocked 4-hydroxyphenyl | blocked 4-aminobutyl | 2-methylpropyl |
| benzyl | benzyl | blocked 3-guanylpropyl | methyl |
| phenethyl | 2-butyl | blocked 4-imidazoylmethyl | 2-butyl |
| blocked 4-hydroxyphenethyl | 2-butyl | benzyl | 2-methylpropyl |
| blocked 2-(4-imidazolyl)ethyl | benzyl | blocked 4-hydroxyphenylmethyl | hydrogen |
| blocked 3-carboxypropyl | blocked 4-hydroxyphenyl | 3-indoylmethyl | 2-propyl |
| ethyl | 4-methoxyphenyl | 4-methoxyphenylmethyl | 2-methylpropyl |
| benzyl | 4-methoxyphenyl | phenylethyl | methyl |
| phenethyl | blocked 4-hydroxyphenyl | hydrogen | blocked 4-aminobutyl |
| blocked 4-hydroxyphenethyl | benzyl | methyl | blocked 3-guanylpropyl |
| blocked 2-(4-imidazolyl)ethyl | 2-butyl | 2-propyl | blocked 4-imidazoylmethyl |
| blocked 3-carboxypropyl | 2-butyl | 2-butyl | blocked 4-aminobutyl |
| ethyl | benzyl | 2-methylpropyl | blocked 3-guanylpropyl |
| benzyl | blocked 4-hydroxyphenyl | blocked 4-aminobutyl | blocked 4-imidazoylmethyl |
| phenethyl | 4-methoxyphenyl | blocked 3-guanylpropyl | blocked 4-aminobutyl |
| blocked 4-hydroxyphenethyl | 4-methoxyphenyl | blocked 4-imidazoylmethyl | blocked 3-guanylpropyl |
| blocked 2-(4-imidazolyl)ethyl | blocked 4-hydroxyphenyl | benzyl | blocked 4-imidazoylmethyl |
| blocked 3-carboxypropyl | benzyl | blocked 4-hydroxyphenylmethyl | blocked 4-aminobutyl |
| ethyl | 2-butyl | 3-indoylmethyl | blocked 3-guanylpropyl |
| benzyl | 2-butyl | 4-methoxyphenylmethyl | blocked 4-imidazoylmethyl |
| phenethyl | benzyl | phenylethyl | blocked 4-aminobutyl |

| | | | |
|---|---|---|---|
| blocked 4-hydroxyphenethyl | blocked 4-hydroxyphenyl | hydrogen | thiolmethyl |
| blocked 2-(4-imidazolyl)ethyl | 4-methoxyphenyl | methyl | methylthioethyl |
| blocked 3-carboxypropyl | 2-butyl | 2-propyl | hydroxymethyl |
| ethyl | benzyl | 2-butyl | 1-hydroxyethyl |
| benzyl | blocked 4-hydroxyphenyl | 2-methylpropyl | thiolmethyl |
| phenethyl | 4-methoxyphenyl | blocked 4-aminobutyl | methylthioethyl |
| blocked 4-hydroxyphenethyl | blocked 4-hydroxyphenyl | blocked 3-guanylpropyl | hydroxymethyl |
| blocked 2-(4-imidazolyl)ethyl | benzyl | blocked 4-imidazoylmethyl | 1-hydroxyethyl |
| blocked 3-carboxypropyl | 2-butyl | benzyl | thiolmethyl |
| ethyl | 2-butyl | blocked 4-hydroxyphenylmethyl | methylthioethyl |
| benzyl | benzyl | 3-indoylmethyl | hydroxymethyl |
| phenethyl | blocked 4-hydroxyphenyl | 4-methoxyphenylmethyl | 1-hydroxyethyl |
| blocked 4-hydroxyphenethyl | blocked 4-methoxyphenyl | phenylethyl | hydroxymethyl |

EXAMPLE 9

PREPARATION OF Me-(RS)-SO(NH)-(CH$_2$-L-Leu)-Phe-Ala-NH$_2$

9A. Formula I Where X Is O, R$^1$ Is CH$_3$, R$^2$ Is 2-Methylpropyl, R$^3$ Is Benzyl and R$^4$ Is Methyl To a solution of 20 mg of Me-(RS)-SO-(CH$_2$-L-Leu)-Phe-Ala-NH$_2$ in 1.5 mL of THF was added 32 mg of O-mesitylsulfonylhydroxylamine. The resulting mixture was stirred at 25° C. for 10 h [according to Johnson, C. R.; Kirchhoff, R. A.; Corkins, H. G. *J. Org. Chem.* 1974, 39, 2458–2459]. The reaction mixture was partitioned between EtOAc and water. NaOH (10% aqueous) was added to bring the aqueous layer to pH 9. The aqueous layer was extracted twice with EtOAc and the combined organic layers were dried over Na$_2$SO$_4$ and evaporated. The residue was purified by flash chromatography followed by preparative TLC on silica gel (CHCl$_3$-EtOH eluents) to give 6 mg (29% yield) of Me-(RS)-SO(NH)-(CH$_2$-L-Leu)-Phe-Ala-NH$_2$ as a mixture of two diastereomers. Characteristic analytical data are as follows: $^1$H NMR (300 MHz, CDCl$_3$-CD$_3$OD) δ7.23–7.34 (m, 5H), 4.56–4.62 (m, 1H), 4.36–4.42 (m, 1H), 3.40–3.58 (m, 1H), 3.14–3.26 (m, 1H), 2.86–3.07 (m, 3H), 2.75 & 2.71 (s, 3H), 1.34 & 1.33 (d, J=7 Hz, 3H), 1.21–1.56 (m, 3H), 0.90 (d, J=7 Hz, 3H), 0.85 (d, J=6 Hz mass spectrum (PCI), m/e 425 (MH$^+$, 8), 346 (100).

9B. Formula I Where X Is O, R$^1$ Is n-butyl, R$^2$ Is 2-Methylpropyl, R$^3$ Is Benzyl and R$^4$ Is Methyl Following the procedure described in Example 9A and substituting n-Bu-SO-(CH$_2$-L-Leu)-Phe-Ala-NH$_2$ for Me-SO-(CH$_2$-L-Leu)-Phe-Ala-NH$_2$, n-Bu-(RS)-SO(NH)-(CH$_2$-L-Leu)-Phe-Ala-NH$_2$ was obtained as a mixture of two diastereomers. Characteristic analytical data are as follows: mp 141°–144° C. (lyophilized powder); $^1$H NMR (300 MHz, CDCl$_3$-CD$_3$OD) δ7.23–7.32 (m, 5H), 4.51 (t, J=7 Hz, 1H), 4.35 (q, J=8 Hz, 1H), 2.8–3.3 (m, 7H), 1.2–1.8 (m, 7H), 1.33 (d, 1.5H), 1.32 (d, J=7 Hz, 1.5H), 0.96 (t, J=7 Hz, 3H), 0.88 (d, J=6 Hz, 3H), 0.84 (d, J=6 Hz, 3H); mass spectrum (CI), m/e 467 (MH$^+$, 26), 346 (MH$^+$-n-BuSO-(NH)H, 100); [α]$^{25}_{546}$−31° (c=0.12, MeOH).

9C. Formula I Varying R$^1$, R$^2$, R$^3$, R$^4$ and R$^5$

By following the procedures described in Examples 9A and 9B and substituting Me-(RS)-SO-(CH$_2$-L-Leu)-Phe-Ala-NH$_2$ with other compounds of Formula 10 (e.g., compounds with R$^1$, R$^2$, R$^3$, R$^4$ and R$^5$ that are prepared according to Examples 8A and 8B, and exemplified in Example 8C) there are obtained the correspondingly substituted of compounds of Formula I.

Formula I

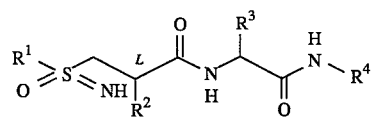

where R$^4$ is methyl or benzyl

| R$^1$ | R$^2$ | R$^3$ | R$^4$ |
|---|---|---|---|
| ethyl | 4-methoxyphenyl | hydrogen | —CH$_3$ |

-continued

| | | | |
|---|---|---|---|
| benzyl | 4-hydroxyphenyl | methyl | —Bn |
| phenethyl | benzyl | 2-propyl | —CH$_3$ |
| 4-hydroxyphenethyl | 2-butyl | 2-butyl | —Bn |
| 2-(4-imidazolyl)ethyl | 2-butyl | 2-methylpropyl | —CH$_3$ |
| 3-carboxypropyl | benzyl | 4-aminobutyl | —Bn |
| ethyl | 4-hydroxyphenyl | 3-guanylpropyl | —CH$_3$ |
| benzyl | 4-methoxyphenyl | 4-imidazoylmethyl | —Bn |
| phenethyl | 4-methoxyphenyl | benzyl | —CH$_3$ |
| 4-hydroxyphenethyl | 4-hydroxyphenyl | 4-hydroxyphenylmethyl | —Bn |
| 2-(4-imidazolyl)ethyl | benzyl | 3-indoylmethyl | —CH$_3$ |
| 3-carboxypropyl | 2-butyl | 4-methoxyphenylmethyl | —Bn |
| ethyl | 2-butyl | phenylethyl | —CH$_3$ |

Formula I

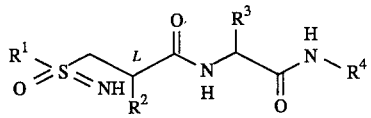

where R$^4$ is —CH—(R$^5$)—C(O)NH$_2$

| R$^1$ | R$^2$ | R$^3$ | R$^5$ |
|---|---|---|---|
| benzyl | 2-butyl | hydrogen | methyl |
| phenethyl | benzyl | methyl | 2-butyl |
| 4-hydroxyphenethyl | 4-hydroxyphenyl | 2-propyl | 2-methylpropyl |
| 2-(4-imidazolyl)-ethyl | 4-methoxyphenyl | 2-butyl | hydrogen |
| 3-carboxypropyl | 4-methoxyphenyl | 2-methylpropyl | 2-propyl |
| ethyl | 4-hydroxyphenyl | 4-aminobutyl | 2-methylpropyl |
| benzyl | benzyl | 3-guanylpropyl | methyl |
| phenethyl | 2-butyl | 4-imidazoyl-methyl | 2-butyl |
| 4-hydroxyphenethyl | 2-butyl | benzyl | 2-methylpropyl |
| 2-(4-imidazolyl)-ethyl | benzyl | 4-hydroxyphenyl-methyl | hydrogen |
| 3-carboxypropyl | 4-hydroxyphenyl | 3-indoylmethyl | 2-propyl |
| ethyl | 4-methoxyphenyl | 4-methoxyphenyl-methyl | 2-methylpropyl |
| benzyl | 4-methoxyphenyl | phenylethyl | methyl |
| phenethyl | 4-hydroxyphenyl | hydrogen | 4-aminobutyl |
| 4-hydroxyphenethyl | benzyl | methyl | 3-guanylpropyl |
| 2-(4-imidazolyl)-ethyl | 2-butyl | 2-propyl | 4-imidazoyl-methyl |
| 3-carboxypropyl | 2-butyl | 2-butyl | 4-aminobutyl |
| ethyl | benzyl | 2-methylpropyl | 3-guanylpropyl |
| benzyl | 4-hydroxyphenyl | 4-aminobutyl | 4-imidazoyl-methyl |
| phenethyl | 4-methoxyphenyl | 3-guanylpropyl | 4-aminobutyl |
| 4-hydroxyphenethyl | 4-methoxyphenyl | 4-imidazoyl-methyl | 3-guanylpropyl |
| 2-(4-imidazolyl)-ethyl | 4-hydroxyphenyl | benzyl | 4-imidazoyl-methyl |
| 3-carboxypropyl | benzyl | 4-hydroxyphenyl-methyl | 4-aminobutyl |
| ethyl | 2-butyl | 3-indoylmethyl | 3-guanylpropyl |
| benzyl | 2-butyl | 4-methoxyphenyl-methyl | 4-imidazoyl-methyl |
| phenethyl | benzyl | phenylethyl | 4-aminobutyl |
| 4-hydroxyphenethyl | 4-hydroxyphenyl | hydrogen | thiolmethyl |
| 2-(4-imidazolyl)-ethyl | 4-methoxyphenyl | methyl | methylthioethyl |
| 3-carboxypropyl | 2-butyl | 2-propyl | hydroxymethyl |
| ethyl | benzyl | 2-butyl | 1-hydroxyethyl |
| benzyl | 4-hydroxyphenyl | 2-methylpropyl | thiolmethyl |
| phenethyl | 4-methoxyphenyl | 4-aminobutyl | methylthioethyl |
| 4-hydroxyphenethyl | 4-hydroxyphenyl | 3-guanylpropyl | hydroxymethyl |
| 2-(4-imidazolyl)-ethyl | benzyl | 4-imidazoyl-methyl | 1-hydroxyethyl |
| 3-carboxypropyl | 2-butyl | benzyl | thiolmethyl |
| ethyl | 2-butyl | 4-hydroxyphenyl-methyl | methylthioethyl |
| benzyl | benzyl | 3-indoylmethyl | hydroxymethyl |
| phenethyl | 4-hydroxyphenyl | 4-methoxyphenyl-methyl | 1-hydroxyethyl |
| 4-hydroxyphenethyl | 4-methoxyphenyl | phenylethyl | hydroxymethyl |

EXAMPLE 10

PREPARATION OF ISOBUTYLMALONIC ACID

10A. Formula 12 Where $R^2$ Is 2-Methylpropyl

To a solution of NaOEt prepared by dissolving 5.75 g (0.25 mol) of Na in 150 mL of absolute EtOH was added 39 mL (0.250 mol) of diethyl malonate with cooling in a water bath under $N_2$. To the resulting solution was added 24 mL (0.250 mol) of isobutyl bromide. The mixture was refluxed under $N_2$ for 14 hours. The ethanol was evaporated under reduced pressure and the residue was partitioned between $CHCl_3$ and water. The aqueous $Na_2SO_4$ and evaporated. The residue was distilled under reduced pressure to give 47.2 g (0.219 mol, 88% of diethyl isobutylmalonate as a colorless liquid. Characteristic analytical data are as follows: bp 127°–135° C. (25 mm Hg); $^1$H NMR (300 MHz, $CDCL_3$) δ4.20 (q, J=7 Hz, 4H), 3,41 (t, J=8 Hz, 1H), 1.80 (t, J=7 Hz, 2H), 1.57 (m, 1H), 1.27 (t, J=8 Hz, 6H), 0.92 (d, J=7 Hz, 6H).

To a solution of 8.34 g (38.6 mmol) of diethyl isobutylmalonate in 35 mL of 95% EtOH was added a solution of 9.0 g (161 mmol) of KOH in 110 mL of 95% EtOH. The mixture was stirred at 25° C. for 16 hours and then at reflux for 1 hour. The mixture was cooled, diluted with water and extracted with $CH_3Cl$. The aqueous layer was cooled to 0° C. and acidified to pH<1 with 30 mL of concentrated HCl, then it was extracted with $CHCl_3$. The aqueous layer was further continuously extracted with $CHCl_3$ overnight. The combined organic extracts were dried over anhydrous $Na_2SO_4$ and evaporated to afford 5.44 g (33.9 mmol, 88%) of isobutylmalonic acid as a solid which was essentially pure according to $^1$H NMR and which was used without further purification. Characteristic analytical data are as follows: mp 108°–110° C.; $^1$H NMR (300 MHz, $CDCl_3$) δ3.52 (t, J=8 Hz, 1H), 1.84 (t, J=8 Hz, 2H), 1.66 (m, 1H), 0.94 (d, J-7 Hz, 6H); $^{13}$C NMR (75 MHz, $CDCl_3$) δ175.6 (C=O), 49.7 (CH), 37.1 ($CH_2$), 25.7 (CH), 21.7 ($CH_3$).

10B. Formula 12 Where $R^2$ Is 4-Methoxyphenylmethyl

By following the procedures described in Example 10A, crude diethyl 4-methoxyphenylmethylmalonate was obtained (100% yield) and converted to 4-methoxyphenylmethylmalonic acid (69% yield). Characteristic analytical data for the crude diethyl 4-methoxyphenylmethylmalonate are as follows: $^1$H NMR (300 MHz, $CDCl_3$) δ7.13 (d, J=9 Hz, 2H), 6.81 (d, J=9 Hz, 2H), 4.13 (q, J=7 Hz, 4H), 3.78 (s, 3H), 3.60 (t, J=8 Hz, 1H), 3.16 (d, J=5 Hz, 2H), 1.21 (t, J=7 Hz, 6H). Characteristic analytical data for the 4-methoxyphenylmethylmalonic acid are as follows: $^1$H NMR (300 MHz, $CDCl_3$) δ7.12 (d, J=9 Hz, 2H), 6.79 (d, J=9 Hz, 2H), 3.74 (s, 3H), 3.58 (t, J=8 Hz, 1H), 3.48 (br s, 2H), 3.14 (d, J=7 Hz, 2H).

10C. Formula 12 Varying $R^2$

By following the procedures described in Example 10A and substituting isobutyl bromide with other compounds of Formula 12A (where the $R^2$ substituents are as indicated in the table below) there are obtained the corresponding substituted compounds of Formula 12.

Formula 12

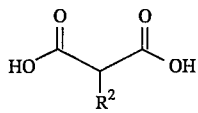

| $R^2$ | Name |
|---|---|
| H | malonic acid |
| methyl | methylmalonic acid |
| 2-propyl | 2-propylmalonic acid |
| 2-butyl | 2-butylmalonic acid |
| benzyl | benzylmalonic acid |
| blocked 4-hydroxyphenylmethyl | 4-hydroxyphenylmethylmalonic acid |
| blocked 3-indolylmethyl | 3-indolylmethylmalonic acid |
| phenylethyl | phenylethylmalonic acid |
| blocked 4-aminobutyl | 4-aminobutylmalonic acid |
| blocked 3-guanylpropyl | 3-guanylpropylmalonic acid |
| blocked 4-imidazoylmethyl | 4-imidazoylmethylmalonic acid |
| methylthioethyl | methylthioethylmalonic acid |

EXAMPLE 11

PREPARATION OF 4-METHYL-2-METHYLENEPENTANOIC ACID

11A. Formula 13 Where $R^2$ Is 2-Methylpropyl

To a stirred mixture of 14.0 g of isobutylmalonic acid and 37 mL of 37% formalin was added 9.05 mL of diethylamine at room temperature. The mixture was stirred at room temperature for 3 h and refluxed for an additional 2 h. The reaction mixture was cooled to room temperature and diluted with $CHCl_3$, and extracted with saturated aqueous $NaHCO_3$. The aqueous layer was acidified with 1M HCl and extracted with $CHCl_3$. The organic extract was dried over anhydrous $Na_2SO_4$ and evaporated under reduced pressure to afford 11.0 g at 98% yield of 4-methyl-2-methylenepentanoic acid as a clear liquid which was used without further purification. Characteristic analytical data are as follows: $^1$H NMR (300 MHz, $CDCl_3$) δ6.32 (d, J=2 Hz, 1H), 5.62 (d, J=2 Hz, 1H), 2.17 (dd, J=1, 7 Hz, 2H), 1.82 (m, 1H), 0.90 (d, J=7 Hz, 6H); $^{13}$C NMR (300 MHz) δ173.6, 139.4, 128.4, 40.7, 26.9, 22.0.

11B. Formula 13 Where $R^2$ Is 4-Methoxyphenylmethyl

By following the procedures described in Example 11A and substituting isobutylmalonic acid with (4-methoxybenzyl)malonic acid, 5.6 g (58% yield) of 3-(4-methoxyphenyl)-2-methylenepropanoic acid was obtained. Characteristic analytical data are as follows: $^1$H NMR (300 MHz, $CDCl_3$) δ7.10 (d, J=9 Hz, 2H), 6.82 (d, J=9 Hz, 2H), 6.26 (br s, 1H), 5.48 (br s, 1H), 3.77 (s, 3H), 3.54 (s, 2H).

11C. Formula 13 Varying $R^2$

By following the procedures described in Example 11A and substituting isobutylmalonic acid with other compounds of Formula 12 (where the $R^2$ substituents are as indicated in the table below) there are obtained the corresponding substituted compounds of Formula 13.

Formula 13

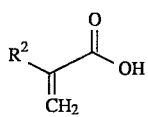

| $R^2$ | Name |
|---|---|
| H | 2-propenoic acid |
| methyl | 2-methylenepropanoic acid |
| 2-propyl | 3-methyl-2-methylene-butanoic acid |

Formula 13

$$R^2\underset{CH_2}{\overset{O}{\diagdown}}OH$$

| R² | Name |
|---|---|
| 2-butyl | 3-methyl-2-methylene-pentanoic acid |
| benzyl | 3-phenyl-2-methylene-propanoic acid |
| blocked 4-hydroxyphenylmethyl | 3-(4-hydroxyphenyl)-2-methylene-propanoic acid |
| blocked 3-indolylmethyl | 3-(3-indolyl)-2-methylene-propanoic acid |
| phenylethyl | 4-phenyl-2-methylene-butanoic acid |
| blocked 4-aminobutyl | 6-amino-2-methylene-hexanoic acid |
| blocked 3-guanylpropyl | 5-guanyl-2-methylene-pentanoic acid |
| blocked 4-imidazoylmethyl | 3-(4-imidazoyl)-2-methylene-propanoic acid |

EXAMPLE 12

PREPARATION OF AcS-(CH₂-DL-Leu)-OH

12A. Formula 15 Where R² Is 2-Methylpropyl

A mixture of 0.700 g of 4-methyl-2-methylenepentanoic acid and 0.90 mL (0.96 g) of thiolacetic acid was stirred under nitrogen for 26 h. The excess thiolacetic acid was removed by evaporation on the rotary evaporator with warming to give 1.10 g (99% yield) of AcS-(CH₂-DL-Leu)-OH. Characteristic analytical data are as follows: mp 38°–40° C. [mp reported in literature mp 42°–47° C. (Sundeen, J. E.; Dejneka, T. U.S. Pat. No. 4,382,081, 1983; *Chem. Abstr.* 1983, 98, 179923b); and mp 46°–47° C. (Darlak, K.; Miller, R. B.; Stack, M. S.; Spatola, A. F.; Gray, R. D. *J. Biol. Chem.* 1990, 265, 5199–5205); ¹H NMR (300 MHz, CDCl₃) δ3.14 (dd, J=6, 14 Hz, 1H), 2.97 (dd, J=9, 14 Hz, 1H), 2.68 (m, 1H), 2.33 (s, 3H), 1.64 (m, 2H), 1.39 (m, 1H), 0.93 (d, J=6 Hz, 3H), 0.92 (d J=6 Hz, 3H).

12B. Formula 15 Where R² Is 4-Methoxyphenylmethyl

By following the procedures described in Example 12A and substituting 4-methyl-2-methylenepentanoic acid with 3-(4-methoxyphenyl)-2-methylenepropanoic acid, 6.4 g (95% yield) of AcS-(CH₂-DL-TyrOMe)-OH as a gum was obtained. Characteristic analytical data are as follows: ¹H NMR (300 MHz, CDCl₃) δ7.08 (d, J=9 Hz, 2H), 6.80 (d, J=9 Hz, 2H), 3.76 (s, 3H), 2.77–3.12 (m, 5H), 2.29 (s, 3H).

12C. Formula 15 Varying R²

By following the procedures described in Example 12A and substituting 4-methyl-2-methylenepentanoic acid with other compounds of Formula 13 (where the R² substituents are as indicated in the table below) there are obtained the corresponding substituted compounds of Formula 15.

Formula 15

$$H_3C\underset{}{\overset{O}{\diagdown}}S\underset{R^2}{\overset{DL}{\diagdown}}\overset{O}{\diagdown}OH$$

| R² | Name |
|---|---|
| H | AcS—(CH₂-DL-Gly)—OH |
| methyl | AcS—(CH₂-DL-Ala)—OH |
| 2-propyl | AcS—(CH₂-DL-Val)—OH |
| 2-butyl | AcS—(CH₂-DL-Ile)—OH |
| benzyl | AcS—(CH₂-DL-Phe)—OH |
| blocked 4-hydroxyphenylmethyl | AcS—(CH₂-DL-Tyr)—OH |
| blocked 3-indolylmethyl | AcS—(CH₂-DL-Trp)—OH |
| phenylethyl | AcS—(CH₂-DL-Phet)—OH |
| blocked 4-aminobutyl | AcS—(CH₂-DL-Lys)—OH |
| blocked 3-guanylpropyl | AcS—(CH₂-DL-Arg)—OH |
| blocked 4-imidazoylmethyl | AcS—(CH₂-DL-His)—OH |

EXAMPLE 13

PREPARATION OF HS-(CH₂-DL-Leu)-OH

13A. Formula 16 Where R² Is 2-Methylpropyl

A solution of 2.0 g of AcS-(CH₂-DL-Leu)-OH in 5 mL of conc. NH₄H was stirred at 25° C. for 1 h. The reaction mixture was acidified to pH 4–5 by addition of 1M HCl, and extracted with CH₂Cl₂. The organic layer was dried over Na₂SO₄ and evaporated to give 1.35 g (85% yield) of HS-(CH₂-DL-Leu)-OH. Characteristic analytical data are as follows: ¹H NMR (300 MHz, CDCl₃) δ2.6–2.8 (m, 3H), 1.64 (m, 2H), 1.55 (t, J=7 Hz, 1H, SH), 1.44 (m, 1H), 0.95 (d, J=7 Hz, 3H), 0.92 (d, J=7 Hz, 3H).

13B. Formula 16 Where R² Is 4-Methoxyphenylmethyl

By following the procedures described in Example 13A and substituting AcS-(CH₂-DL-Leu)-OH with AcS-(CH₂-DL-TyrOCH₃)-OH, 2.2 g (9.7 mmol) of HS-(CH₂-DL-Tyr OMe)-OH was obtained.

13C. Formula 16 Varying R²

By following the procedures described in Example 13A and substituting AcS-(CH₂-DL-Leu)-OH with other compounds of Formula 15 (where the R² substituents are as indicated in the table below) there are obtained the corresponding substituted compounds of Formula 16.

Formula 16

$$HS\underset{R^2}{\overset{DL}{\diagdown}}\overset{O}{\diagdown}OH$$

| R² | Name |
|---|---|
| H | HS—(CH₂-DL-Gly)—OH |
| methyl | HS—(CH₂-DL-Ala)—OH |
| 2-propyl | HS—(CH₂-DL-Val)—OH |
| 2-butyl | HS—(CH₂-DL-Ile)—OH |
| benzyl | HS—(CH₂-DL-Phe)—OH |
| blocked 4-hydroxyphenylmethyl | HS—(CH₂-DL-Tyr)—OH |
| blocked 3-indolylmethyl | HS—(CH₂-DL-Trp)—OH |

-continued

Formula 16

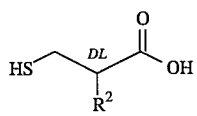

| R² | Name |
|---|---|
| phenylethyl | HS—(CH₂-DL-Phet)—OH |
| blocked 4-aminobutyl | HS—(CH₂-DL-Lys)—OH |
| blocked 3-guanylpropyl | HS—(CH₂-DL-Arg)—OH |
| blocked 4-imidazoylmethyl | HS—(CH₂-DL-His)—OH |

EXAMPLE 14

PREPARATION OF MeS-(CH₂-DL-Leu)-OH

14A. Formula 17 Where R¹ Is Methyl and R² Is 2-Methylpropyl

To a solution of 240 mg of Na in 8 mL of MeOH, was added 672 mg of HS-(CH₂-DL-Leu)-OH and 0.322 mL of CH₃I. The mixture was stirred at 25° C. for 8 h. Water was added and the mixture was acidified with acetic acid and extracted with EtOAc. The organic layer was dried and evaporated to give 639 mg (88% yield) of MsS-(CH₂-DL-Leu)-OH. Characteristic analytical data are as follows: ¹H NMR (300 MHz, CDCl₃) δ2.73 (m, 2H), 2.59 (m, 1H), 2.12 (s, 3H), 1.63 (m, 2H), 1.43 (m, 1H), 0.94 (d, J=6 Hz, 3H), 0.92 (d, J=6 Hz, 3H).

14B. Formula 17 Where R¹ Is n-butyl and R² Is 2-Methylpropyl

By following the procedures described in Example 14A and substituting CH₃I with n-butyl iodide, 1.78 g (95% yield) of n-BuS-(CH₂-DL-Leu)-OH was obtained. Characteristic analytical data are as follows: ¹H NMR (300 MHz, CDCl₃) δ2.57–2.77 (m, 3H), 2.54 (t, J=7 Hz, 2H), 1.52–1.72 (m, 4H), 1.34–1.48 (m, 3H), 0.94 (d, J=6 Hz, 3H), 0.92 (d, J=6 Hz, 3H), 0.91 (t, J=7 Hz, 3H).

14C. Formula 17 Where R¹ is n-Butyl and R² Is 4-Methoxyphenylmethyl

By following the procedures described in Example 14A and substituting HS-(CH₂-DL-Leu)-OH with HS-(CH₂-DL-TyrOCH₃)-OH, and CH₃I with n-butyl iodide, 2.50 g (90% yield) of n-BuS-(CH₂-DL-TyrOMe)-OH was obtained. Characteristic analytical data are as follows: ¹H NMR (300 MHz, CDCl₃) δ7.10 (d, J=9 Hz, 2H), 6.82 (d, J=9 Hz, 2H), 3.78 (s, 3H), 2.72–3.02 (m, 4H), 2.62 (dd, J=5, 13 Hz, 1H), 2.48 (t, J=7 Hz, 2H), 1.50 (m, 2H), 1.38 (m, 2H), 0.88 (t, J=7 Hz, 3H).

14D. Formula 17 Varying R¹ and R²

By following the procedures described in Example 14A and substituting CH₃I with other compounds of Formula 9 (e.g., compounds with R¹) and HS-(CH₂-DL-Leu)-OH with other compounds of Formula 16 (e.g., compounds with R² that are prepared according to Example 13A and exemplified in Example 13B) there are obtained the correspondingly substituted of compounds of Formula 17.

Formula 17

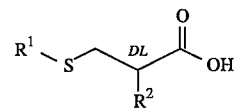

| R¹ | R² | Name |
|---|---|---|
| ethyl | H | EtS—(CH₂-DL-Gly)—OH |
| benzyl | methyl | BnS—(CH₂-DL-Ala)—OH |
| phenethyl | 2-propyl | PhetS—(CH₂-DL-Val)—OH |
| blocked 4-hydroxyphenethyl | 2-butyl | (4-hydroxyphenethyl)S—(CH₂-DL-Ile)—OH |
| blocked 2-(4-imidazolyl)ethyl | benzyl | 2(4-imidazolyl)ethylS—(CH₂-DL-Phe)—OH |
| blocked 3-carboxypropyl | blocked 4-hydroxyphenylmethyl | (3-carboxypropyl)S—(CH₂-DL-Tyr)—OH |
| ethyl | 4-methoxyphenylmethyl | EtS—(CH₂-DL-TyrOCH₃)—OH |
| benzyl | blocked 3-indolylmethyl | BnS—(CH₂-DL-Trp)—OH |
| phenethyl | phenylethyl | PhetS—(CH₂-DL-Phet)—OH |
| blocked 4-hydroxyphenethyl | blocked 4-aminobutyl | (4-hydroxyphenethyl)-S—(CH₂-DL-Lys)—OH |
| blocked 2-(4-imidazolyl)ethyl | blocked 3-guanylpropyl | 2-(4-imidazolyl)ethylS—(CH₂-DL-Arg)—OH |
| blocked 3-carboxypropyl | blocked 4 imidazoylmethyl | 3-carboxypropylS—(CH₂-DL-His)—OH |
| ethyl | H | EtS—(CH₂-DL-Gly)—OH |
| benzyl | methyl | BnS—(CH₂-DL-Ala)—OH |
| phenethyl | 2-propyl | PhetS—(CH₂-DL-Val)—OH |
| blocked 4-hydroxyphenethyl | 2-butyl | 4-hydroxyphenethylS—(CH₂-DL-Ile)—OH |
| blocked 2-(4-imidazolyl)ethyl | benzyl | 2-(4-imidazolyl)ethylS—(CH₂-DL-Phe)—OH |
| blocked 3-carboxypropyl | blocked 4-hydroxyphenylmethyl | 3-carboxypropylS—(CH₂-DL-Tyr)—OH |
| ethyl | blocked 3-indolylmethyl | EtS—(CH₂-DL-Trp)—OH |
| benzyl | phenylethyl | BnS—(CH₂-DL-Phet)—OH |
| phenethyl | blocked 4-aminobutyl | PhetS—(CH₂-DL-Lys)—OH |
| blocked 4-hydroxy- | blocked 3-guanylpropyl | (4-hydroxyphenethyl)S— |

Formula 17

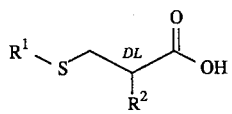

| R¹ | R² | Name |
|---|---|---|
| phenethyl | | (CH₂-DL-Arg)—OH |
| blocked 2-(4-imidazolyl)ethyl | blocked 4-imidazoylmethyl | 2-(4-imidazolyl)ethylS—(CH₂-DL-His)—OH |
| blocked 3-carboxypropyl | H | 3-carboxypropylS—(CH₂-DL-Gly)—OH |
| ethyl | methyl | EtS—(CH₂-DL-Ala)—OH |
| benzyl | 2-propyl | BnS—(CH₂-DL-Val)—OH |
| phenethyl | 2-butyl | PhetS—(CH₂-DL-Ile)—OH |
| blocked 4-hydroxyphenethyl | benzyl | 4-hydroxyphenethylS—(CH₂-DL-Phe)—OH |
| blocked 2-(4-imidazolyl)ethyl | blocked 4-hydroxyphenylmethyl | 2-(4-imidazolyl)ethylS—(CH₂-DL-Tyr)—OH |
| blocked 3-carboxypropyl | blocked 3-indolylmethyl | 3-carboxypropylS—(CH₂-DL-Trp)—OH |
| ethyl | phenylethyl | EtS—(CH₂-DL-Phet)—OH |
| benzyl | blocked 4-aminobutyl | BnS—(CH₂-DL-Lys)—OH |
| phenethyl | blocked 3-guanylpropyl | PhetS—(CH₂-DL-Arg)—OH |
| blocked 4-hydroxyphenethyl | blocked 4-imidazoylmethyl | 4-hydroxyphenethylS—(CH₂-DL-His)—OH |
| blocked 2-(4-imidazolyl)ethyl | H | 2-(4-imidazolyl)ethylS—(CH₂-DL-Gly)—OH |
| blocked 3-carboxypropyl | methyl | 3-carboxypropylS—(CH₂-DL-Ala)—OH |
| ethyl | 2-propyl | EtS—(CH₂-DL-Val)—OH |
| benzyl | 2-butyl | BnS—(CH₂-DL-Ile)—OH |
| phenethyl | benzyl | PhetS—(CH₂-DL-Phe)—OH |
| blocked 4-hydroxyphenethyl | blocked 4-hydroxyphenylmethyl | 4-hydroxyphenethylS—(CH₂-DL-Tyr)—OH |
| blocked 2-(4-imidazolyl)ethyl | blocked 3-indolylmethyl | 2-(4-imidazolyl)ethyS—(CH₂-DL-Trp)—OH |
| blocked 3-carboxypropyl | phenylethyl | 3-carboxypropylS—(CH₂-DL-Phet)—OH |

EXAMPLE 15

PREPARATION OF MsS-(CH₂-DL-Leu-CH₂)-OH

15A. Formula 18 Where R¹ Is Methyl and R² Is 2-Methylpropyl

To a solution of 639 mg of MeS-(CH₂-DL-Leu)-OH in 10 mL of THF at 0° C., was added 10 mL of 1M BH₃ in THF dropwise over a period of 15 min with stirring. After completion of the addition, the stirring was continued for another 15 min at the same temperature. The mixture was allowed to warm to room temperature and was stirred for 3 h. The reaction mixture was cooled in an ice bath and was quenched by dropwise addition of water. The mixture was partitioned between water and EtOAc. The organic layer was washed with saturated NaHCO₃ and dried over Na₂SO₄. The solvent was removed by evaporation and the residue was purified by flash chromatography (5% EtOAc in hexane) to give 418 mg (71% yield) of MeS-(CH₂-DL-Leu-CH₂)-OH. Characteristic analytical data are as follows: ¹H NMR (300 MHz, CDCl₃) δ3.70 (dd, J=4, 11 Hz, 1H), 3.60 (dd, J=6, 11 Hz, 1H), 2.57 (dd, J=5, 13 Hz, 1H), 2.53 (dd, J=7, 13 Hz, 1H), 2.12 (s, 3H), 1.87 (m, 2H), 1.63 (m, 1H), 1.21 (m, 2H), 0.89 (d, J=7 Hz, 3H), 0.88 (d, J=7 Hz, 3H).

15B. Formula 18 Where R¹ Is n-butyl and R² Is 2-Methylpropyl

By following the procedures described in Example 15A and substituting MeS-(CH₂-DL-Leu)-OH with n-BuS-(CH₂-DL-Leu)-OH, 1.76 g (81% yield) of n-BuS(CH₂-DL-Leu-CH₂)-OH was obtained as an oil. Characteristic analytical data are as follows: 1H NMR (300 MHz, CDCl₃) δ3.71 (dd, J=4, 11 Hz, 1H), 3.61 (dd, J=7, 11 Hz, 1H), 2.63 (dd, J=5, 14 Hz, 1H), 2.55 (dd, J=7, 14 Hz, 1H), 2.54 (t, J=7 Hz, 2H), 1.85 (m, 2H), 1.72–1.53 (m, 3H), 1.41 (m, 2H), 1.21(t, J=7 Hz, 2H), 0.92 (t, J=7 Hz, 3H), 0.91 (d, J=7 Hz, 3H), 0.90 (d, J=7 Hz, 3H).

15C. Formula 18 Where R¹ Is n-butyl and R² Is 4-Methoxyphenylmethyl

By following the procedures described in Example 15A and substituting MeS-(CH₂-DL-Leu)-OH with n-BuS-(CH₂-DL-TyrOMe)-OH, 1.65 g (69% yield) of n-BuS-(CH₂-DL-TyrOMe-CH₂)-OH was obtained as an oil. Characteristic analytical data are as follows: ¹H NMR (300 MHz, CDCl₃) δ7.1 (d, J=9 Hz, 2H), 6.83 (d, J=9 Hz, 2H), 3.78 (s, 3H), 3.5–3.7 (m, 2H), 2.64 (d, J=7 Hz, 2H), 2.55 (d, J=7 Hz, 2H), 2.47 (t, J=8 Hz, 2H), 2.02 (m, 2H), 1.52 (m, 1.39 (m, 2H), 0.89 (t, J=7 Hz, 3H).

15D. Formula 18 Varying R¹, R² and R³

By following the procedures described in Example 15A and substituting MeS-(CH₂-DL-Leu)-OH with other compounds of Formula 17 (where R¹, R² and R³ are as indicated in the table below) there are obtained the corresponding substituted compounds of Formula 18.

Formula 18

$$R^1\text{—}S\text{—}CH_2\text{—}\underset{R^2}{\overset{DL}{C}H}\text{—}CH_2\text{—}OH$$

| R¹ | R² | Name |
|---|---|---|
| ethyl | H | EtS—(CH₂-DL-Gly—CH₂)—OH |
| benzyl | methyl | BnS—(CH₂-DL-Ala—CH₂)—OH |
| phenethyl | 2-propyl | PhetS—(CH₂-DL-Val—CH₂)—OH |
| blocked 4-hydroxy-phenethyl | 2-butyl | (4-hydroxyphenethyl)S-(CH₂-DL-Ile—CH₂)—OH |
| blocked 2-(4-imidazolyl)ethyl | benzyl | 2(4-imidazolyl)ethylS—(CH₂-DL-Phe—CH₂)—OH |
| blocked 3-carboxy-propyl | blocked 4-hydroxyphenylmethyl | (3-carboxypropyl)S—(CH₂-DL-Tyr—CH₂)—OH |
| ethyl | 4-methoxyphenylmethyl | EtS—(CH₂-DL-TyrOCH₃—CH₂)—OH |
| benzyl | blocked 3-indolylmethyl | BnS—(CH₂-DL-Trp—CH₂—OH |
| phenethyl | phenylethyl | PhetS—(CH₂-DL-Phet—CH₂)—OH |
| blocked 4-hydroxy-phenethyl | blocked 4-aminobutyl | (4-hydroxyphenethyl)-S—(CH₂-DL-Lys—CH₂)—OH |
| blocked 2-(4-imidazolyl)ethyl | blocked 3-guanylpropyl | 2-(4-imidazolyl)ethylS—(CH₂-DL-Arg—CH₂)—OH |
| blocked 3-carboxy-propyl | blocked 4-imidazoylmethyl | 3-carboxypropylS—(CH₂-DL-His—CH₂)—OH |
| ethyl | H | EtS—(CH₂-DL-Gly—CH₂)—OH |
| benzyl | methyl | BnS—(CH₂-DL-Ala—CH₂)—OH |
| phenethyl | 2-propyl | PhetS—(CH₂-DL-Val—CH₂)—OH |
| blocked 4-hydroxy-phenethyl | 2-butyl | 4-hydroxyphenethylS—(CH₂-DL-Ile—CH₂)—OH |
| blocked 2-(4-imidazolyl)ethyl | benzyl | 2-(4-imidazolyl)ethylS—(CH₂-DL-Phe—CH₂)—OH |
| blocked 3-carboxy-propyl | blocked 4-hydroxyphenylmethyl | 3-carboxypropylS—(CH₂-DL-Tyr—CH₂)—OH |
| ethyl | blocked 3-indolylmethyl | EtS—(CH₂-DL-Trp—CH₂)—OH |
| benzyl | phenylethyl | BnS—(CH₂-DL-Phet—CH₂)—OH |
| phenethyl | blocked 4-aminobutyl | PhetS—(CH₂-DL-Lys—CH₂)—OH |
| blocked 4-hydroxy-phenethyl | blocked 3-guanylpropyl | (4-hydroxyphenethyl)S—(CH₂-DL-Arg—CH₂)—OH |
| blocked 2-(4-imidazolyl)ethyl | blocked 4-imidazoylmethyl | 2-(4-imidazolyl)ethylS—(CH₂-DL-His—CH₂)—OH |
| blocked 3-carboxy-propyl | H | 3-carboxypropylS—(CH₂-DL-Gly—CH₂)—OH |
| ethyl | methyl | EtS—(CH₂-DL-Ala—CH₂)—OH |
| benzyl | 2-propyl | BnS—(CH₂-DL-Val—CH₂)—OH |
| phenethyl | 2-butyl | PhetS—(CH₂-DL-Ile—CH₂)—OH |
| blocked 4-hydroxy-phenethyl | benzyl | 4-hydroxyphenethylS—(CH₂—DL-Phe—CH₂)—OH |
| blocked 2-(4-imidazolyl)ethyl | blocked 4-hydroxyphenylmethyl | 2-(4-imidazolyl)ethylS—(CH₂-DL-Tyr—CH₂)—OH |
| blocked 3-carboxy-propyl | blocked 3-indolylmethyl | 3-carboxypropylS—(CH₂-DL-Trp—CH₂)—OH |
| ethyl | phenylethyl | EtS—(CH₂-DL-Phet—CH₂)—OH |
| benzyl | blocked 4-aminobutyl | BnS—(CH₂-DL-Lys—CH₂)—OH |
| phenethyl | blocked 3-guanylpropyl | PhetS—(CH₂-DL-Arg—CH₂)—OH |
| blocked 4-hydroxy-phenethyl | blocked 4-imidazoylmethyl | 4-hydroxyphenethylS—(CH₂—DL-His—CH₂)—OH |
| blocked 2-(4-imidazolyl)ethyl | H | 2-(4-imidazolyl)ethylS—(CH₂-DL-Gly—CH₂)—OH |
| blocked 3-carboxy-propyl | methyl | 3-carboxypropylS—(CH₂-DL-Ala—CH₂)—OH |
| ethyl | 2-propyl | EtS—(CH₂-DL-Val—CH₂)—OH |
| benzyl | 2-butyl | BnS—(CH₂-DL-Ile—CH₂)—OH |
| phenethyl | benzyl | PhetS—(CH₂-DL-Phe—CH₂)—OH |
| blocked 4-hydroxy-phenethyl | blocked 4-hydroxyphenylmethyl | 4-hydroxyphenethylS—(CH₂-DL-Tyr—CH₂)—OH |
| blocked 2-(4-imidazolyl)ethyl | blocked 3-indolylmethyl | 2-(4-imidazolyl)ethylS—(CH₂-DL-Trp—CH₂)—OH |
| blocked 3-carboxy-propyl | phenylethyl | 3-carboxypropylS—(CH₂-DL-Phet—CH₂)—OH |

EXAMPLE 16

PREPARATION OF MeS-(CH$_2$-DL-Leu-CH$_2$)-OTBS

16A. Formula 19 Where R$^1$ Is Methyl and R$^2$ Is 2-Methylpropyl

To a solution of 418 mg of MeS-(CH$_2$-DL-Leu-CH$_2$)-OH in 2 mL of DMF, was added 431 mg of imidazole and 451 mg of t-butyldimethylsilyl chloride. The mixture was stirred at room temperature for 7 h. The mixture was partitioned between Et$_2$O and water and the organic layer was washed with water, dried, and evaporated under vacuum. The residue was purified by flash chromatography on silica gel (5% EtOAc in hexane) to give 570 mg (80% yield) of MeS-(CH$_2$-DL-Leu-CH$_2$)-OTBS as an oil. Characteristic analytical data are as follows: $^1$H NMR (300 MHz, CDCl$_3$) δ3.61 (dd, J=5, 10 Hz, 1H), 3.52 (dd, J=6, 10 Hz, 1H), 2.59 (dd, J=7, 13 Hz, 1H), 2.43 (dd, J=6, 13 Hz, 1H), 2.07 (s, 3H), 1.74 (m, 1H), 1.64 (m, 1H), 1.20 (m, 2H), 0.89–0.85 (m, 15H), 0.06 (s, 6H).

16B. Formula 19 Where R$^1$ Is n-butyl and R$^2$ Is 2-Methylpropyl

By following the procedures described in Example 16A and substituting MeS-(CH$_2$-DL-Leu-CH$_2$)-OH with n-BuS-(CH$_2$-DL-Leu-CH$_2$)-OH, 2.16 g (79% yield) of n-BuS-(CH$_2$-DL-Leu-CH$_2$)-OTBS was obtained as an oil. Characteristic analytical data are as follows: $^1$H NMR (300 MHz, CDCl$_3$) δ3.62 (dd, J=4, 10 Hz, 1H), 3.52 (dd, J=6, 10 Hz, 1H), 2.62 (dd, J=7, 13 Hz, 1H), 2.40–2.52 (m, 3H), 1.51–1.78 (m, 4H), 1.41 (m, 2H), 1.21 (dt, J=2, 7 Hz, 2H), 0.91 (t, J=7 Hz, 3H), 0.89 (s, 9H), 0.89 (d, J=7 Hz, 3H), 0.88 (d, J=7 Hz, 3H), 0.04 (s, 6H).

16C. Formula 19 Where R$^1$ Is n-butyl and R$^2$ Is 4-Methoxyphenylmethyl

By following the procedures described in Example 16A and substituting MeS-(CH$_2$-DL-Leu-CH$_2$)-OH with MeS-(CH$_2$-DL-TyrOCH$_3$-CH$_2$)-OH, 1.94 g (85% yield) of n-BuS-(CH$_2$-DL-TyrOMe-CH$_2$)-OTBS was obtained as an oil. Characteristic analytical data are as follows: $^1$H NMR (300 MHz, CDCl$_3$) δ7.10 (d, J=9 Hz, 2H), 6.82 (d, J=9 Hz, 2H), 3.78 (s, 3H), 3.58 (dd, J=5, 10 Hz, 1H), 3.51 J=5, 10 Hz, 1H), 2.62 (dd, J=4, 7 Hz, 2H), 2.55 (dd, J=7, 13 Hz, 1H), 2.44. (3), 1.84 (m, 1H), 1.50 (m, 2H), 1.38 (m, 2H), 0.89 (s, 9H), 0.88 (t, J=7 Hz, 3H), 0.02 (s, 6H).

16D. Formula 19 Varying R$^1$, R$^2$ and R$^3$

By following the procedures described in Example 16A and substituting MeS-(CH$_2$-DL-Leu-CH$_2$)-OH with other compounds of Formula 18 (where R$^1$, R$^2$ and R$^3$ are as indicated in the table below) there are obtained the corresponding substituted compounds of Formula 19.

Formula 19

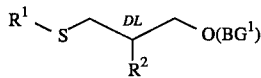

| R$^1$ | R$^2$ | Name |
|---|---|---|
| ethyl | H | EtS—(CH$_2$-DL-Gly—CH$_2$)—OTBS |
| benzyl | methyl | BnS—(CH$_2$-DL-Ala—CH$_2$)—OTBS |
| phenethyl | 2-propyl | PhetS—(CH$_2$-DL-Val—CH$_2$)—OTBS |
| blocked 4-hydroxyphenethyl | 2-butyl | (4-hydroxyphenethyl)S—(CH$_2$-DL-Ile—CH$_2$)—OTBS |
| blocked 2-(4-imidazolyl)ethyl | benzyl | 2(4-imidazolyl)ethylS—(CH$_2$-DL-Phe—CH$_2$)—OTBS |
| blocked 3-carboxypropyl | blocked 4-hydroxyphenylmethyl | (3-carboxypropyl)S—(CH$_2$-DL-Tyr—CH$_2$)—OTBS |
| ethyl | 4-methoxyphenylmethyl | EtS—(CH$_2$-DL-TyrOCH$_3$—CH$_2$)—OTBS |
| benzyl | blocked 3-indolylmethyl | BnS—(CH$_2$-DL-Trp—CH$_2$)—OTBS |
| phenethyl | phenylethyl | PhetS—(CH$_2$-DL-Phet—CH$_2$)—OTBS |
| blocked 4-hydroxyphenethyl | blocked 4-aminobutyl | (4-hydroxyphenethyl)-S—(CH$_2$-DL-Lys—CH$_2$)—OTBS |
| blocked 2-(4-imidazolyl)ethyl | blocked 3-guanylpropyl | 2-(4-imidazolyl)ethylS—(CH$_2$-DL-Arg—CH$_2$)—OTBS |
| blocked 3-carboxypropyl | blocked 4-imidazoylmethyl | 3-carboxypropylS—(CH$_2$-DL-His—CH$_2$)—OTBS |
| ethyl | H | EtS—(CH$_2$-DL-Gly—CH$_2$)—OTBS |
| benzyl | methyl | BnS—(CH$_2$-DL-Ala—CH$_2$)—OTBS |
| phenethyl | 2-propyl | PhetS—(CH$_2$-DL-Val—CH$_2$)—OTBS |
| blocked 4-hydroxyphenethyl | 2-butyl | 4-hydroxyphenethylS—(CH$_2$-DL-Ile—CH$_2$)—OTBS |
| blocked 2-(4-imidazolyl)ethyl | benzyl | 2-(4-imidazolyl)ethylS—(CH$_2$-DL-Phe—CH$_2$)—OTBS |
| blocked 3-carboxypropyl | blocked 4-hydroxyphenylmethyl | 3-carboxypropylS—(CH$_2$-DL-Tyr—CH$_2$)—OTBS |
| ethyl | blocked 3-indolylmethyl | EtS—(CH$_2$-DL-Trp—CH$_2$)—OTBS |
| benzyl | phenylethyl | BnS—(CH$_2$-DL-Phet—CH$_2$)—OTBS |
| phenethyl | blocked 4-aminobutyl | PhetS—(CH$_2$-DL-Lys—CH$_2$)—OTBS |
| blocked 4-hydroxyphenethyl | blocked 3-guanylpropyl | (4-hydroxyphenethyl)S—(CH$_2$-DL-Arg—CH$_2$)—OTBS |
| blocked 2-(4- | blocked 4- | 2-(4-imidazolyl)ethylS— |

-continued

Formula 19

$$R^1\text{-}S\text{-}CH_2\text{-}\underset{R^2}{\overset{DL}{C}}\text{-}CH_2\text{-}O(BG^1)$$

| R¹ | R² | Name |
|---|---|---|
| imidazolyl)ethyl | imidazoylmethyl | (CH₂-DL-His—CH₂)—OTBS |
| blocked 3-carboxypropyl | H | 3-carboxypropylS—(CH₂-DL-Gly—CH₂)—OTBS |
| ethyl | methyl | EtS—(CH₂-DL-Ala—CH₂)—OTBS |
| benzyl | 2-propyl | BnS—(CH₂-DL-Val—CH₂)—OTBS |
| phenethyl | 2-butyl | PhetS—(CH₂-DL-Ile—CH₂)—OTBS |
| blocked 4-hydroxyphenethyl | benzyl | 4-hydroxyphenethylS—(CH₂-DL-Phe—CH₂)—OTBS |
| blocked 2-(4-imidazolyl)ethyl | blocked 4-hydroxyphenylmethyl | 2-(4-imidazolyl)ethylS—(CH₂-DL-Tyr—CH₂)—OTBS |
| blocked 3-carboxypropyl | blocked 3-indolylmethyl | 3-carboxypropyl S—(CH₂-DL-Trp—CH₂)—OTBS |
| ethyl | phenylethyl | EtS—(CH₂-DL-Phet—CH₂)—OTBS |
| benzyl | blocked 4-aminobutyl | BnS—(CH₂-DL-Lys—CH₂)—OTBS |
| phenethyl | blocked 3-guanylpropyl | PhetS—(CH₂-DL-Arg—CH₂)—OTBS |
| blocked 4-hydroxyphenethyl | blocked 4-imidazoylmethyl | 4-hydroxyphenethylS—(CH₂-DL-His—CH₂)—OTBS |
| blocked 2-(4-imidazolyl)ethyl | H | 2-(4-imidazolyl)ethylS—(CH₂-DL-Gly—CH₂)—OTBS |
| blocked 3-carboxypropyl | methyl | 3-carboxypropylS-(CH₂-DL-Ala—CH₂)—OTBS |
| ethyl | 2-propyl | EtS—(CH₂-DL-Val—CH₂)—OTBS |
| benzyl | 2-butyl | BnS—(CH₂-DL-Ile—CH₂)—OTBS |
| phenethyl | benzyl | PhetS—(CH₂-DL-Phe—CH₂)—OTBS |
| blocked 4-hydroxyphenethyl | blocked 4-hydroxyphenylmethyl | 4-hydroxyphenethylS—(CH₂-DL-Tyr—CH₂)—OTBS |
| blocked 2-(4-imidazolyl)ethyl | blocked 3-indolylmethyl | 2-(4-imidazolyl)ethylS—(CH₂-DL-Trp—CH₂)—OTBS |
| blocked 3-carboxypropyl | phenylethyl | 3-carboxypropylS—(CH₂-DL-Phet—CH₂)—OTBS |

EXAMPLE 17

PREPARATION OF MeS(NH)₂-(CH₂-DL-Leu-CH₂)-OTBS

17A. Formula 20 Where X Is NH, R¹ Is Methyl and R² Is 2-Methylpropyl

The sulfodiimine functionality was introduced using a modification of Mock's procedure [see Mock, W. L.; Tsay, J. T. *J. Am. Chem. Soc.* 1989, 111, 4467–4472]. To a stirred solution of 552 mg of MeS-(CH₂-DL-Leu-CH₂)-OTBS in 2 mL of anhydrous acetonitrile and 2 mL of anhydrous liquid ammonia (distilled from Na) at −55° C. under nitrogen was added a solution of 668 mg of N-chlorosuccinimide in 3 mL of acetonitrile dropwise over a period of 5 min. The reaction mixture was stirred at −55° C. for 30 min, then it was warmed to room temperature and stirring was continued overnight. The solvent was evaporated under vacuum and the residue was partitioned between 10% aqueous NaOH and CH₂Cl₂. The organic layer was dried over Na₂SO₄ and evaporated under vacuum. The residue was purified by flash chromatography (5% MeOH in CH₂Cl₂) to afford 95 mg (17% yield) of unreacted starting material and 273 mg (54% yield based on unrecovered starting material) of the sulfodiimine MeS (NH)₂-(CH₂-DL-Leu-CH₂)-OTBS as a gum. Characteristic analytical data are as follows: ¹H NMR (300 MHz, CDCl₃) δ3.77 (dd, J=4, 10 Hz, 1H), 3.55 (dd, J=5, 10 Hz, 1H), 3.37 (dd, J=6, 14 Hz, 1H), 3.00 (s, 3H), 2.90 (dd, J=5, 14 Hz, 1H), 2.48 (m, 1H), 1.62 (m, 1H), 1.21–1.44 (m, 2H), 0.91 (d, J=7 Hz, 3H), 0.90 (d, J=7 Hz, 3H), 0.87 (s, 9H), 0.03 (s, 6H); mass spectrum (PCI), m/e 307 (MH⁺, 100).

17B. Formula 20 Where X Is NH, R¹ Is n-butyl and R² Is 2-Methylpropyl

By following the procedures described in Example 17A and substituting MeS-(CH₂-DL-Leu-CH₂)-OTBS with n-BuS-(CH₂-DL-Leu-CH₂)-OTBS, 227 mg (45% yield, based on recovered starting material) of n-BuS (NH)₂-(CH₂-DL-Leu-CH₂)-OTBS was obtained as a gum. Characteristic analytical data are as follows: ¹H NMR (300 MHz, CDCl₃) δ3.78 (dd, J=4, 10 Hz, 1H), 3.58 (dd, J=5, 10 Hz, 1H), 3.31 (dd, J=6, 14 Hz, 1H), 3.03 (m, 2H), 2.84 (dd, J=5, 14 Hz, 1H), 2.54 (m, 1H), 1.6–1.8 (m, 4H), 1.26–1.54 (m, 3H), 0.97 (t, J=7 Hz, 3H), 0.94 (d, J=6 Hz, 3H), 0.92 (d, J=6 Hz, 3H), 0.89 (s, 9H), 0.06 (s, 6H); mass spectrum (PCI), m/e 349 (MH⁺, 100), 332 (21), 291 (53), 235 (29), 171 (20), 121 (16).

17C. Formula 20 Where X Is NH, R¹ Is n-butyl and R² Is 4-Methoxyphenylmethyl

By following the procedures described in Example 17A and substituting MeS-(CH₂-DL-Leu-CH₂)-OTBS with n-BuS-(CH₂-DL-TyrOCH₃-CH₂)-OTBS, 250 mg (53% yield, based on recovered starting material) of the sulfodiimine n-BuS(NH)₂-(CH₂-DL-TyrOMe-CH₂)-OTBS was obtained as a gum. Characteristic analytical data are as follow: ¹H NMR (300 MHz, CDCl₃) δ7.12 (d, J=9 Hz, 2H), 6.84 (d, J=9 Hz, 2H), 3.79 (s, 3H), 3.72 (dd, J=5, 10 Hz, 1H), 3.60 (dd, J=5, 10 Hz, 1H), 3.26 (dd, J=7, 14 Hz, 1H), 3.04 (dd, J=5, 14 Hz, 1H), 2.91 (t, J=8 Hz, 2H), 2.78 (dd, J=8, 14 Hz, 1H), 2.71 (dd, J=7, 14 Hz, 1H), 2.42 (m, 1H), 1.71 (m, 1H), 1.62 (m, 1H), 1.38 (m, 2H), 0.92 (t, J=7 Hz, 3H), 0.90 (s, 9H), 0.03 (s, 6H).

17D. Formula 20 Varying $R^1$, $R^2$ and $R^3$

By following the procedures described in Example 17A and substituting MeS-(CH$_2$-DL-Leu-CH$_2$)-OTBS with other compounds of Formula 19 (where $R^1$, $R^2$ and $R^3$ are as indicated in the table below) there are obtained the corresponding substituted compounds of Formula 20.

Formula 20

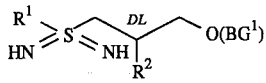

| $R^1$ | $R^2$ | Name |
|---|---|---|
| ethyl | H | EtS(NH)$_2$—(CH$_2$-DL-Gly—CH$_2$)—OTBS |
| benzyl | methyl | BnS(NH)$_2$—(CH$_2$-DL-Ala—CH$_2$)—OTBS |
| phenethyl | 2-propyl | PhetS(NH)$_2$—(CH$_2$-DL-Val—CH$_2$)—OTBS |
| blocked 4-hydroxyphenethyl | 2-butyl | (4-hydroxyphenethyl)-S(NH)$_2$—(CH$_2$-DL-Ile—CH$_2$)—OTBS |
| blocked 2-(4-imidazolyl)ethyl | benzyl | 2(4-imidazolyl)ethyl-S(NH)$_2$—(CH$_2$-DL-Phe—CH$_2$)—OTBS |
| blocked 3-carboxypropyl | blocked 4-hydroxyphenylmethyl | (3-carboxypropyl)S(NH)$_2$—(CH$_2$-DL-Tyr—CH$_2$)—OTBS |
| ethyl | 4-methoxyphenylmethyl | EtS(NH)$_2$—(CH$_2$-DL-TyrOCH$_3$—CH$_2$)—OTBS |
| benzyl | blocked 3-indolylmethyl | BnS(NH)$_2$—(CH$_2$-DL-Trp—CH$_2$)—OTBS |
| phenethyl | phenylethyl | PhetS(NH)$_2$—(CH$_2$-DL-Phet—CH$_2$)—OTBS |
| blocked 4-hydroxyphenethyl | blocked 4-aminobutyl | (4-hydroxyphenethyl)-S(NH)$_2$—(CH$_2$-DL-Lys—CH$_2$)—OTBS |
| blocked 2-(4-imidazolyl)ethyl | blocked 3-guanylpropyl | 2-(4-imidazolyl)ethyl-S(NH)$_2$—(CH$_2$-DL-Arg—CH$_2$)—OTBS |
| blocked 3-carboxypropyl | blocked 4-imidazoylmethyl | 3-carboxypropylS(NH)$_2$—(CH$_2$-DL-His—CH$_2$)—OTBS |
| ethyl | H | EtS(NH)$_2$—(CH$_2$-DL-Gly—CH$_2$)—OTBS |
| benzyl | methyl | BnS(NH)$_2$—(CH$_2$-DL-Ala—CH$_2$)—OTBS |
| phenethyl | 2-propyl | PhetS(NH)$_2$—(CH$_2$-DL-Val—CH$_2$)—OTBS |
| blocked 4-hydroxyphenethyl | 2-butyl | 4-hydroxyphenethylS(NH)$_2$—(CH$_2$-DL-Ile—CH$_2$)—OTBS |
| blocked 2-(4-imidazolyl)ethyl | benzyl | 2-(4-imidazolyl)ethyl-S(NH)$_2$—(CH$_2$-DL-Phe—CH$_2$)—OTBS |
| blocked 3-carboxypropyl | blocked 4-hydroxyphenylmethyl | 3-carboxypropylS(NH)$_2$—(CH$_2$-DL-Tyr—CH$_2$)—OTBS |
| ethyl | blocked 3-indolylmethyl | EtS(NH)$_2$—(CH$_2$-DL-Trp—CH$_2$)-OTBS |
| benzyl | phenylethyl | BnS(NH)$_2$—(CH$_2$-DL-Phet—CH$_2$)—OTBS |
| phenethyl | blocked 4-aminobutyl | PhetS(NH)$_2$—(CH$_2$-DL-Lys—CH$_2$)—OTBS |
| blocked 4-hydroxyphenethyl | blocked 3-guanylpropyl | (4-hydroxyphenethyl)-S(NH)$_2$—(CH$_2$-DL-Arg—CH$_2$)-OTBS |
| blocked 2-(4-imidazolyl)ethyl | blocked 4-imidazoylmethyl | 2-(4-imidazolyl)ethyl-S(NH)$_2$—(CH$_2$-DL-His—CH$_2$)—OTBS |
| blocked 3-carboxypropyl | H | 3-carboxypropylS(NH)$_2$—(CH$_2$-DL-Gly—CH$_2$)—OTBS |
| ethyl | methyl | EtS(NH)$_2$—(CH$_2$-DL-Ala—CH$_2$)—OTBS |
| benzyl | 2-propyl | BnS(NH)$_2$—(CH$_2$-DL-Val—CH$_2$)—OTBS |
| phenethyl | 2-butyl | PhetS(NH)$_2$—(CH$_2$-DL-Ile—CH$_2$)—OTBS |
| blocked 4-hydroxyphenethyl | benzyl | 4-hydroxyphenethylS(NH)$_2$—(CH$_2$-DL-Phe—CH$_2$)—OTBS |
| blocked 2-(4- | blocked 4- | 2-(4-imidazolyl)- |

-continued

Formula 20

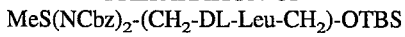

| $R^1$ | $R^2$ | Name |
|---|---|---|
| imidazolyl)ethyl | hydroxyphenylmethyl | ethylS(NH)$_2$—(CH$_2$-DL-Tyr—CH$_2$)—OTBS |
| blocked 3-carboxypropyl | blocked 3-indolylmethyl | 3-carboxypropylS(NH)$_2$—(CH$_2$-DL-Trp—CH$_2$)—OTBS |
| ethyl | phenylethyl | EtS(NH)$_2$—(CH$_2$-DL-Phet—CH$_2$)—OTBS |
| benzyl | blocked 4-aminobutyl | BnS(NH)$_2$—(CH$_2$-DL-Lys—CH$_2$)—OTBS |
| phenethyl | blocked 3-guanylpropyl | PhetS(NH)$_2$—(CH$_2$-DL-Arg—CH$_2$)—OTBS |
| blocked 4-hydroxyphenethyl | blocked 4-imidazoylmethyl | 4-hydroxyphenethylS(NH)$_2$—(CH$_2$-DL-His—CH$_2$)—OTBS |
| blocked 2-(4-imidazolyl)ethyl | H | 2-(4-imidazolyl)-ethylS(NH)$_2$—(CH$_2$-DL-Gly—CH$_2$)—OTBS |
| blocked 3-carboxypropyl | methyl | 3-carboxypropylS(NH)$_2$—(CH$_2$-DL-Ala—CH$_2$)—OTBS |
| ethyl | 2-propyl | EtS(NH)$_2$—(CH$_2$-DL-Val—CH$_2$)—OTBS |
| benzyl | 2-butyl | BnS(NH)$_2$—(CH$_2$-DL-Ile—CH$_2$)—OTBS |
| phenethyl | benzyl | PhetS(NH)$_2$—(CH$_2$-DL-Phe—CH$_2$)—OTBS |
| blocked 4-hydroxyphenethyl | blocked 4-hydroxyphenylmethyl | 4-hydroxyphenethylS(NH)$_2$—(CH$_2$-DL-Tyr—CH$_2$)—OTBS |
| blocked 2-(4-imidazolyl)ethyl | blocked 3-indolylmethyl | 2-(4-imidazolyl)-ethylS(NH)$_2$—(CH$_2$-DL-Trp—CH$_2$)—OTBS |
| blocked 3-carboxypropyl | phenylethyl | 3-carboxypropylS(NH)$_2$—(CH$_2$-DL-Phet—CH$_2$)—OTBS |

EXAMPLE 18

PREPARATION OF MeS(NCbz)$_2$-(CH$_2$-DL-Leu-CH$_2$)-OTBS

18A. Formula 21 Where $R^1$ Is Methyl and $R^2$ Is 2-Methylpropyl

To a solution of 566 mg of the sulfodiimine MeS(NH)$_2$-(CH$_2$-DL-Leu-CH$_2$)-OTBS in 5 mL of CH$_2$Cl$_2$ was added 0.76 mL of pyridine and 1 mL of benzyl chloroformate, and the mixture was stirred for 6 h at room temperature. Saturated aqueous NaHCO$_3$ was added and the mixture was extracted with CH$_2$Cl$_2$. The organic layer was evaporated under vacuum and the residue was subjected to flash chromatography (15% EtOAc in hexane) to give 800 mg (75% yield) of MeS(NCbz)$_2$-(CH$_2$-DL-Leu-CH$_2$)-OTBS as a gum. Characteristic analytical data are as follows: $^1$H NMR (300 MHz, CDCl$_3$) δ7.27–7.39 (m, 10H), 5.06–5.16 (m, 4H), 3.82 (dd, J=6, 14 Hz, 1H), 3.68–3.76 (m, 2H), 3.52 (s, 3H), 3.48 (dd, J=5, 11 Hz, 1H), 2.24 (m, 1H), 1.56 (m, 1H), 1.2–1.4 (m, 2H), 0.88 (s, 9H), 0.85 (d, J=7 Hz, 3H), 0.84 (d, J=7 Hz, 3H), 0.03 (s, 6H).

18B. Formula 21 Where $R^1$ Is n-butyl and $R^2$ Is 2-Methylpropyl

By following the procedures described in Example 18A and substituting MeS (NH)$_2$-(CH$_2$-DL-Leu-CH$_2$)-OTBS with n-BuS(NH)$_2$-(CH$_2$-DL-Leu-CH$_2$)-OTBS, 550 mg (67% yield) of n-BuS(NCbz)$_2$-(CH$_2$-DL-Leu-CH$_2$)-OTBS was obtained as a gum. Characteristic analytical data are as follows: $^1$H NMR (300 MHz, CDCl$_3$) δ7.27–7.4 (m, 10H), 5.13 (d, J=13 Hz, 1H), 5.11 (s, 2H), 5.07 (d, J=13 Hz, 1H), 3.59–3.94 (m, 5H), 3.48 (dd, J=5, 11 Hz, 1H), 2.19 (m, 1H), 1.70 (m, 2H), 1.57 (m, 1H), 1.38 (m, 3H), 1.23 (m, 1H), 0.89 (t, J=7 Hz, 3H), 0.88 (s, 9H), 0.84 (s, 3H), 0.82 (s, 3H), 0.03 (s, 6H).

18C. Formula 21 Where $R^1$ Is n-butyl and $R^2$ Is 4-Methoxyphenylmethyl

By following the procedures described in Example 18A and substituting MeS(NH)$_2$-(CH$_2$-DL-Leu-CH$_2$)-OTBS with n-BuS(NH)$_2$-(CH$_2$-DL-TyrOMe-CH$_2$)-OTBS, 685 mg (66% yield) of n-BuS (NCbz)$_2$-(CH$_2$-DL-TyrOMe-CH$_2$)-OTBS was obtained as a gum. Further elution of the column gave 82 mg of starting material and 85 mg of the mono-Cbz sulfodiimine. Characteristic analytical data of n-BuS(NCbz)$_2$-(CH$_2$-DL-TyrOMe-CH$_2$)-OTBS are as follows: $^1$H NMR (500 MHz, CDCl$_3$) δ7.27–7.40 (m, 10H), 7.02 (d, J=9 Hz, 2H), 6.79 (d, J=9 Hz, 2H), 5.12 (d, J=8 Hz, 1 H), 5.09 (s, 2H), 5.07 (d, J=8 Hz, 1H), 3.89 (dd, J=6, 15 Hz, 1H), 3.78 (s, 3H), 3.54–3.68 (m, 4H), 3.48 (dd, J=4, 10 Hz, 1H), 2.68 (d, J=7 Hz, 2H), 2.34 (br m, 1H), 1.6 (m, 1H), 1.45 (m, 1H), 1.3 (m, 2H), 0.88 (s, 9H), 0.84 (t, J=7 Hz, 3H), 0.03 (s, 6H).

18C. Formula 21 Varying $R^1$, $R^2$ and $R^3$

By following the procedures described in Example 18A and substituting MeS(NH$_2$)-(CH$_2$-DL-Leu-CH$_2$)-OTBS with other compounds of Formula 20 (where $R^1$, $R^2$ and $R^3$ are as indicated in the table below) there are obtained the corresponding substituted compounds of Formula 21.

Formula 21

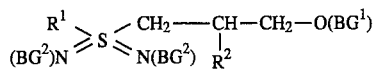

| R$^1$ | R$^2$ | Name |
|---|---|---|
| ethyl | H | EtS(NCbz)$_2$ — (CH$_2$-DL-Gly — CH$_2$) — OTBS |
| benzyl | methyl | BnS(NCbz)$_2$ — (CH$_2$-DL-Ala — CH$_2$) — OTBS |
| phenethyl | 2-propyl | PhetS(NCbz)$_2$ — (CH$_2$-DL-Val — CH$_2$) — OTBS |
| blocked 4-hydroxyphenethyl | 2-butyl | (4-hydroxyphenethyl)-S(NCbz)$_2$ — (CH$_2$ — DL-Ile — CH$_2$) — OTBS |
| blocked 2-(4-imidazolyl)ethyl | benzyl | 2(4-imidazolyl)ethyl-S(NCbz)$_2$ — (CH$_2$-DL-Phe — CH$_2$) — OTBS |
| blocked 3-carboxypropyl | blocked 4 hydroxyphenylmethyl | (3-carboxypropyl) S(NCbz)$_2$ — (CH$_2$-DL-Tyr — CH$_2$) — OTBS |
| ethyl | 4-methoxyphenylmethyl | EtS(NCbz)$_2$ — (CH$_2$-DL-TyrOCH$_3$ — CH$_2$) — OTBS |
| benzyl | blocked 3-indolylmethyl | BnS(NCbz)$_2$ — (CH$_2$-DL-Trp — CH$_2$) — OTBS |
| phenethyl | phenylethyl | PhetS(NCbz)$_2$ — (CH$_2$-DL-Phet — CH$_2$) — OTBS |
| blocked 4-hydroxyphenethyl | blocked 4-aminobutyl | (4-hydroxyphenethyl)-S(NCbz)$_2$ — (CH$_2$-DL-Lys — CH$_2$) — OTBS |
| blocked 2-(4-imidazolyl)ethyl | blocked 3-guanylpropyl | 2-(4-imidazolyl)ethyl-S(NCbz)$_2$ — (CH$_2$-DL-Arg — CH$_2$) — OTBS |
| blocked 3-carboxypropyl | blocked 4-imidazoylmethyl | 3-carboxypropylS(NCbz)$_2$ — (CH$_2$-DL-His — CH$_2$) — OTBS |
| ethyl | H | EtS(NCbz)$_2$ — (CH$_2$-DL-Gly — CH$_2$) — OTBS |
| benzyl | methyl | BnS(NCbz)$_2$ — (CH$_2$-DL-Ala — CH$_2$) — OTBS |
| phenethyl | 2-propyl | PhetS(NCbz)$_2$ — (CH$_2$-DL-Val — CH$_2$) — OTBS |
| blocked 4-hydroxyphenethyl | 2-butyl | 4-hydroxyphenethyl-S(NCbz)$_2$ — (CH$_2$-DL-Ile — CH$_2$) — OTBS |
| blocked 2-(4-imidazolyl)ethyl | benzyl | 2-(4-imidazolyl)ethyl-S(NCbz)$_2$ — (CH$_2$-DL-Phe — CH$_2$) — OTBS |
| blocked 3-carboxypropyl | blocked 4-hydroxyphenylmethyl | 3-carboxypropylS(NCbz)$_2$ — (CH$_2$-DL-Tyr — CH$_2$) — OTBS |
| ethyl | blocked 3-indolylmethyl | EtS(NCbz)$_2$ — (CH$_2$-DL-Trp-CH$_2$) — OTBS |
| benzyl | phenylethyl | BnS(NCbz)$_2$ — (CH$_2$-DL-Phet — CH$_2$) — OTBS |
| phenethyl | blocked 4-aminobutyl | PhetS(NCbz)$_2$ — (CH$_2$-DL-Lys — CH$_2$) — OTBS |
| blocked 4-hydroxyphenethyl | blocked 3-guanylpropyl | (4-hydroxyphenethyl)-S(NCbz)$_2$ — (CH$_2$-DL-Arg — CH$_2$) — OTBS |
| blocked 2-(4-imidazolyl)ethyl | blocked 4-imidazoylmethyl | 2-(4-imidazolyl)ethyl-S(NCbz)$_2$ — (CH$_2$-DL-His — CH$_2$) — OTBS |
| blocked 3-carboxypropyl | H | 3-carboxypropylS(NCbz)$_2$ — (CH$_2$-DL-Gly — CH$_2$) — OTBS |
| ethyl | methyl | EtS(NCbz)$_2$ — (CH$_2$-DL-Ala — CH$_2$) — OTBS |
| benzyl | 2-propyl | BnS(NCbz)$_2$ — (CH$_2$-DL-Val — CH$_2$) — OTBS |
| phenethyl | 2-butyl | PhetS(NCbz)$_2$ — (CH$_2$-DL-Ile — CH$_2$) — OTBS |
| blocked 4-hydroxyphenethyl | benzyl | 4-hydroxyphenethyl-S(NCbz)$_2$ — (CH$_2$-DL-Phe — CH$_2$) — OTBS |
| blocked 2-(4-imidazolyl)ethyl | blocked 4-hydroxyphenylmethyl | 2-(4-imidazolyl)-ethylS(NCbz)$_2$ — (CH$_2$-DL-Tyr — CH$_2$) — OTBS |
| blocked 3-carboxypropyl | blocked 3-indolylmethyl | 3-carboxypropylS(NCbz)$_2$ — (CH$_2$-DL-Trp — CH$_2$) — OTBS |

Formula 21

$$\underset{(BG^2)N}{R^1} \!\!\gtrless\! S \!\!\lessgtr\! \underset{N(BG^2)}{CH_2} \!-\!\!\underset{R^2}{\overset{DL}{CH}}\!-\!CH_2\!-\!O(BG^1)$$

| R¹ | R² | Name |
|---|---|---|
| ethyl | phenylethyl | EtS(NCbz)₂ — (CH₂-DL-Phet — CH₂) — OTBS |
| benzyl | blocked 4-aminobutyl | BnS(NCbz)₂ — (CH₂-DL-Lys — CH₂) — OTBS |
| phenethyl | blocked 3-guanylpropyl | PhetS(NCbz)₂ — (CH₂-DL-Arg- — CH₂) — OTBS |
| blocked 4-hydroxy-phenethyl | blocked 4-imidazoylmethyl | 4-hydroxyphen-ethylS(NCbz)₂ — (CH₂-DL-His — CH₂) — OTBS |
| blocked 2-(4-imidazolyl)ethyl | H | 2-(4-imidazolyl)-ethylS(NCbz)₂ — (CH₂-DL-Gly — CH₂) — OTBS |
| blocked 3-carboxy-propyl | methyl | 3-carboxypropylS(NCbz)₂ — (CH₂-DL-Ala — CH₂) — OTBS |
| ethyl | 2-propyl | EtS(NCbz)₂ — (CH₂-DL-Val — CH₂) — OTBS |
| benzyl | 2-butyl | BnS(NCbz)₂ — (CH₂DL-Ile — CH₂) — OTBS |
| phenethyl | benzyl | PhetS(NCbz)₂ — (CH₂-DL-Phe — CH₂) — OTBS |
| blocked 4-hydroxy-phenethyl | blocked 4-hydroxyphenylmethyl | 4-hydroxyphen-ethylS(NCbz)₂ — (CH₂-DL-Tyr — CH₂) — OTBS |
| blocked 2-(4-imidazolyl)ethyl | blocked 3-indolylmethyl | 2-(4-imidazolyl)-ethylS(NCbz)₂ — (CH₂-DL-Trp-CH₂) — OTBS |
| blocked 3-carboxy-propyl | phenylethyl | 3-carboxypropylS(NCbz)₂ — (CH₂-DL-Phet — CH₂) — OTBS |

EXAMPLE 19

PREPARATION OF MeS(NCbz)₂-(CH₂-DL-Leu-CH₂)-OH

19A. Formula 22 Where R¹ Is Methyl and R² Is 2-Methylpropyl

To a solution of 762 mg of MeS(NCbz)₂-(CH₂-DL-Leu-CH₂)-OTBS in 5 mL of THF was added 838 mg of tetrabutylammonium fluoride hydrate, and the solution was stirred at room temperature for 2.5 h. The mixture was diluted with EtOAc and was washed with water. The organic layer was dried over Na₂SO₄ and evaporated under vacuum. The residue was purified by flash chromatography (60% EtOAc in hexane) to give 444 mg (72% yield) of MeS (NCbz)₂-(CH₂-DL-Leu-CH₂)-OH as a gum. Characteristic analytical data are as follows: ¹H NMR (300 MHz, CDCl₃) δ7.24–7.38 (m10), 5.10 (m, 4H), 3.85 (dd, J=8, 14 Hz, 1H), 3.76 (m, 1H), 3.65 (dd, J=4, 14 Hz, 1H), 3.55 (s, 3H), 3.41 (dd, J=6, 11 Hz, 1H), 2.22 (m, 1H), 1.56 (m, 1H), 1.16–1.35 (m2), 0.84 (s, 3H), 0.82 (s, 3H).

19B. Formula 22 Where R¹ Is n-butyl and R² Is 2-Methylpropyl

By following the procedures described in Example 19A and substituting MeS(NCbz)₂-(CH₂-DL-Leu-CH₂)-OTBS with n-BuS (NCbz)₂-(CH₂-DL-Leu-CH₂)-OTBS, 287 mg (65% yield) of n-BuS (NCbz)₂-(CH₂-DL-Leu-CH₂)-OH was obtained as a gum. Characteristic analytical data are as follows: ¹H NMR (300 MHz, CDCl₃) δ7.27–7.40 (m, 10H), 5.09 (s, 4H), 3.82–3.94 (m, 3H), 3.78 (dd, J=4, 11 Hz, 1H), 3.57 (dd, J=4, 14 Hz, 1H), 3.42 (dd, J=5, 11 Hz, 1H), 2.22 (m, 1H), 1.52–1.79 (m, 4H), 1.20–1.43 (m, 3H), 0.91 (t, J=8 Hz, 3H), 0.85 (d, J=7 Hz, 3H), 0.84 (d, J=7 Hz, 3H).

19C. Formula 19 Where R¹ Is n-butyl and R² Is 4-Methoxyphenylmethyl

By following the procedures described in Example 19A and substituting MeS(NCbz)₂-(CH₂-DL-Leu-CH₂)-OTBS with n-BuS(NCbz)₂-(CH₂-DL-TYrOCH₃-CH₂)-OTBS, 400 mg (71% yield) of n-BuS(NCbz)₂-(CH₂-DL-TyrOMe-CH₂)-OH as a gum was obtained. Characteristic analytical data are as follows: ¹H NMR (300 MHz, CDCl₃) δ7.27–7.40 (m, 10H), 7.03 (d, J=9 Hz, 2H), 6.82 (d, J=9 Hz, 2H), 5.10 (m, 4H), 3.99 (dd, J=8, 14 Hz, 1H), 3.78 (s, 3H), 3.68–3.74 (m, 2H), 3.40–3.58 (m, 3H), 2.72 (dd, J=7, 14 Hz, 1H), 2.62 (dd, J=6, 14 Hz, 1H), 2.33 (br m, 1H), 1.78 (br m, 1H), 1.55 (br m, 1H), 1.26 (br m, 2H), 0.82 (t, J=7 Hz, 3H).

19C. Formula 22 Varying R¹, R² and R³

By following the procedures described in Example 19A and substituting MeS(NCbz)₂-(CH₂-DL-Leu-CH₂)-OTBS with other compounds of Formula 21 (where R¹, R² and R³ are as indicated in the table below) there are obtained the corresponding substituted compounds of Formula 22.

Formula 22

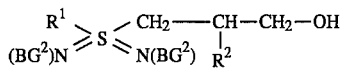

$$R^1\!\!\geqslant\!\!S\!\!\leqslant\!\!\genfrac{}{}{0pt}{}{CH_2}{N(BG^2)}\!\!-\!\!\overset{DL}{\underset{R^2}{CH}}\!\!-\!\!CH_2\!\!-\!\!OH$$
$(BG^2)N$

| R$^1$ | R$^2$ | Name |
|---|---|---|
| ethyl | H | EtS(NCbz)$_2$—(CH$_2$-DL-Gly—CH$_2$)—OH |
| benzyl | methyl | BnS(NCbz)$_2$—(CH$_2$-DL-Ala—CH$_2$)—OH |
| phenethyl | 2-propyl | PhetS(NCbz)$_2$—(CH$_2$-DL-Val—CH$_2$)—OH |
| blocked 4-hydroxyphenethyl | 2-butyl | (4-hydroxyphenethyl)-S(NCbz)$_2$—(CH$_2$-DL-Ile—CH$_2$)—OH |
| blocked 2-(4-imidazolyl)ethyl | benzyl | 2(4-imidazolyl)ethyl-S(NCbz)$_2$—(CH$_2$-DL-Phe—CH$_2$)—OH |
| blocked 3-carboxypropyl | blocked 4-hydroxyphenylmethyl | (3-carboxypropyl)S(NCbz)$_2$—(CH$_2$-DL-Tyr—CH$_2$)—OH |
| ethyl | 4-methoxyphenylmethyl | EtS(NCbz)$_2$—(CH$_2$-DL-TyrOCH$_3$—CH$_2$)—OH |
| benzyl | blocked 3-indolylmethyl | BnS(NCbz)$_2$—(CH$_2$-DL-Trp—CH$_2$)—OH |
| phenethyl | phenylethyl | PhetS(NCbz)$_2$—(CH$_2$-DL-Phet—CH$_2$)—OH |
| blocked 4-hydroxyphenethyl | blocked 4-aminobutyl | (4-hydroxyphenethyl)-S(NCbz)$_2$—(CH$_2$-DL-Lys—CH$_2$)—OH |
| blocked 2-(4-imidazolyl)ethyl | blocked 3-guanylpropyl | 2-(4-imidazolyl)ethyl-S(NCbz)$_2$—(CH$_2$-DL-Arg—CH$_2$)—OH |
| blocked 3-carboxypropyl | blocked 4-imidazoylmethyl | 3-carboxypropylS(NCbz)$_2$—(CH$_2$-DL-His—CH$_2$)—OH |
| ethyl | H | EtS(NCbz)$_2$—(CH$_2$-DL-Gly—CH$_2$)—OH |
| benzyl | methyl | BnS(NCbz)$_2$—(CH$_2$-DL-Ala—CH$_2$)—OH |
| phenethyl | 2-propyl | PhetS(NCbz)$_2$—(CH$_2$-DL-Val—CH$_2$)—OH |
| blocked 4-hydroxyphenethyl | 2-butyl | 4-hydroxyphenethyl-S(NCbz)$_2$—(CH$_2$-DL-Ile—CH$_2$)—OH |
| blocked 2-(4-imidazolyl)ethyl | benzyl | 2-(4-imidazolyl)ethyl-S(NCbz)$_2$—(CH$_2$-DL-Phe—CH$_2$)—OH |
| blocked 3-carboxypropyl | blocked 4-hydroxyphenylmethyl | 3-carboxypropylS(NCbz)$_2$—(CH$_2$-DL-Tyr—CH$_2$)—OH |
| ethyl | blocked 3-indolylmethyl | EtS(NCbz)$_2$—(CH$_2$-DL-Trp—CH$_2$)—OH |
| benzyl | phenylethyl | BnS(NCbz)$_2$—(CH$_2$-DL-Phet—CH$_2$)—OH |
| phenethyl | blocked 4-aminobutyl | PhetS(NCbz)$_2$—(CH$_2$-DL-Lys—CH$_2$)—OH |
| blocked 4-hydroxyphenethyl | blocked 3-guanylpropyl | (4-hydroxyphenethyl)—S(NCbz)$_2$—(CH$_2$-DL-Arg—CH$_2$)—OH |
| blocked 2-(4-imidazolyl)ethyl | blocked 4-imidazoylmethyl | 2-(4-imidazolyl)ethyl-S(NCbz)$_2$—(CH$_2$-DL-His—CH$_2$)—OH |
| blocked 3-carboxypropyl | H | 3-carboxypropylS(NCbz)$_2$—(CH$_2$-DL-Gly—CH$_2$)—OH |
| ethyl | methyl | EtS(NCbz)$_2$—(CH$_2$-DL-Ala—CH$_2$)—OH |
| benzyl | 2-propyl | BnS(NCbz)$_2$—(CH$_2$-DL-Val—CH$_2$)—OH |
| phenethyl | 2-butyl | PhetS(NCbz)$_2$—(CH$_2$-DL-Ile—CH$_2$)—OH |
| blocked 4-hydroxyphenethyl | benzyl | 4-hydroxyphenethyl-S(NCbz)$_2$—(CH$_2$-DL-Phe—CH$_2$)—OH |
| blocked 2-(4-imidazolyl)ethyl | blocked 4-hydroxyphenylmethyl | 2-(4-imidazolyl)-ethylS(NCbz)$_2$—(CH$_2$-DL-Tyr—CH$_2$)—OH |
| blocked 3-carboxypropyl | blocked 3-indolylmethyl | 3-carboxypropylS(NCbz)$_2$—(CH$_2$-DL-Trp—CH$_2$)—OH |

-continued

Formula 22

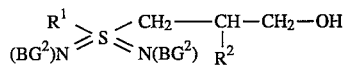

| R¹ | R² | Name |
|---|---|---|
| ethyl | phenylethyl | EtS(NCbz)₂—(CH₂-DL-Phet—CH₂)—OH |
| benzyl | blocked 4-aminobutyl | BnS(NCbz)₂—(CH₂-DL-Lys—CH₂)—OH |
| phenethyl | blocked 3-guanylpropyl | PhetS(NCbz)₂—(CH₂-DL-Arg—CH₂)—OH |
| blocked 4-hydroxyphenethyl | blocked 4-imidazoylmethyl | 4-hydroxyphenethylS(NCbz)₂—(CH₂-DL-His—CH₂)—OH |
| blocked 2-(4-imidazolyl)ethyl | H | 2-(4-imidazolyl)—ethylS(NCbz)₂—(CH₂-DL-Gly—CH₂)—OH |
| blocked 3-carboxypropyl | methyl | 3-carboxypropylS(NCbz)₂—(CH₂-DL-Ala—CH₂)—OH |
| ethyl | 2-propyl | EtS(NCbz)₂—(CH₂-DL-Val—CH₂)—OH |
| benzyl | 2-butyl | BnS(NCbz)₂—(CH₂-DL-Ile—CH₂)—OH |
| phenethyl | benzyl | PhetS(NCbz)₂—(CH₂-DL-Phe—CH₂)—OH |
| blocked 4-hydroxyphenethyl | blocked 4-hydroxyphenylmethyl | 4-hydroxyphenethylS(NCbz)₂—(CH₂-DL-Tyr—CH₂)—OH |
| blocked 2-(4-imidazolyl)ethyl | blocked 3-indolylmethyl | 2-(4-imidazolyl)-ethylS(NCbz)₂—(CH₂-DL-Trp—CH₂)—OH |
| blocked 3-carboxypropyl | phenylethyl | 3-carboxypropylS(NCbz)₂—(CH₂-DL-Phet—CH₂)—OH |

EXAMPLE 20

PREPARATION OF MeS(NCbz)₂-(CH₂-DL-Leu)-OH

20A. Formula 23 Where R¹ Is Methyl and R² Is 2-Methylpropyl

To a solution of 390 mg of MeS(NCbz)₂-(CH₂-DL-Leu-CH₂)-OH in 5 mL of acetone was added 0.5 mL of Jones reagent dropwise at 0° C., and stirring was continued for 3 h. The reaction mixture was poured into water and was extracted with CH₂Cl₂. The organic layer was dried over Na₂SO₄ and evaporated under vacuum, and the residue was purified by flash chromatography to give 290 mg (72% yield) of MeS(NCbz)₂-(CH₂-DL-Leu)-OH as a viscous oil: ¹H NMR (300 MHz, CDCl₃) δ7.24–7.40 (m, 10H), 5.04–5.15 (m, 4H), 4.09 (dd, J=9, 14 Hz, 1H), 3.88 (d, J=14 Hz, 1H), 3.42 (s, 3H), 3.05–3.16 (m, 1H), 1.54–1.68 (m, 2H), 1.32–1.45 (m, 1H), 0.88 (d, J=6 Hz, 3H), 0.86 (d, J=6 Hz, 3H).

20B. Formula 23 Where R¹ Is n-Butyl and R² Is 2-Methylpropyl

By following the procedures described in Example 20A and substituting MeS(NCbz)₂-(CH₂-DL-Leu-CH₂)-OH with n-BuS(NCbz)₂-(CH₂-DL-TyrOMe-CH₂)-OH, 185 mg (72% yield) of n-BuS(NCbz)₂-(CH₂-DL-Leu)-OH was obtained as a viscous oil. Characteristic analytical data are as follows: ¹H NMR (300 MHz, CDCl₃) δ7.27–7.40 (m, 10H), 5.12 (d, J=12 Hz, 1H), 5.10 (s, 2H), 5.06 (d, J=12 Hz, 1H), 4.1 (m, 1H), 3.8 (m, 2H), 3.6 (m, 1H), 3.16 (m, 1H), 1.55–1.76 (m, 4 H), 1.37 (m, 3H), 0.88 (t, J=7 Hz, 3H), 0.87 (d, J=6 Hz, 3H), 0.85 (d, J=6 Hz, 3H).

20C. Formula 23 Where R¹ Is n-Butyl and R² Is 4-Methoxyphenylmethyl

By following the procedures described in Example 20A and substituting MeS(NCbz)₂-(CH₂-DL-Leu-CH₂)-OH with n-BuS(NCbz)₂-(CH₂-DL-TyrOMe-CH₂)-OH, 238 mg (58% yield) of n-BuS (NCbz)₂-(CH₂-DL-TyrOMe)-OH was obtained as a viscous oil. Characteristic analytical data are as follows: ¹H NMR (300 MHz, CDCl₃) δ7.24–7.39 (m, 10H), 7.02 (d, J=9 Hz, 2H), 6.78 (d, J=9 Hz, 2H), 5.03 (m, 4.20 (m, 1H), 3.72 (s, 3H), 3.54 (m, 3H), 3.22 (m, 1H), 3.05 (m, 1H), 2.75 (m, 1H), 1.5 (m, 1H), 1.21 (m, 3H), 0.75 (t, J=7 Hz, 3H).

20C. Formula 23 Varying R¹, R² and R³

By following the procedures described in Example 20A and substituting MeS(NCbz)₂-(CH₂-DL-Leu-CH₂)-OH with other compounds of Formula 22 (where R¹, R² and R³ are as indicated in the table below) there are obtained the corresponding substituted compounds of Formula 23.

Formula 23

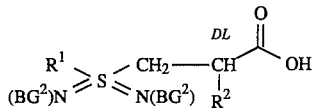

| R¹ | R² | Name |
|---|---|---|
| ethyl | H | EtS (NCbz)$_2$-(CH$_2$-DL-Gly)-OH |
| benzyl | methyl | BnS (NCbz)$_2$-(CH$_2$-DL-Ala)-OH |
| phenethyl | 2-propyl | PhetS (NCbz)$_2$-(CH$_2$-DL-Val)-OH |
| blocked 4-hydroxyphenethyl | 2-butyl | (4-hydroxyphenethyl)-S (NCbz)$_2$-(CH$_2$-DL-Ile)-OH |
| blocked 2-(4-imidazolyl)ethyl | benzyl | 2(4-imidazolyl)ethyl-S (NCbz)$_2$-(CH$_2$-DL-Phe)-OH |
| blocked 3-carboxypropyl | blocked 4-hydroxyphenylmethyl | (3-carboxypropyl)S(NCbz)$_2$-(CH$_2$-DL-Tyr)-OH |
| ethyl | 4-methoxyphenylmethyl | EtS (NCbz)$_2$-(CH$_2$-DL-TyrOCH$_3$)-OH |
| benzyl | blocked 3-indolylmethyl | BnS (NCbz)$_2$-(CH$_2$-DL-Trp)-OH |
| phenethyl | phenylethyl | PhetS (NCbz)$_2$-(CH$_2$-DL-Phet)-OH |
| blocked 4-hydroxyphenethyl | blocked 4-aminobutyl | (4-hydroxyphenethyl)-S (NCbz)$_2$-(CH$_2$-DL-Lys)-OH |
| blocked 2-(4-imidazolyl)ethyl | blocked 3-guanylpropyl | 2-(4-imidazolyl)ethyl-S(NCbz)$_2$-(CH$_2$-DL-Arg)-OH |
| blocked 3-carboxypropyl | blocked 4-imidazaylmethyl | 3-carboxypropylS(NCbz)$_2$-(CH$_2$-DL-His)-OH |
| ethyl | H | EtS (NCbz)$_2$-(CH$_2$-DL-Gly)-OH |
| benzyl | methyl | BnS (NCbz)$_2$-(CH$_2$-DL-Ala)-OH |
| phenethyl | 2-propyl | PhetS (NCbz)$_2$-(CH$_2$-DL-Val)-OH |
| blocked 4-hydroxyphenethyl | 2-butyl | 4-hydroxyphenethyl-S (NCbz)$_2$-(CH$_2$-DL-Ile)-OH |
| blocked 2-(4-imidazolyl)ethyl | benzyl | 2-(4-imidazolyl)ethyl-S (NCbz)$_2$-(CH$_2$-DL-Phe)-OH |
| blocked 3-carboxypropyl | blocked 4-hydroxyphenylmethyl | 3-carboxypropyls(NCbz)$_2$-(CH$_2$-DL-Tyr)-OH |
| ethyl | blocked 3-indolylmethyl | EtS (NCbz)$_2$-(CH$_2$-DL-Trp)-OH |
| benzyl | phenylethyl | BnS (NCbz)$_2$-(CH$_2$-DL-Phet)OH |
| phenethyl | blocked 4-aminobutyl | PhetS (NCbz)$_2$-(CH$_2$-DL-Lys)-OH |
| blocked 4-hydroxyphenethyl | blocked 3-guanylpropyl | (4-hydroxyphenethyl)-S (NCbz)$_2$-(CH$_2$-DL-Arg)-OH |
| blocked 2-(4-imidazolyl)ethyl | blocked 4-imidazoylmethyl | 2-(4-imidazolyl)ethyl-S (NCbz)$_2$-(CH$_2$-DL-His)-OH |
| blocked 3-carboxypropyl | H | 3-carboxypropylS(NCbz)$_2$-(CH$_2$-DL-Gly)-OH |
| ethyl | methyl | EtS (NCbz)$_2$-(CH$_2$-DL-Ala)-OH |
| benzyl | 2-propyl | BnS (NCbz)$_2$-(CH$_2$-DL-Val)-OH |
| phenethyl | 2-butyl | PhetS (NCbz)$_2$-(CH$_2$-DL-Ile)OH |
| blocked 4-hydroxyphenethyl | benzyl | 4-hydroxyphenethyl-S (NCbz)$_2$-(CH$_2$-DL-Phe)-OH |
| blocked 2-(4-imidazolyl)ethyl | blocked 4-hydroxyphenylmethyl | 2-(4-imidazolyl)-ethylS(NCbz)$_2$-(CH$_2$-DL-Tyr)-OH |
| blocked 3-carboxypropyl | blocked 3-indolylmethyl | 3-carboxypropylS(NCbz)$_2$-(CH$_2$-DL-Trp)-OH |
| ethyl | phenylethyl | EtS (NCbz)$_2$-(CH$_2$-DL-Phet)-OH |
| benzyl | blocked 4-aminobutyl | BnS (NCbz)$_2$-(CH$_2$-DL-LyS)-OH |
| phenethyl | blocked 3-guanylpropyl | PhetS (NCbz)$_2$-(CH$_2$-DL-Arg)OH |
| blocked 4-hydroxyphenethyl | blocked 4-imidazoylmethyl | 4-hydroxyphenethylS (NCbz)$_2$-(CH$_2$-DL-His)-OH |
| blocked 2-(4-imidazolyl)ethyl | H | 2-(4-imidazolyl)-ethylS (NCbz)$_2$-(CH$_2$-DL-Gly)-OH |
| blocked 3-carboxypropyl | methyl | 3-carboxypropylS(NCbz)$_2$-(CH$_2$-DL-Ala)-OH |
| ethyl | 2-propyl | EtS (NCbz)$_2$-(CH$_2$-DL-Val)-OH |
| benzyl | 2-butyl | BnS (NCbz)$_2$-(CH$_2$-DL-Ile)-OH |
| phenethyl | benzyl | PhetS (NCbz)$_2$-(CH$_2$-DL-Phe) |

-continued

Formula 23

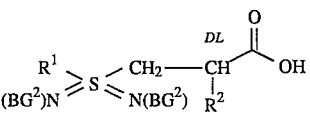

| R¹ | R² | Name |
|---|---|---|
| blocked 4-hydroxy-phenethyl | blocked 4-hydroxyphenylmethyl | OH<br>4-hydroxyphen ethylS(NCbz)₂-(CH₂-DL-Tyr)-OH |
| blocked 2-(4-imidazolyl)ethyl | blocked 3-indolylmethyl | 2-(4-imidazolyl) ethylS (NCbz)₂-(CH₂-DL-Trp)-OH |
| blocked 3-carboxy-propyl | phenylethyl | 3-carboxypropylS(NCbz)₂-(CH₂-DL-Phet)-OH |

EXAMPLE 21

PREPARATION OF
MeS(NCbz)₂-(CH₂-DL-Leu)-Trp-NHBn

21A. Formula 24 Where R¹ Is Methyl, R² Is 2-Methylpropyl, R³ Is 3-Indolylmethyl and R⁴ Is Benzyl MeS(NCbz)₂-(CH₂-DL-Leu)-OH and Trp-NHBn were coupled and the resulting mixture of two diastereomers was separated by flash chromatography on silica gel using 40% EtOAc in toluene. The faster-eluting diastereomer of MeS(NCbz)₂-(CH₂-DL-Leu)-Trp-NHBn was isolated in 39% yield. Characteristic analytical data are as follow: mp 87°–97° C. (lyophilized powder); 1H NMR (300 MHz, CDCl₃) δ7.74 (br s, 1H), 7.63 (d, J=7 Hz, 1H), 7.01–7.41 (m, 18H), 6.86 (d, J=3 Hz, 1H), 6.49 (d, J=8 Hz, 1H), 5.98 (br t, J=6 Hz, 1H), 5.10 (s, 2H), 5.08 (s, 2H), 4.67 (q, J=8 Hz, 1H), 4.29 (m, 2H), 3.81 (m, 2H), 3.24 (dd, J=7, 15 Hz, 1H), 3.15 (dd, J=8, 15 Hz, 1H), 2.98 (s, 3H), 2.82–2.91 (m, 1H), 1.38–1.50 (m, 2H), 1.21–1.28 (m, 1H), 0.78 (d, J=6 Hz, 3H), 0.77 (d, J=6 Hz, 3H); mass spectrum (PCI), m/e 404 (MH⁺-MeS(NCbz)₂H, 100); [α]²⁵_D –75° (c=0.12, MeOH). The slower-eluting diastereomer of MeS (NCbz)₂-(CH₂-DL-Leu)-Trp-NHBn was obtained in 23% yield: mp 68–78° C. (lyophilized powder); ¹H NMR (300 MHz, CDCl₃) δ7.92 (br s, 1H), 7.62 (d, J=8 Hz, 1H), 7.10–7.34 (m, 18H), 6.96 (t, J=7 Hz, 1H), 6.89 (d, J=2 Hz, 1H), 6.02 (d, J=8 Hz, 1H), 5.02 (s, 2H), 4.95 (s, 2H), 4.74 (q, J=7 Hz, 1H), 4.47 (dd, J=7, 15 Hz, 1H), 4.12 (dd, J=5, 15 Hz, 1H), 3.93 (dd, J=10, 14 Hz, 1H), 3.64 (d, J=14 Hz, 1H), 3.34 (dd, J=6, 15 Hz, 1H), 3.19 (dd, J=8, 15 Hz, 1H), 3.18 (s, 3H), 2.65–2.76 (m, 1H), 1.04–1.30 (m, 3H), 0.63 (d, J=7 Hz, 3H), 0.58 (d, J=6 Hz, 3H); mass spectrum (PCI), m/e 404 (MH⁺-MeS(NCbz)₂H, 100); [α]²⁵_D –25° (c=0.14, MeOH).

21B. Formula 24 Where R¹ Is n-Butyl, R² Is 2-Methylpropyl, R³ Is Benzyl and R⁵ Is Methyl By following the procedures described in Example 21A and substituting MeS(NCbz)₂-(CH₂-DL-Leu)-OH and Trp-NHBn with n-BuS (NCbz)₂-(CH₂-DL-Leu)-OH and Phe-Ala-NH₂, n-BuS(NCbz)₂-(CH₂-DL-Leu)-Phe-Ala-NH₂ was obtained as a mixture of two diastereomers. Separation into individual diastereomers was achieved using preparative thin-layer chromatography on silica gel (eluting three times with CHCl₃:EtOH 30:1). Characteristic analytical data are as follows for the faster-eluting diastereomer: ¹H NMR (300 MHz, CDCl₃) δ7.53 (d, J=7 Hz, 1H, NH), 7.15–7.39 (m, 15H), 6.59 (br s, 1H, NH), 6.26 (d, J=7 Hz, 1H, NH), 5.14 (d, J=12 Hz, 1H), 5.08 (s, 2H), 5.04 (d, J=12 Hz, 1H), 4.93 (br s, 1H, NH), 4.67 (m, 1H), 4.34 (p, J=7 Hz, 1H), 4.15 (dd, J=11, 13 Hz, 1H), 3.65–3.88 (m, 2H), 3.29–3.38 (m, 2H), 2.75 (dd, J=10, 14 Hz, 1H), 2.7–2.8 (br m, 1H), 1.54–1.75 (m, 4H), 1.33 (d, J=7 Hz, 3H), 1.22–1.44 (m, 3H), 0.90 (t, J=7 Hz, 3H), 0.67 (d, J=7 Hz, 3H), 0.60 (d, J=6 Hz, 3H); mass spectrum (PCI), m/e 346 (MH⁺-BuS(NCbz)₂H, 100); [α]²⁵_546 –107° (c=0.026, MeOH). Characteristic analytical data for the slower-eluting diastereomer are as follows: ¹H NMR (300 MHz, CDCl₃) δ7.14–7.39 (m, 16H), 6.41 (d, J=8 Hz, 1H, NH), 6.24 (br s, 1H, NH), 5.30 (br s, 1H, NH), 5.10 (s, 4H), 4.51 (q, J=7 Hz, 1H), 4.40 (p, J=8 Hz, 1H), 3.91 (dd, J=10, 14 Hz, 1H), 3.65 (m, 1H), 3.55 (dd, J=2, 14 Hz, 1H), 3.29 (m, 1H), 3.05 (m, 1H), 2.98 (d, J=8 Hz, 2H), 1.5–1.70 (m, 4H), 1.21–1.56 (m, 3H), 1.25 (d, J=7 Hz, 3H), 0.87 (t, J=7 Hz, 3H), 0.81 (d, J=6 Hz, 3H), 0.78 (d, J=6 Hz, 3H); mass spectrum (PCI), m/e 346 (MH⁺-BuS(NCbz)₂H, 100); [α]²⁵_546 –23° (c=0.048, MeOH).

21C. Formula 24 Where R¹ Is n-Butyl, R² Is 4-Methoxyphenylmethyl, R³ Is 3-Indolylmethyl and R⁴ Is Benzyl By following the procedures described in Example 21A and substituting MeS(NCbz)₂-(CH₂-DL-Leu)-OH with n-BuS (NCbz)₂-(CH₂-DL-TyrOMe)-OH, n-BuS(NCbz)₂-(CH2 -DL-TyrOMe)-Trp-NHBn was obtained as a mixture of two diastereomers, which were separated by flash chromatography on silica gel (35% ethyl acetate in hexane). The faster-eluting diastereomer of n-BuS(NCbz)₂-(CH₂-DL-TyrOMe)-Trp-NHBn was isolated in 43% yield. Characteristic analytical data are as follows: ¹H NMR (300 MHz, CDCl₃) δ7.84 (s, 1H), 7.65 (d, J=8 Hz, 1H), 7.04–7.40 (m, 16H), 6.95 (m, 2H), 6.90 (d, J=3 Hz, 1H), 6.86 (d, J=9 Hz, 2H), 6.61 (d, J=9 Hz, 2H), 6.24 (d, J=8 Hz, 1H), 5.56 (t, J=6 Hz, 1H), 5.10 (m, 4H), 4.54 (q, J=7 Hz, 1H), 4.17 (dd, J=3, 6 Hz, 2H), 4.02 (dd, J=10, 14 Hz, 1H), 3.60 (s, 3H), 3.5–3.64 (m, 2H), 3.04–3.22 (m, 4H), 2.77 (dd, J=9, 14 Hz, 1H), 2.66 (dd, J=7, 14 Hz, 1H), 1.53 (m, 2H), 1.11 (m, 2H), 0.80 (t, J=7 Hz, 3H), The slower-eluting diastereomer of n-BuS(NCbz)₂-(CH₂-DL-TyrOMe)-Trp-NHBn was obtained in 42% yield. Characteristic analytical data are as follows: ¹H NMR (300 MHz, CDCl₃) δ7.98 (s, 1H), 7.38 (d, J=8 Hz, 1H), 6.98–7.34 (m, 19H), 6.91 (d, J=9 Hz, 2H), 6.78 (d, J=9 Hz, 2H), 2.60 (d, J=3 Hz, 1H), 6.07 (d, J=8 Hz, 1H), 4.93 (s, 2H), 4.87 (d, J=13 Hz, 1H), 4.76 (d, J=13 Hz, 1 H), 4.63 (q, J=6 Hz, 1H), 4.37 (dd, J=6, 15 Hz, 1H), 3.99–4.16 (m, 2H), 3.75 (s, 3H), 3.41–3.52 (m, 2H), 3.31 (m, 1H), 3.19 (dd, J=6, 15 Hz, 1H), 2.94 (m, 2H), 2.72 (dd, J=6, 13 Hz, 1H), 2.59 (dd, J=7, 13 Hz, 1H), 1.48 (m, 2H), 1.22 (m, 2H), 0.80 (t, J=7 Hz, 3H).

21D. Formula 24 Where $R^1$ Is n-Butyl, $R^2$ Is 2-Methylpropyl, $R^3$ Is 3-Indolylmethyl and $R^4$ Is Benzyl By following the procedures described in Example 21A and substituting MeS(NCbz)$_2$-(CH$_2$-DL-Leu)-OH with n-BuS(NCbz)$_2$-(CH$_2$-DL-Leu)OH, n-BuS(NCbz)$_2$-(CH$_2$-DL-Leu)-Trp-NHBn was obtained as a mixture of two diastereomers, which were separated by flash chromatography on silica gel (20% EtOAc in toluene). The faster-eluting diastereomer of n-BuS(NCbz)$_2$-(CH$_2$-DL-Leu)-Trp-NHBn was isolated in 45% yield as a solid. Characteristic analytical data are as follows: mp 76°–78° C. (ether); $^1$H NMR (300 MHz, CDCl$_3$) δ7.84 (br s, 1H, NH), 7.65 (d, J=8 Hz, 1H), 7.06–7.40 (m, 16H), 7.0 (m, 2H), 6.92 (d, J=2 Hz, 1H), 6.51 (br d, J=7 Hz, 1H, NH), 5.95 (br t, J=5 Hz, 1H, NH), 5.14 (d, J=13 Hz, 1H), 5.09 (s, 2H), 5.07 (d, J=13 Hz, 1H), 4.59 (q, J=7 Hz, 1H), 4.28 (dd, J=5, 15 Hz, 1H), 4.26 (dd, J=6, 15 Hz, 1H), 3.90 (dd, J=10, 14 Hz, 1H), 3.51–3.70 (m, 2H), 3.25 (dd, J=7, 14 Hz, 1H), 3.16 (dd, J=7, 15 Hz, 1H), 3.0 (m, 1H), 2.84 (m, 1H), 1.56 (m, 2H), 1.43 (m, 2H), 1.25 (m, 1H), 1.07 (m, 2H), 0.78 (t, J=7 Hz, 3H), 0.75 (d, J=6 Hz, 6H); mass spectrum (PCI), m/e 404 (MH$^+$-BuS(NCbz)$_2$H, 44); [α]$^{25}_D$–56° (c=0.18, MeOH). The slower-eluting diastereomer of n-BuS(NCbz)$_2$(CH$_2$-DL-Leu)-Trp-NHBn was also isolated in 45% yield as a solid. Characteristic analytical data are as follows: mp 59°–61° C. (ether); $^1$H NMR (300 MHz, CDCl$_3$) δ8.01 (br s, 1H, NH), 7.61 (d, J=8 Hz, 1H), 7.08–7.32 (m, 19 H), 6.88 (d, J=2 Hz, 1H), 6.0 (br m, 1H, NH), 5.0 (s, 2H), 4.95 (d, J=12 Hz, 1H), 4.90 (d, J=12 Hz, 1H), 4.77 (q, J=8 Hz, 1H), 4.46 (dd, J=6, 15 Hz, 1H), 4.14 (dd, J=4, 15 Hz, 1H), 3.97 (dd, J=11, 14 Hz, 1H), 3.32–3.62 (m, 4H), 3.17 (dd, J=8, 15 Hz, 1H), 2.70 (m, 1H), 1.52 (m, 2H), 1.02–1.32 (m, 5H), 0.82 (t, J=7 Hz, 3H), 0.61 (d, J=6 Hz, 3H), 0.55 (d, J=6 Hz, 3H); mass spectrum (PCI), m/e 404 (MH$^+$-BuS(NCbz)$_2$H, 82); [α]$^{25}_{546}$+2.2° (c= 0.12, MeOH).

21E. Formula 24 Varying $R^1$, $R^2$, $R^3$, $R^4$ and $R^5$

By following the procedures described in Examples 21A and substituting MeS(NCbz)$_2$-(CH$_2$-DL-Leu)-OH with other compounds of Formula 23 (e.g., compounds with $R^1$ and $R^2$ that are prepared according to Example 21A and exemplified with Example 21D) and Trp-NHBn with other compounds of Formula 6 (e.g., compounds with $R^3$, $R^4$ and $R^5$ that are prepared according to Example 5A and exemplified with Example 5B), for example there are obtained the following correspondingly substituted compounds of Formula 24.

Formula 24

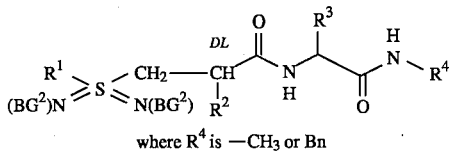

where $R^4$ is —CH$_3$ or Bn

| $R^1$ | $R^2$ | $R^3$ | $R^4$ |
|---|---|---|---|
| ethyl | H | H | —CH$_3$ |
| benzyl | methyl | methyl | —Bn |
| phenethyl | 2-propyl | 2-propyl | —CH$_3$ |
| blocked 4-hydroxyphenethyl | 2-butyl | 2-butyl | —Bn |
| blocked 2-(4-imidazolyl)ethyl | benzyl | 2-methylpropyl | —CH$_3$ |
| blocked 3-carboxypropyl | blocked 4-hydroxyphenylmethyl | blocked 4-aminobutyl | —Bn |
| blocked 3-carboxypropyl | 4-methoxyphenylmethyl | blocked 3-guanylpropyl | —CH$_3$ |
| blocked 2-(4-imidazolyl)ethyl | blocked 3-indolylmethyl | blocked 4-imidazoylmethyl | —Bn |
| blocked 4-hydroxyphenethyl | phenylethyl | benzyl | —CH$_3$ |
| phenethyl | blocked 4-aminobutyl | blocked 4-hydroxyphenylmethyl | —Bn |
| benzyl | blocked 3-guanylpropyl | 3-indoylmethyl | —CH$_3$ |
| ethyl | blocked 4-imidazoylmethyl | 4-methoxyphenylmethyl | —Bn |
| blocked 3-carboxypropyl | H | phenylethyl | —CH$_3$ |
| blocked 2-(4-imidazolyl)ethyl | methyl | thiolmethyl | —Bn |
| blocked 4-hydroxyphenethyl | 2-propyl | methylthioethyl | —CH$_3$ |
| phenethyl | 2-butyl | methylthioethyl | —Bn |
| benzyl | benzyl | thiolmethyl | —CH$_3$ |
| ethyl | blocked 4-hydroxyphenylmethyl | phenylethyl | —Bn |
| ethyl | 4-methoxyphenylmethyl | 4-methoxyphenylmethyl | —CH$_3$ |
| benzyl | blocked 3-indolylmethyl | 3-indolymethyl | —Bn |
| phenethyl | phenylethyl | blocked 4-hydroxyphenylmethyl | —CH$_3$ |
| blocked 4-hydroxy- | blocked 4- | benzyl | —Bn |

-continued

Formula 24

| | | | |
|---|---|---|---|
| phenethyl | aminobutyl | | |
| blocked 2-(4-imidazolyl)ethyl | blocked 3-guanylpropyl | blocked 4-imidazoylmethyl | —CH$_3$ |
| blocked 3-carboxypropyl | blocked 4-imidazoylmethyl | blocked 3-guanylpropyl | —Bn |
| blocked 3-carboxypropyl | H | blocked 4-aminobutyl | —CH$_3$ |
| blocked 2-(4-imidazolyl)ethyl | methyl | 2-methylpropyl | —Bn |
| blocked 4-hydroxyphenethyl | 2-propyl | 2-butyl | —CH$_3$ |
| phenethyl | 2-butyl | 2-propyl | —Bn |
| benzyl | benzyl | methyl | —CH$_3$ |
| ethyl | blocked 4-hydroxyphenylmethyl | H | —Bn |

$$\begin{array}{c} R^1 \\ (BG^2)N \end{array} \!\!\!\!> \!\!S\!\!<\!\!\!\! \begin{array}{c} CH_2 \\ N(BG^2) \end{array} \!\!-\!\! \overset{DL}{\underset{R^2}{CH}}\!\!-\!\! \overset{O}{\underset{}{C}}\!\!-\!\! \overset{R^3}{\underset{H}{N}}\!\!-\!\! \overset{H}{\underset{O}{C}}\!\!-\!\! \overset{}{\underset{}{N}}\!\!-\!\!R^4$$

where R$^4$ is —CH(R$^5$)—C(O)NH$_2$

| R$^1$ | R$^2$ | R$^3$ | R$^5$ |
|---|---|---|---|
| ethyl | H | H | methylthioethyl |
| benzyl | methyl | methyl | thiolmethyl |
| phenethyl | 2-propyl | 2-propyl | phenylethyl |
| blocked 4-hydroxyphenethyl | 2-butyl | 2-butyl | 4-methoxyphenylmethyl |
| blocked 2-(4-imidazolyl)ethyl | benzyl | 2-methylpropyl | 3-indoylmethyl |
| blocked 3-carboxypropyl | blocked 4-hydroxyphenylmethyl | blocked 4-aminobutyl | blocked 4-hydroxyphenylmethyl |
| blocked 3-carboxypropyl | 4-methoxyphenylmethyl | blocked 3-guanylpropyl | benzyl |
| blocked 2-(4-imidazolyl)ethyl | blocked 3-indolylmethyl | blocked 4-imidazoylmethyl | blocked 4-imidazoylmethyl |
| blocked 4-hydroxyphenethyl | phenylethyl | benzyl | blocked-3-guanylpropyl |
| phenethyl | blocked 4-aminobutyl | blocked 4-hydroxyphenylmethyl | blocked 4-aminobutyl |
| benzyl | blocked 3-guanylpropyl | 3-indoylmethyl | 2-methylpropyl |
| ethyl | blocked 4-imidazoylmethyl | 4-methoxyphenylmethyl | 2-butyl |
| blocked 3-carboxypropyl | H | phenylethyl | 2-propyl |
| blocked 2-(4-imidazolyl)ethyl | methyl | thiolmethyl | methyl |
| blocked 4-hydroxyphenethyl | 2-propyl | methylthioethyl | H |
| phenethyl | 2-butyl | methylthioethyl | H |
| benzyl | benzyl | thiolmethyl | methyl |
| ethyl | blocked 4-hydroxyphenylmethyl | phenylethyl | 2-propyl |
| ethyl | 4-methoxyphenylmethyl | 4-methoxyphenylmethyl | 2-butyl |
| benzyl | blocked 3-indolylmethyl | 3-indoylmethyl | 2-methylpropyl |
| phenethyl | phenylethyl | blocked 4-hydroxyphenylmethyl | blocked 4-aminobutyl |
| blocked 4-hydroxyphenethyl | blocked 4-aminobutyl | benzyl | blocked-3-guanylpropyl |

-continued

Formula 24

| | | | |
|---|---|---|---|
| blocked 2-(4-imidazolyl)ethyl | blocked 3-guanylpropyl | blocked 4-imidazoylmethyl | blocked 4-imidazoylmethyl |
| blocked 3-carboxypropyl | 4-imidazoylmethyl | blocked 3-guanylpropyl | benzyl |
| blocked 3-carboxypropyl | H | blocked 4-aminobutyl | blocked 4-hydroxyphenylmethyl |
| blocked 2-(4-imidazolyl)ethyl | methyl | 2-methylpropyl | 3-indoylmethyl |
| blocked 4-hydroxyphenethyl | 2-propyl | 2-butyl | 4-ethoxyphenylmethyl |
| phenethyl | 2-butyl | 2-propyl | phenylethyl |
| benzyl | benzyl | methyl | thiolmethyl |
| ethyl | blocked 4-hydroxyphenylmethyl | H | methylthioethyl |

EXAMPLE 22

PREPARATION OF MeS(NH)$_2$-(CH$_2$-DL-Leu)-Trp-NHBn

22A. Formula I Where X Is NH, R$^1$ Is Methyl, R$^2$ Is 2-Methylpropyl, R$^3$ Is 3-Indolylmethyl and R$^4$ Is Benzyl To 21 mg (0.207 mmol) of MeS(NCbz)$_2$-(CH$_2$-DL-Leu)-Trp-NHBn (fastereluting diastereomer) in 5 mL of EtOH was added 9 mg of 10% Pd/C and 2 drops of cyclohexylamine, and hydrogen gas was bubbled through the mixture for 3 h. The reaction mixture was filtered and the solid was washed with EtOH. The combined filtrates were evaporated under vacuum and the residue was purified by flash chromatography (10% MeOH in CH$_2$Cl$_2$) to give 11 mg (86% yield) of MeS(NH)$_2$-(CH$_2$-DL-Leu)-Trp-NHBn (faster-eluting diastereomer) as a solid: mp 94°–96° C.; $^1$H NMR (300 MHz, CDC$_3$) δ8.36 (s, 1H), 7.68 (d, J=8 Hz, 1H), 7.36 (d, J=8 Hz, 1H), 7.02–7.30 (m, 9H), 6.68 (t, J=6 Hz, 1H), 4.77 (q, J=7 Hz, 1H), 4.35 (dd, J=6, 15 Hz, 1H), 4.30 (dd, J=6, 15 Hz, 1H), 3.22–3.42 (m, 3H), 2.88 (m, 2H), 2.63 (s, 3H), 1.4–1.6 (m, 2H), 1.2 (m, 1H), 0.85 (d, J=7 Hz), 3H), 0.82 (d, J=7 Hz, 3H); mass spectrum (PCI), m/e 404 (MH$^+$-MeS(NH)$_2$H, 100).

The same procedure applied to the slower-eluting diastereomer of MeS(NCbz)$_2$-(CH$_2$-DL-Leu)-Trp-NHBn afforded an 81% yield of MeS(NH)$_2$-(CH$_2$-DL-Leu)-Trp-NHBn (slower-eluting diastereomer): mp 92°–94° C.; $^1$H NMR (300 MHz, CDCl$_3$) δ8.12 (s, 1H), 7.73 (t, J=5 Hz, 1H), 7.65 (d, J=7 Hz, 1H), 7.39 (d, J=5 Hz, 1H), 7.1–7.3 (m, 7H), 7.02 (d, J=3 Hz, 1H), 6.48 (d, J=8 Hz, 4.87 (q, J=6 Hz, 1H), 4.35 (dd, J=6, 15 Hz, 1H), 4.30 (dd, J=6, 15 Hz, 1H), 3.67 (dd, J=11, 14 Hz, 1H), 3.46 (dd, J=6, 15 Hz, 1H), 3.31 (dd, J=6, 15 Hz, 1H), 2.86 (d, J=12 Hz, 1H), 2.78 (s, 3H), 2.70 (m, 1H), 1.5 (m, 1H), 1.26 (m1), 1.14 (m, 1H), 0.76 (d, J=7 Hz, 3H), 0.74 (d, J=7 Hz, 3H); mass spectrum (PCI), m/e 404 (MH$^+$-MeS(NH)$_2$H, 100).

22B. Formula I Where X Is NH, R$^1$ Is n-Butyl, R$^2$ Is 2-Methylpropyl, R$^3$ Is Benzyl and R$^5$ Is Methyl By following the procedures described in Example 22A and substituting MeS(NCbz)$_2$-(CH$_2$-DL-Leu)-Trp-NHBn with n-BuS(NCbz)$_2$-(CH$_2$-DL-Leu)-Phe-Ala-NH$_2$, 4.5 mg (95% yield) of the faster-eluting diastereomer of n-BuS(NH)$_2$-(CH$_2$-DL-Leu)-Phe-Ala-NH$_2$ was obtained. Characteristic analytical data are as follows: 1H NMR (300 MHz, CDCl$_3$) δ8.23 (br d, J=8 Hz, 1H, NH), 7.19–7.38 (m,), 6.82 (br s, 1H, NH), 6.34 (br d, J=7 Hz, 1H, NH), 5.32 (br s, 1H, NH), 4.52–4.63 (m, 2H), 3.61 (dd, J=11, 14 Hz, 1H), 3.38 (dd, J=5, 14 Hz, 1H), 2.91–3.03 (m, 3H), 2.66–2.80 (m, 2H), 1.36–1.58 (m, 3H), 1.32 (d, J=7 Hz, 3H), 1.22–1.30 (m, 1H), 0.94 (t, J=8 Hz, 3H), 0.90–1.22 (m, 3H), 0.75 (d, J= 7 Hz, 3H), 0.66 (d, J=6 Hz, 3H); mass spectrum (PCI), m/e 466 (MH$^+$, 17), 346 (MH$^+$-BuS(NH)$_2$H, 100).

The same procedure applied to the slower-eluting diastereomer of n-BuS(NCbz)$_2$-(CH$_2$-DL-Leu)-Phe-Ala-NH$_2$ afforded a 66% yield of n-BuS(NH)$_2$-(CH$_2$-Dl-Leu)-Phe-Ala-NH$_2$ (slower-eluting diastereomer): $^1$H NMR (300 MHz, CDCl$_3$) δ7.20–7.40 (m, 6H), 6.96 (br m, 1H, NH), 6.42 (br s, 1H, NH), 5.37 (br s, 1H, NH), 4.44–4.54 (m, 2H), 3.22–3.36 (m, 2H), 3.05 (dd, J=9, 15 Hz, 1H), 2.79–2.97 (m, 3H), 1.1–1.8 (m, 7H), 1.35 (d, J=7 Hz, 3H), 0.97 (t, J=7 Hz, 3H), 0.88 (d, J=7 Hz, 3H), 0.81 (d, J=6 Hz, 3H); mass spectrum (PCI), m/e 466 (MH$^+$, 21), 346 (MH$^+$-BuS(NH)$_2$H, 100).

22C. Formula I Where X Is NH, R$^1$Is n-Butyl, R$^2$ Is 4-Methoxyphenylmethyl, R$^3$ Is 3-Indolylmethyl and R$^4$ Is Benzyl By following the procedures described in Example 22A and substituting MeS(NCbz)$_2$-(CH$_2$-DL-Leu)-Trp-NHBn with n-BuS(NCbz)$_2$-(CH$_2$-DL-TYrOMe)-Trp-NHBn, 12 mg (69% yield) of n-BuS(NH)$_2$-(CH$_2$-DL-TyrOMe)-Trp-NHBn (faster-eluting diastereomer) was obtained as a solid. Characteristic analytical data are as follows: mp 85°–87° C.; $^1$H NMR (300 MHz, CD$_3$OD) δ7.58 (d, J=8 Hz, 1H), 7.30 (d, J=8 Hz, 1H), 7.19–6.93 (m, 10H), 6.69 (d, J=8 Hz, 2H), 4.56 (t, J=7 Hz, 1H), 4.22 (d, J=15 Hz, 1H), 4.13 (d, J=15 Hz, 1H), 3.65 (s, 3H), 3.46 (dd, J=10, 14 Hz, 1H), 3.25 (dd, J=7, 15 Hz, 1H), 3.07 (dd, J=8, 15 Hz, 2H), 2.91–2.76 (m, 2H), 2.69–2.57 (m, 3H), 1.57–1.30 (m, 2H), 1.16 (m, 2H), 0.79 (t, J=7 Hz, 3H); mass spectrum (PCI), m/e 468 (MH$^+$-BuS(NH)$_2$H, 100).

The same procedure applied to the slower-eluting diastereomer of n-BuS(NCbz)$_2$-(CH$_2$-DL-TyrOMe)-Trp-NHBn afforded a 75% yield of n-BuS(NH)$_2$-(CH$_2$-DL-TyrOMe)-Trp-NHBn (slower-eluting diastereomer) as a solid. Characteristic analytical data are as follows: mp 130°–132° C.; $^1$H NMR (300 MHz, CDCl$_3$) δ8.18 (br s, 1H, NH), 7.85 (br t, J=6 Hz, 1H, NH), 7.36 (d, J=9 Hz, 2H), 6.98–7.24 (m, 10H), 6.87 (d, J=9 Hz, 2H), 6.67 (m, 1H, NH), 6.22 (br d, J=9 Hz, 1H, NH), 4.78 (m, 1H), 4.32 (dd, J=6, 15 Hz, 1H), 4.25 (dd, J=5, 15 Hz, 1H), 3.78 (s, 3H), 3.59 (dd, J=10, 14 Hz, 1H), 3.47 (dd, J=6, 15 Hz, 1H), 2.55–2.99 (m, 7H), 1.18–1.52 (m, 4H), 0.85 (t, J=7 Hz, 3H); mass spectrum (PCI), m/e 468 (MH$^+$-BuS(NH)$_2$H, 100).

22D. Formula I Where X Is NH, $R^1$ Is n-Butyl, $R^2$ Is Isobutyl, $R^3$ Is 3-Indolylmethyl and $R^4$ Is Benzyl By following the procedures described in Example 22A and substituting MeS(NCbz)$_2$-(CH$_2$-DL-Leu)-Trp-NHBn with n-BuS(NCbz)$_2$-(CH$_2$-DL-Leu)-Trp-NHBn, 23 mg (83% yield) of n-BuS(NH)$_2$-(CH$_2$-DL-Leu)-Trp-NHBn (faster-eluting diastereomer) was obtained as a solid. Characteristic analytical data are as follows: mp 80°–81° C.; $^1$H NMR (300 MHz, CDCl$_3$) δ8.41 (br s, 1H, NH), 7.68 (d, J=8 Hz, 1H), 7.36 (d, J=8 Hz, 1H), 7.00–7.25 (m, 9H), 6.80 (br t, J=5 Hz, 1H, NH), 4.76 (q, J=7 Hz, 1H), 4.31 (d, J=6 Hz, 2H), 3.19–3.41 (m, 3H), 2.62–2.93 (m, 1.40–1.68 (m, 4H), 1.16–1.39 (m, 3H), 0.89 (t, J=7 Hz, 3H), 0.85 (d, J=6 Hz, 3H), 0.81 (d, J=6 Hz, 3H); mass spectrum (PCI), m/e 404 (MH$^+$-BuS(NH)$_2$H, 100).

By the same procedure 28 mg of n-BuS(NCbz)$_2$-(CH$_2$-DL-Leu)-Trp-NHBn (slower-eluting diastereomer) afforded 18 mg (97% yield) of n-BuS(NH)$_2$-(CH$_2$-DL-Leu)-Trp-NHBn (slower-eluting diastereomer) as a solid: mp 143°–145° C.; $^1$H NMR (300 MHz, CDCl$_3$) δ8.27 (br s, 1H, NH), 8.03 (br t, J=5 Hz, 1H, NH), 7.65 (d, J=8 Hz, 1H), 7.39 (d, J=8 Hz, 1H), 7.29–7.10 (m, 7H), 7.0 (d, J=2 Hz, 1H), 6.24 (br d, J=9 Hz, 1H, NH), 4.90 (m, 1H), 4.38 (dd, J=6, 15 Hz, 1H), 4.30 (dd, J=5, 15 Hz, 1H), 3.54 (dd, J=11, 14 Hz, 1H), 3.47 (dd, J=6, 15 Hz, 1H), 3.30 (dd, J=5, 15 Hz, 1H), 2.82–2.54 (m, 4H), 1.53 (m, 2H), 1.30 (m, 4H), 1.13 (m, 1H), 0.88 (t, J=7 Hz, 3H), 0.76 (d, J=6 Hz, 3H), 0.73 (d, J= 6 Hz, 3H); mass spectrum (PCI), m/e 524 (MH$^+$, 6), 404 (MH$^+$-BuS(NH)$_2$H, 97).

22C. Formula I Varying $R^1$, $R^2$, $R^3$, $R^4$ and $R^5$

By following the procedures described in Example 22A and substituting MeS(NCbz)2-(CH2-DL-Leu)-TrP-NHBn with other compounds of Formula 24 (where $R^1$, $R^2$, $R^3$, $R^4$ and $R^5$ are as indicated in the table below), for example there are obtained the corresponding substituted compounds of Formula I.

Formula I

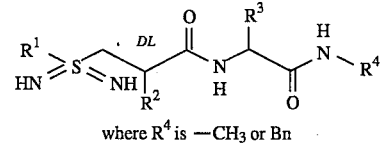

where $R^4$ is —CH$_3$ or Bn

| $R^1$ | $R^2$ | $R^3$ | $R^4$ |
| --- | --- | --- | --- |
| ethyl | H | H | —CH$_3$ |
| benzyl | methyl | methyl | —Bn |
| phenethyl | 2-propyl | 2-propyl | —CH$_3$ |
| 4-hydroxyphenethyl | 2-butyl | 2-butyl | —Bn |
| 2-(4-imidazolyl)ethyl | benzyl | 2-methylpropyl | —CH$_3$ |
| 3-carboxypropyl | 4-hydroxyphenylmethyl | 4-aminobutyl | —Bn |
| 3-carboxypropyl | 4-methoxyphenylmethyl | 3-guanylpropyl | —CH$_3$ |
| 2-(4-imidazolyl)ethyl | 3-indolylmethyl | 4-imidazoylmethyl | —Bn |
| 4-hydroxyphenethyl | phenylethyl | benzyl | —CH$_3$ |
| phenethyl | 4-aminobutyl | 4-hydroxyphenylmethyl | —Bn |
| benzyl | 3-guanylpropyl | 3-indolymethyl | —CH$_3$ |
| ethyl | 4-imidazoylmethyl | 4-methoxyphenylmethyl | —Bn |
| 3-carboxypropyl | H | phenylethyl | —CH$_3$ |
| 2-(4-imidazolyl)ethyl | methyl | thiolmethyl | —Bn |
| 4-hydroxyphenethyl | 2-propyl | methylthioethyl | —CH$_3$ |
| phenethyl | 2-butyl | methylthioethyl | —Bn |
| benzyl | benzyl | thiolmethyl | —CH$_3$ |
| ethyl | 4-hydroxyphenylmethyl | phenylethyl | —Bn |
| ethyl | 4-methoxyphenylmethyl | 4-methoxyphenylmethyl | —CH$_3$ |
| benzyl | 3-indolylmethyl | 3-indoylmethyl | —Bn |
| phenethyl | phenylethyl | 4-hydroxyphenylmethyl | —CH$_3$ |
| 4-hydroxyphenethyl | 4-aminobutyl | benzyl | —Bn |
| 2-(4-imidazolyl)ethyl | 3-guanylpropyl | 4-imidazoylmethyl | —CH$_3$ |
| 3-carboxypropyl | 4-imidazoylmethyl | 3-guanylpropyl | —Bn |
| 3-carboxypropyl | H | 4-aminobutyl | —CH$_3$ |
| 2-(4-imidazolyl)ethyl | methyl | 2-methylpropyl | —Bn |
| 4-hydroxyphenethyl | 2-propyl | 2-butyl | —CH$_3$ |
| phenethyl | 2-butyl | 2-propyl | —Bn |
| benzyl | benzyl | methyl | —CH$_3$ |
| ethyl | 4-hydroxyphenylmethyl | H | —Bn |

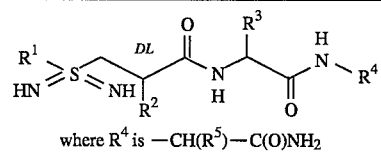

where $R^4$ is —CH($R^5$)—C(O)NH$_2$

-continued

Formula I

| R¹ | R² | R³ | R⁵ |
|---|---|---|---|
| ethyl | H | H | methylthioethyl |
| benzyl | methyl | methyl | thiolmethyl |
| phenethyl | 2-propyl | 2-propyl | phenylethyl |
| 4-hydroxyphenethyl | 2-butyl | 2-butyl | 4-methoxyphenylmethyl |
| 2-(4-imidazolyl)ethyl | benzyl | 2-methylpropyl | 3-indoylmethyl |
| 3-carboxypropyl | 4-hydroxyphenylmethyl | 4-aminobutyl | 4-hydroxyphenylmethyl |
| 3-carboxypropyl | 4-methoxyphenylmethyl | 3-guanylpropyl | benzyl |
| 2-(4-imidazolyl)ethyl | 3-indolylmethyl | 4-imidazoylmethyl | 4-amidazoylmethyl |
| 4-hydroxyphenethyl | phenylethyl | benzyl | 3-guanylpropyl |
| phenethyl | 4-aminobutyl | 4-hydroxyphenylmethyl | 4-aminobutyl |
| benzyl | 3-guanylpropyl | 3-indoylmethyl | 2-methylpropyl |
| ethyl | 4-imidazoylmethyl | 4-methoxyphenylmethyl | 2-butyl |
| 3-carboxypropyl | H | phenylethyl | 2-propyl |
| 2-(4-imidazolyl)ethyl | methyl | thiolmethyl | methyl |
| 4-hydroxyphenethyl | 2-propyl | methylthioethyl | H |
| phenethyl | 2-butyl | methylthioethyl | H |
| benzyl | benzyl | thiolmethyl | methyl |
| ethyl | 4-hydroxyphenylmethyl | phenylethyl | 2-propyl |
| ethyl | 4-methoxyphenylmethyl | 4-methoxyphenylmethyl | 2-butyl |
| benzyl | 3-indolylmethyl | 3-indoylmethyl | 2-methylpropyl |
| phenethyl | phenylethyl | 4-hydroxyphenylmethyl | 4-aminobutyl |
| 4-hydroxyphenethyl | 4-aminobutyl | benzyl | 3-guanylpropyl |
| 2-(4-imidazolyl)ethyl | 3-guanylpropyl | 4-imidazoylmethyl | 4-imidazoylmethyl |
| 3-carboxypropyl | 4-imidazoylmethyl | 3-guanylpropyl | benzyl |
| 3-carboxypropyl | H | 4-aminobutyl | 4-hydroxyphenylmethyl |
| 2-(4-imidazolyl)ethyl | methyl | 2-methylpropyl | 3-indoylmethyl |
| 4-hydroxyphenethyl | 2-propyl | 2-butyl | 4-ethoxyphenylmethyl |
| phenethyl | 2-butyl | 2-propyl | phenylethyl |
| benzyl | benzyl | methyl | thiolmethyl |
| ethyl | 4-hydroxyphenylmethyl | H | methylthioethyl |

EXAMPLE 23

PREPARATION OF BnS-(CH₂-L-Leu-CH₂)-OH

23A. Formula 25 Where R² Is 2-Methylpropyl

Following the procedure described in Hollady (Hollady, M. W.; Salituro, F. G.; Rich, D. H., *J. Med Chem.* 1987, 30, 374–383), to 53 mL of absolute EtOH was added 1.71 g of $CaCl_2$. The mixture was stirred at room temperature under $N_2$ until the solid was mostly dissolved. The solution was cooled to 0° C. and 1.17 g of $NaBH_4$ was added and the mixture was stirred for 0.5 h. To the cold solution was added 6.33 g of (4S, 5R)-3-[(2S)-1-oxo-2-[(benzylthio)methyl]-4-methylpentyl]-4-methyl-5-phenyl-2-oxazolidinone in 18 mL of THF dropwise over 15 minutes (an additional 17 mL of THF was used to rinse residual starting material into the reaction flask). The reaction mixture was stirred at 0° C. under $N_2$ for 4 h. The reaction was quenched by addition of 50 mL of EtOAc, 10 mL of $H_2O$ and 20% HOAc until effervescence ceased. The mixture was acidified to pH 2 with 3N HCl and the aqueous layer was extracted with EtOAc. The organic extract was washed with saturated $NaHCO_3$ and saturated NaCl, dried over $Na_2SO_4$ and evaporated to give a yellow oil. The crude product was purified by flash chromatography on silica gel (hexane-20% EtOAc) to give 3.19 g (87% yield) of BnS-(CH₂-L-Leu-CH₂)-OH as a clear oil: $R_F$ 0.3 (hexane-20% EtOAc); ¹H NMR (300 MHz, $CDCl_3$) δ7.33–7.23 (m, 5H), 3.72 (s, 2H), 3.69–3.61 (m, 1H) 3.58–3.51 (M, 1H), 2.52 (dd, J=6, 13 Hz, 1H) 2.47 (dd, J=7, 13 Hz, 1H), 1.82–1.74 (m, 1H), 1.62–1.53 (m, 2H), 1.15 (dt, J=4, 7 Hz, 2H), 0.86 (d, J=7 Hz, 3H) 0.85 (d, J=7 Hz, 3H); $[\alpha]^{25}_D$ –22.6° (c= 3.14, $CH_2Cl_2$).

23B. Formula 25 Varying R²

By following the procedures described in Example 23A and substituting (4S, 5R)-3-[(2S)-1-oxo-2-[(benzylthio)methyl]-4-methylpentyl]-4-methyl-5-phenyl-2-oxazolidinone with other L-configuration compounds of Formula 3 there are obtained the corresponding L-configuration compounds of Formula 25.

EXAMPLE 24

PREPARATION OF BnS-(CH$_2$-L-Leu-CH$_2$)-OTBS

24A. Formula 26 Where R$^2$ Is 2-Methylpropyl

A solution of 2.83 g of BnS-(CH$_2$-L-Leu-CH$_2$)-OH, 2.16 g of imidazole, and 2.3 g of TBSCl in 15 mL of dry DMF was left at room temperature under N$_2$ for 7 h. To the mixture was added 200 mL of Et$_2$O and 50 mL of H$_2$O. The organic layer was washed with H$_2$O, dried over Na$_2$SO$_4$ and evaporated. The resulting yellow oil was purified by flash chromatography on silica gel (hexane-10% EtOAc) to give 3.82 g (91% yield) of BnS-(CH$_2$-L-Leu-CH$_2$)-OTBS as a clear oil: R$_F$ 0.8 (hexane-10% EtOAc); $^1$H NMR (300 MHz, CDCl$_3$) δ7.30–7.21 (m, 5H), 3.69 (s, 2H), 3.60 (dd, J=4, 10 Hz, 1H), 3.50 (dd, J=5, 10 Hz, 1H), 2.55 (dd, J=7, 13 Hz, 1H), 2.38 (dd, J=6, 13 Hz, 1H), 1.75–150 (m, 2H), 1.25–1.10 (m, 2H), 0.88–0.82 (m, 15H) 0.02 (s 6H); [α]$^{25}$$_D$ –4.5° (c=3.57, CH$_2$Cl$_2$).

24B. Formula 26 Varying R$^2$

By following the procedures described in Example 24A and substituting BnS-(CH$_2$-L-Leu-CH$_2$)-OH with other L-configuration compounds of Formula 25 there are obtained the corresponding L-configuration compounds of Formula 26.

EXAMPLE 25

PREPARATION OF HS-(CH$_2$-L-Leu-CH$_2$)-OTBS

25A. Formula 27 Where R$^2$ Is 2-Methylpropyl

Debenzylation of BnS-(CH$_2$-L-Leu-CH$_2$)-OTBS was carried out using the Na in liquid ammonia procedure of Evans and coworkers (Evans, D. A.; Mathre, D. J.; Scott, W. L., *J. Org. Chem.* 1985, 50, 1830–1835) to give HS-(CH$_2$-L-Leu-CH$_2$)-OTBS as a clear oil in 88% yield after flash chromatography on silica gel (hexane-10% EtOAc): R$_F$ 0.3 (hexane-2% EtOAc); $^1$H NMR (300 MHz, CDCl$_3$) δ3.57 (dd, J=5, 10 Hz, 1H), 3.47 (dd, J=7, 10 Hz, 1H), 2.60 (dd, J=5, 8 Hz, 2H), 1.78–1.66 (m, 1H), 1.65–1.52 (m, 1H), 1.25–1.10 (m, 3H), 0.90–0.86 (m, 15H), 0.04 (s, 6H); [α]$^{25}$$_D$ +9.8° (c=2.7, CH$_2$Cl$_2$).

25B. Formula 27 Varying R$^2$

By following the procedures described in Example 25A and substituting BnS-(CH$_2$-L-Leu-CH$_2$)-OTBS with other L-configuration compounds of Formula 26 there are obtained the corresponding L-configuration compounds of Formula 27.

EXAMPLE 26

PREPARATION OF MeS-(CH$_2$-L-Leu-CH$_2$)-OTBS

26A. Formula 28 Where R$^2$ Is 2-Methylpropyl

To 25 mL of 0.106M NaOMe in MeOH was added dropwise a solution of 653 mg of HS-(CH$_2$-L-Leu-CH$_2$)-OTBS in 9 mL of MeOH. To the solution was added 0.165 mL of CH$_3$I and the mixture was allowed to stand at room temperature under N$_2$ overnight. The reaction mixture was diluted with 10 mL of H$_2$O and was acidified with 5 mL of 1N HCl. The MeOH was evaporated under reduced pressure and the aqueous residue was extracted with CH$_2$Cl$_2$. The organic extract was dried over Na$_2$SO$_4$ and evaporated. The resulting yellow oil was purified by flash chromatography on silica gel, eluting first with 100% hexane then with 100% EtOAc. The EtOAc fractions afforded 328 mg of MeS-(CH$_2$-L-Leu-CH$_2$)-OH. A mixture of 328 mg of MeS-(CH$_2$-L-Leu-CH$_2$)-OH from above, 383 mg of imidazole, and 407 mg of TBSCl in 3 mL of DMF was stirred at room temperature overnight. The reaction mixture was partitioned between 100 mL of Et$_2$O and 10 mL of H$_2$O and the organic layer was washed with H$_2$O, dried over Na$_2$SO$_4$ and evaporated. The residue was purified by flash chromatography on silica gel (100% hexane) to give 390 mg (57% yield) of MeS-(CH$_2$-L-Leu-CH$_2$)-OTBS as a clear oil: R$_F$ 0.15 (hexane); $^1$H NMR (300 MHz, CDCl$_3$) δ3.63 (dd, J=5, 10 Hz, 1H), 3.53 (dd, J=5, 10 Hz, 1H), 2.60 (dd, J=7, 13 Hz, 1H), 2.44 (dd, J=5, 13 Hz, 1H), 2.08 (s, 3H), 1.80–1.73 (m, 1H), 1.69–1.60 (m, 1H), 1.30–1.15 (m, 2H), 0.90–0.87 (m 15H), 0.04 (s, 6H); [α]$^{25}$$_D$ +2.1° (c=5.81, CHCl$_3$).

26B. Formula 28 Varying R$^2$

By following the procedures described in Example 26A and substituting HS-(CH$_2$-L-Leu-CH$_2$)-OTBS with other L-configuration compounds of Formula 27 there are obtained the corresponding L-configuration compounds of Formula 28.

EXAMPLE 27

DETERMINATION OF FIBROBLAST COLLAGENASE (HFC) INHIBITION

Starting Materials and Reagents:

Pro-HFC was purified from the harvest media of human gingival fibroblasts following procedures described in Birkedal-Hansen, H. *Methods Enzymol.* 1987, 144, 140–171.

The HFC used in the assays was either zymogen that had undergone spontaneous activation, or zymogen that had been activated by treatment with 100 μg/mL of trypsin for 15 min at 23° C., followed by the addition of a 4-fold excess of soybean trypsin inhibitor.

Kinetic Measurements:

Assays were performed in 50 mM Tricine, 0.2M NaCl, 10 mM CaCl$_2$, pH 7.5 containing 5% methanol once the substrate and inhibitor were diluted into it. The buffer was freed from adventitious metal ions by extraction with dithizone in carbon tetrachloride (Holmquist, B. *Methods Enzymol.* 1988, 158, 6–10). Stock solutions of inhibitors were prepared in 100% methanol. Stock solutions of the substrate were prepared in 50% aqueous methanol at a concentration of 0.2 mM.

The assay method used was based on the hydrolysis of DNP-Pro-Leu-Ala-Leu-Trp-Ala-Arg at 24° C. (Netzel-Arnett, S.; Mallya, S. K.; Nagase, H.; Birkedal-Hansen, H.; Van Wart, H. E. *Anal. Biochem.* 1991, 195, 86–92). The fluorescence changes were monitored with a Perkin-Elmer Model LS-5 fluorometer using an excitation wavelength of 280 nm and an emission wavelength of 360 nm. The substrate concentration used in the assays was either 5 μM or 10 μM. The inhibitor was diluted into the assays using 100% methanol, and controls substituted an equal volume of methanol so that the final methanol concentration from inhibitor and substrate dilutions in all assays was 5%. For each assay, the enzyme and inhibitor were incubated in the assay buffer at 24° C. for 30 min, then the substrate was added and the rate of hydrolysis was measured by monitoring the increase in fluorescence intensity at 360 nm. The inhibition results are expressed as the inhibitor concentration that produced 50% inhibition (IC$_{50}$) of activity at the substrate concentration used.

Representative compounds of the present invention exhibited inhibition of HFC when tested by this method.

EXAMPLE 28

DETERMINATION OF NEUTROPHIL COLLAGENASE (HNC) INHIBITION

Starting Materials and Reagents:

HNC (58 kDa active form) was isolated from human buffy coats following procedures described in Mookhtiar, K. A.; Van Wart, H. E. *Biochemistry* 1990, 29, 10620–10627.

HNC was isolated in active form and no additional treatments were performed before use in assays.

Kinetic Measurements:

The preparation of enzyme, inhibitor and substrate solutions; and the assay method were performed using the procedure described in Example 21 (Kinetic Measurements Section).

Representative compounds of the present invention exhibited inhibition of HNC when tested by this method.

EXAMPLE 29

DETERMINATION OF FIBROBLAST GELATINASE (HFG) INHIBITION

Starting Materials and Reagents:

Pro-HFG was purified from the harvest media of human gingival fibroblasts following procedures described in Birkedal-Hansen, H. *Methods Enzymol.* 1987, 144, 140–171.

Spontaneously activated HFG was used without additional treatment.

Kinetic Measurements:

The preparation of enzyme, inhibitor and substrate solutions; and the assay method were performed using the procedure described in Example 21 (Kinetic Measurements Section).

Representative compounds of the present invention exhibited inhibition of HFG when tested by this method.

EXAMPLE 30

DETERMINATION OF NEUTROPHIL GELATINASE (HNG) INHIBITION

Starting Materials and Reagents:

Pro-HNG was isolated from human buffy coats following procedures described in Mookhtiar, K. A.; Van Wart, H. E. *Biochemistry* 1990, 29, 10620–10627.

Spontaneously activated HNG was used without additional treatment.

Kinetic Measurements:

The preparation of enzyme, inhibitor and substrate solutions; and the assay method were performed using the procedure described in Example 21 (Kinetic Measurements Section).

Representative compounds of the present invention exhibited inhibition of HNG when tested by this method.

EXAMPLE 31

DETERMINATION OF STROMELYSIN (HFS) INHIBITION

Starting Materials and Reagents:

Pro-HFS was isolated from the culture medium of human rheumatoid synovial cells stimulated with rabbit macrophage-conditioned medium by affinity chromatography using sheep anti-HFS IgG coupled to Affi-Gel 10 following procedures described in Ito, A.; Nagase, H. *Arch. Biochem. Biophys.* 1988, 267, 211–216.

Pro-HFS was activated by treatment with 1 m Mp-aminophenylmercuric acetate (APMA) for 24 hr at 37° C. to give a mixture of 45 and 28 kDa species, which are known to have indistinguishable specific activities and specificities (following procedures described in Okada, Y.; Nagase, H.; Harris, E. D., Jr. *J. Biol. Chem.* 1986, 261, 14245–14255). HFS was separated from the APMA by chromatography over Sephacryl S-200 and it was stored at 4° C.

Kinetic Measurements:

The preparation of enzyme, inhibitor and substrate solutions; and the assay method were performed using the procedure described in Example 21 (Kinetic Measurements Section).

Representative compounds of the present invention exhibited inhibition of HFS when tested by this method.

EXAMPLE 32

Capsule Formulation

This example illustrates the preparation of a representative pharmaceutical formulation for oral administration containing an active compound of Formula I, e.g., Me-RS-SO(NH)-(CH$_2$-L-Leu)-Phe-Ala-NH$_2$.

| Ingredients | Quantity (mg/capsule) |
|---|---|
| Active compound | 200 |
| lactose, spray-dried | 148 |
| magnesium stearate | 2 |

The above ingredients are mixed and introduced into a hard-shell gelatin capsule.

Other compounds of Formula I, such as those prepared in accordance with Reaction Schemes A and B, and Examples 1–22 can be used as the active compound in the preparation of the orally administrable formulations of this example.

EXAMPLE 33

Oral Formulation

This example illustrates the preparation of a representative pharmaceutical formulation containing an active compound of Formula I, e.g., n-Bu-S(NH)$_2$-(CH$_2$-DL-TyrOCH$_3$)-Trp-NHBn.

An suspension for oral administration is prepared having the following composition:

| Ingredients | Quantity |
|---|---|
| Active compound | 1.0 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 mL |
| colorings | 0.5 mg |
| distilled water | q.s. to 100 mL |

Other compounds of Formula I, such as those prepared in accordance with Reaction Schemes A and B, and Examples 1-22 can be used as the active compound in the preparation of the orally administrable formulations of this example.

EXAMPLE 34

Tablet Formulation

This example illustrates the preparation of a representative pharmaceutical formulation containing an active compound of Formula I, e.g., n-Bu-S(NH)$_2$-(CH$_2$-DL-Leu)-Trp-NHBn.

A tablet for oral administration is prepared having the following composition:

| Ingredients | Quantity (mg/tablet) |
|---|---|
| Active compound | 400 |
| corn starch | 50 |
| lactose | 145 |
| magnesium stearate | 5 |

The above ingredients are mixed intimately and pressed into single scored tablets.

Other compounds of Formula I, such as those prepared in accordance with Reaction Schemes A and B, and Examples 1–22 can be used as the active compound in the preparation of the tablet formulations of this example.

EXAMPLE 35

Injectable Formulation

This example illustrates the preparation of a representative pharmaceutical formulation containing an active compound of Formula I, e.g., Me-RS-SO(NH)-(CH$_2$-L-Leu)-Phe-Ala-NH$_2$.

An injectable preparation is prepared having the following composition:

| Ingredients | Quantity |
|---|---|
| Active compound | 0.2 g |
| water (distilled, sterile) | q.s. to 20.0 mL |

Other compounds of Formula I, such as those prepared in accordance with Reaction Schemes A and B, and Examples 1–20 can be used as the active compound in the preparation of the injection administrable formulations of this example.

EXAMPLE 36

Suppository Formulation

This example illustrates the preparation of a representative pharmaceutical formulation containing an active compound of Formula I, e.g., n-Bu-S(NH)$_2$-(CH$_2$-DL-Leu)-Trp-NHBn.

A suppository totalling 2.5 grams is prepared having the following composition:

| Ingredients | Quantity |
|---|---|
| Active compound | 500 mg |
| witepsol H-15* | q.s. to 2.5 g |

(*triglycerides of saturated vegatable fatty acid; a product of Riches-Nelson, Inc., New York, N.Y.).

Other compounds of Formula I, such as those prepared in accordance with Reaction Schemes A and B, and Examples 1–22 can be used as the active compound in the preparation of the suppository formulations of this example.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of the formula

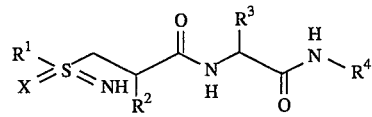

wherein:

$R^1$ is selected from the group consisting of lower-alkyl, hydroxy lower-alkyl, amino lower-alkyl, carbamoyl lower-alkyl, lower-alkyl carbonyl, lower-alkyoxyalkyl, aralkyl and heteroaralkyl;

X is NH or O;

$R^2$ is selected from the group consisting of hydrogen, lower-alkyl and aralkyl;

$R^3$ is selected from the group consisting of hydrogen, lower-alkyl, amino lower-alkyl, guanyl lower-alkyl, aralkyl and heteroaralkyl; and $R^4$ is selected from the group consisting of lower alkyl, aralkyl and —CH($R^5$)—C(O)NH$_2$, wherein $R^5$ is selected from the group consisting of hydrogen, lower-alkyl, amino lower-alkyl, guanyl lower-alkyl, imidazoylalkyl, hydroxymethyl, 1-hydroxyethyl, mercapto lower-alkyl, and methylthio lower-alkyl;

or a pharmaceutically acceptable ester, ether or salt thereof.

2. The compound of claim 1 wherein X is NH.

3. The compound of claim 2 wherein the carbon that is the point of attachment for $R^2$ is in the L-configuration.

4. The compound of claim 3 wherein $R^2$ is selected from the group consisting of lower-alkyl, phenylmethyl, 4-hydroxyphenylmethyl, 3-indolylmethyl, 4-methoxyphenylmethyl and phenylethyl.

5. The compound of claim 4 wherein $R^2$ is lower-alkyl.

6. The compound of claim 5 wherein $R^2$ is 2-methylpropyl.

7. The compound of claim 4 wherein $R^2$ is 4-methoxyphenylmethyl.

8. The compound of claim 4 wherein $R^3$ is selected from the group consisting of phenylmethyl, 4-hydroxyphenylmethyl, 3-indolylmethyl, 4-methoxyphenylmethyl and phenylethyl.

9. The compound of claim 8 wherein $R^3$ is phenylmethyl.

10. The compound of claim 8 wherein $R^3$ is 3-indolylmethyl.

11. The compound of claim 8 wherein $R^4$ is methyl.

12. The compound of claim 8 wherein $R^4$ is phenylmethyl.

13. The compound of claim 8 wherein $R^4$ is $-C(R^5)-C(O)NH_2$.

14. The compound of claim 13 wherein $R^5$ is lower-alkyl.

15. The compound of claim 14 wherein $R^5$ is methyl.

16. The compound of claim 8 wherein $R^1$ is lower-alkyl.

17. The compound of claim 16 wherein $R^1$ is methyl.

18. The compound of claim 16 wherein $R^1$ is n-butyl.

19. The compound of claim 17 wherein $R^2$ is 2-methylpropyl.

20. The compound of claim 18 wherein $R^2$ is 2-methylpropyl.

21. The compound of claim 18 wherein $R^2$ is 4-methoxyphenylmethyl.

22. The compound of claim 1 wherein X is O.

23. The compound of claim 22 wherein the carbon that is the point of attachment for $R^2$ is in the L-configuration.

24. The compound of claim 23 wherein $R^2$ is lower-alkyl.

25. The compound of claim 24 wherein $R^2$ is 2-methylpropyl.

26. The compound of claim 24 wherein $R^3$ is selected from the group consisting of phenylmethyl, 4-hydroxyphenylmethyl, 3-indolylmethyl, 4-methoxyphenylmethyl and phenylethyl.

27. The compound of claim 26 wherein $R^3$ is phenylmethyl.

28. The compound of claim 26 wherein $R^3$ is 3-indolylmethyl.

29. The compound of claim 26 wherein $R^4$ is methyl.

30. The compound of claim 26 wherein $R^4$ is phenylmethyl.

31. The compound of claim 26 wherein $R^4$ is $-CH(R^5)-C(O)-NH_2$.

32. The compound of claim 31 wherein $R^5$ is lower-alkyl.

33. The compound of claim 32 wherein $R^5$ is methyl.

34. The compound of claim 26 wherein $R^1$ is lower-alkyl.

35. The compound of claim 34 wherein $R^1$ is methyl

36. The compound of claim 34 wherein $R^1$ is n-butyl.

37. The compound of claim 34 wherein $R^2$ is lower-alkyl.

38. The compound of claim 1 that is Me-S(NH)$_2$-(CH$_2$-DL-Leu)-Trp-NHBn.

39. The compound of claim 1 that is n-Bu-S(NH)$_2$-(CH$_2$-DL-Leu)-Trp-NHBn.

40. The compound of claim 1 that is n-Bu-S(NH)$_2$-(CH$_2$-DL-TyrOCH$_3$)-Trp-NHBn.

41. The compound of claim 1 that is Me-RS-SO(NH)-(CH$_2$-L-Leu)-Phe-Ala-NH$_2$.

42. The compound of claim 1 that is n-Bu-RS-SO(NH)-(CH$_2$-L-Leu)-Phe-Ala-NH$_2$.

43. A pharmaceutical composition comprising a compound of the formula wherein:

$R^1$ is selected from the group consisting of lower-alkyl, hydroxy lower-alkyl, amino lower-alkyl, carbamoyl lower-alkyl, lower-alkyl carbonyl, lower-alkyoxyalkyl, aralkyl and heteroaralkyl;

X is NH or O;

$R^2$ is selected from the group consisting of hydrogen, lower-alkyl and aralkyl;

$R^3$ is selected from the group consisting of hydrogen, lower-alkyl, amino lower-alkyl, guanyl lower-alkyl, aralkyl and heteroaralkyl; and $R^4$ is selected from the group consisting of lower alkyl, aralkyl and $-CH(R^5)-C(O)NH_2$, wherein $R^5$ is selected from the group consisting of hydrogen, lower-alkyl, amino lower-alkyl, guanyl lower-alkyl, imidazoylalkyl, hydroxymethyl, 1-hydroxyethyl, mercapto lower-alkyl, and methylthio lower-alkyl; or a pharmaceutically acceptable ester, ether or salt thereof and pharmaceutically acceptable excipients useful for modulating physiological functions or treating diseases and disease conditions associated with matrix metalloproteinase modulation.

* * * * *